(12) United States Patent
Omori et al.

(10) Patent No.: US 8,537,210 B2
(45) Date of Patent: Sep. 17, 2013

(54) CONTROLLING LIGHT SOURCE WITH ENDOSCOPE TYPE

(75) Inventors: Koji Omori, Tokyo (JP); Mutsumi Ohshima, Tokyo (JP); Yasukazu Kogen, Tokyo (JP); Tomoya Takahashi, Tokyo (JP); Atsushi Shimada, Tokyo (JP)

(73) Assignee: Olympus Corporation (JP)

( * ) Notice: Subject to any disclaimer, the term of this patent is extended or adjusted under 35 U.S.C. 154(b) by 1518 days.

(21) Appl. No.: 11/562,614

(22) Filed: Nov. 22, 2006

(65) Prior Publication Data

US 2007/0088193 A1 Apr. 19, 2007

Related U.S. Application Data

(63) Continuation of application No. PCT/JP2005/009480, filed on May 24, 2005.

(30) Foreign Application Priority Data

May 24, 2004 (JP) ................. 2004-152699
Sep. 7, 2004 (JP) ................. 2004-260134
Sep. 7, 2004 (JP) ................. 2004-260135

(51) Int. Cl.
*A61B 1/04* (2006.01)
*A61B 1/06* (2006.01)

(52) U.S. Cl.
USPC ............................. 348/68; 600/175

(58) Field of Classification Search
USPC ........................... 348/68; 600/175
See application file for complete search history.

(56) References Cited

U.S. PATENT DOCUMENTS

| 4,433,675 | A | 2/1984 | Konoshima |
| 4,983,019 | A | 1/1991 | Ikuno et al. |
| 6,432,041 | B1* | 8/2002 | Taniguchi et al. ............ 600/118 |
| 7,179,222 | B2* | 2/2007 | Imaizumi et al. ............ 600/109 |
| 2001/0029318 | A1* | 10/2001 | Honda et al. .................. 600/180 |
| 2002/0175993 | A1 | 11/2002 | Ueno et al. |
| 2002/0177751 | A1 | 11/2002 | Ueno et al. |
| 2003/0063188 | A1* | 4/2003 | Takahashi et al. ............. 348/65 |
| 2004/0030221 | A1* | 2/2004 | Ogawa ......................... 600/175 |

(Continued)

FOREIGN PATENT DOCUMENTS

| JP | 57-164031 | 10/1982 |
| JP | A-57-164031 | 10/1982 |

(Continued)

OTHER PUBLICATIONS

Japanese Office Action dated Nov. 24, 2009 in corresponding Japanese Patent Application No. 2004-152699.

(Continued)

*Primary Examiner* — Richard Torrente
(74) *Attorney, Agent, or Firm* — Ostrolenk Faber LLP

(57) ABSTRACT

A light source device for an endoscope, characterized by having a light source for supplying illuminating light to an object, endoscope connection unit optically connected to an endoscope that has discrimination information for discriminating the kind of endoscope, discrimination unit for discriminating the endoscope based on the discrimination information of the endoscope connected to the endoscope connection unit, change unit for the changing illumination condition of the illuminating light, and control unit for controlling the change unit based on the result of discrimination by the discrimination unit.

17 Claims, 50 Drawing Sheets

(56) References Cited

U.S. PATENT DOCUMENTS

| | | |
|---|---|---|
| 2004/0046865 A1 | 3/2004 | Ueno et al. |
| 2004/0215060 A1 | 10/2004 | Ueno et al. |
| 2007/0100207 A1 | 5/2007 | Ueno et al. |

FOREIGN PATENT DOCUMENTS

| | | |
|---|---|---|
| JP | U-58-77708 | 5/1983 |
| JP | U-58-81508 | 6/1983 |
| JP | A-59-11830 | 1/1984 |
| JP | 1-295213 | 11/1989 |
| JP | 05-053064 | 3/1993 |
| JP | A-7-299027 | 11/1995 |
| JP | 8-211308 | 8/1996 |
| JP | 2000-041942 | 2/2000 |
| JP | A-2000-75219 | 3/2000 |
| JP | 2002-095635 | 4/2002 |
| JP | 2002-336196 | 11/2002 |
| JP | 2003-210403 | 7/2003 |
| JP | A-2003-210403 | 7/2003 |
| JP | 2004-121486 | 4/2004 |
| JP | 2005-006974 | 1/2005 |

OTHER PUBLICATIONS

English translation of Japanese Office Action issued Nov. 24, 2009 in connection with corresponding Japanese Patent Application No. 2004-152699.

Prior Art Information List with concise explanation of relevance.

International Search Report PCT/JP2005/009480 dated Aug. 9, 2005 (Japanese Patent Office).

Japanese Office Action dated Sep. 1, 2009 in corresponding Japanese Patent Application No. 2004-152699 (Japanese language).

\* cited by examiner

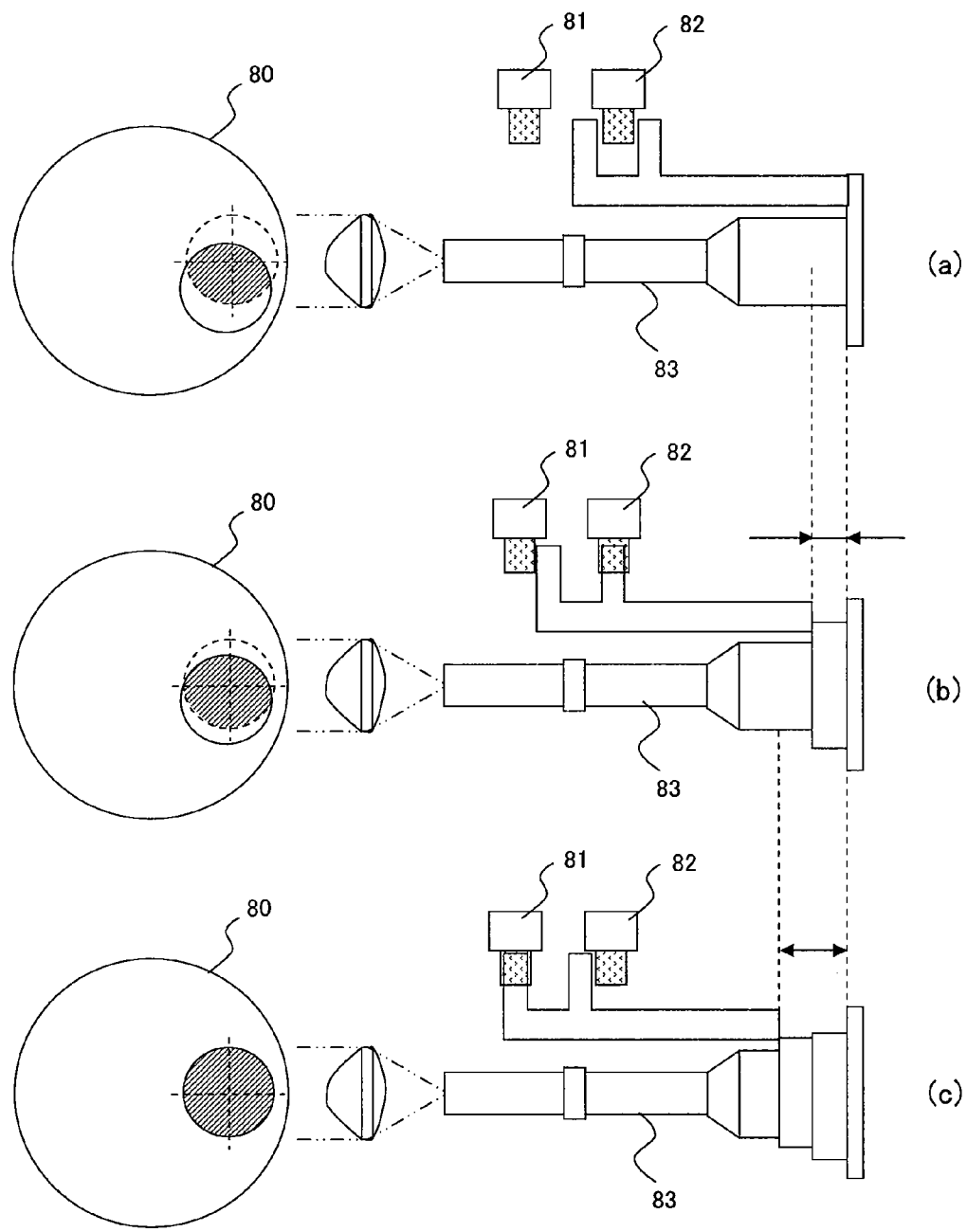
F I G. 1

LIGHT GUIDE CONNECTED NORMALLY

|  | OPTICAL SENSOR 20 | OPTICAL SENSOR 26 |
|---|---|---|
| UNCONNECTED | × | ○ |
| LOW BRIGHTNESS CONNECTED | × | × |
| MIDDLE BRIGHTNESS CONNECTED | ○ | × |

○ : SHIELDING PRESENT IN SENSING AREA OF OPTICAL SENSOR (SHORT)

× : SHIELDING ABSENT IN SENSING AREA OF OPTICAL SENSOR (OPEN)

F I G. 8 A

FAILURE IN OPTICAL SENSOR 20

|  | OPTICAL SENSOR 20 | OPTICAL SENSOR 26 |
|---|---|---|
| UNCONNECTED | × | ○ |
| LOW BRIGHTNESS CONNECTED | × | × |
| MIDDLE BRIGHTNESS CONNECTED | × | × |

○ : SHIELDING PRESENT IN SENSING AREA OF OPTICAL SENSOR (SHORT)

× : SHIELDING ABSENT IN SENSING AREA OF OPTICAL SENSOR (OPEN)

F I G. 8 B

FAILURE IN OPTICAL SENSOR 26

| | OPTICAL SENSOR 20 | OPTICAL SENSOR 26 |
|---|---|---|
| UNCONNECTED | × | × |
| LOW BRIGHTNESS CONNECTED | × | × |
| MIDDLE BRIGHTNESS CONNECTED | ○ | × |

○ : SHIELDING PRESENT IN SENSING AREA OF OPTICAL SENSOR (SHORT)

× : SHIELDING ABSENT IN SENSING AREA OF OPTICAL SENSOR (OPEN)

FIG. 8C

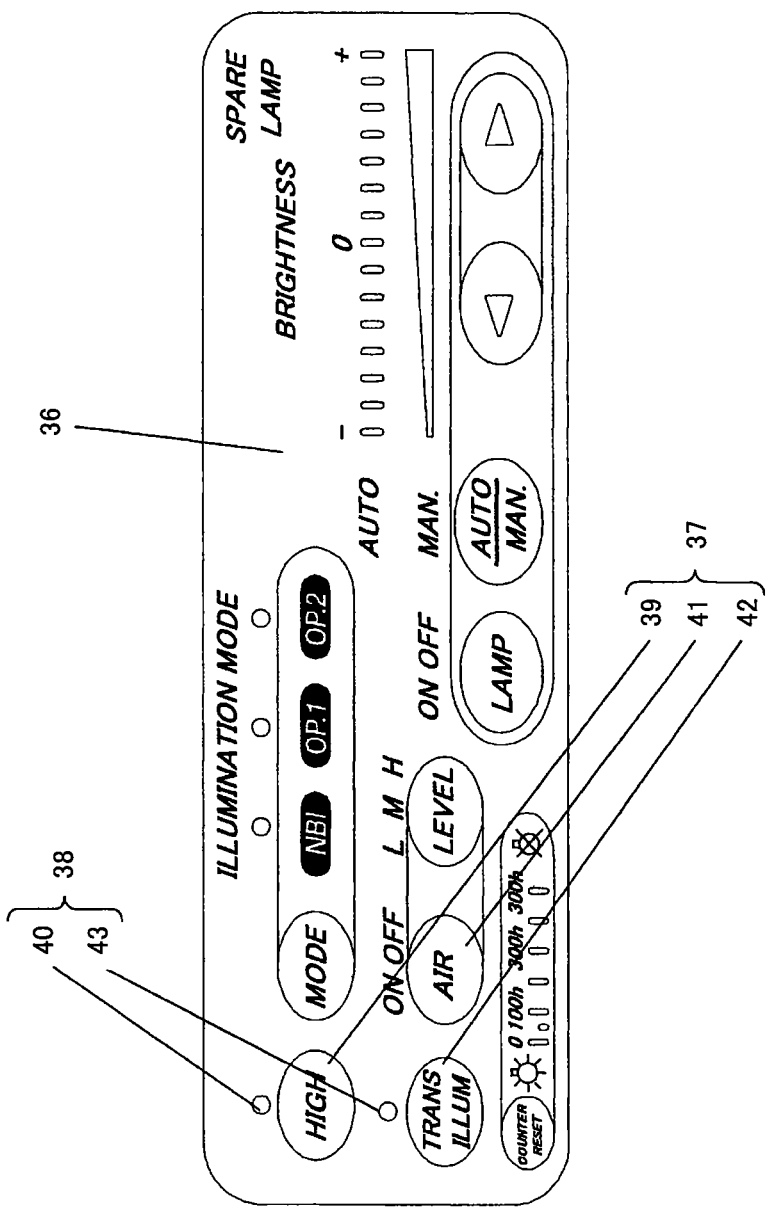
F I G. 9

LIGHT GUIDE CONNECTED NOMRMALLY

|  | OPTICAL SENSOR 43 | OPTICAL SENSOR 44 | OPTICAL SENSOR 48 |
|---|---|---|---|
| UNCONNECTED | × | × | ○ |
| LOW BRIGHTNESS CONNECTED | × | × | × |
| MIDDLE BRIGNTNESS CONNECTED | ○ | × | × |
| HIGH BRIGHTNESS CONNECTED | × | ○ | × |

○ : SHIELDING PRESENT IN SENSING AREA OF OPTICAL SENSOR (SHORT)

× : SHIELDING ABSENT IN SENSING AREA OF OPTICAL SENSOR (OPEN)

FIG. 13A

FAILURE IN OPTICAL SENSOR 43

| | OPTICAL SENSOR 43 | OPTICAL SENSOR 44 | OPTICAL SENSOR 48 |
|---|---|---|---|
| UNCONNECTED | × | × | ○ |
| LOW BRIGHTNESS CONNECTED | × | × | × |
| MIDDLE BRIGNTNESS CONNECTED | × | × | × |
| HIGH BRIGHTNESS CONNECTED | × | ○ | × |

○ : SHIELDING PRESENT IN SENSING AREA OF OPTICAL SENSOR (SHORT)

× : SHIELDING ABSENT IN SENSING AREA OF OPTICAL SENSOR (OPEN)

FIG. 13B

FAILURE IN OPTICAL SENSOR 44

| | OPTICAL SENSOR 43 | OPTICAL SENSOR 44 | OPTICAL SENSOR 48 |
|---|---|---|---|
| UNCONNECTED | × | × | ○ |
| LOW BRIGHTNESS CONNECTED | × | × | × |
| MIDDLE BRIGNTNESS CONNECTED | ○ | × | × |
| HIGH BRIGHTNESS CONNECTED | × | × | × |

○ : SHIELDING PRESENT IN SENSING AREA OF OPTICAL SENSOR (SHORT)

× : SHIELDING ABSENT IN SENSING AREA OF OPTICAL SENSOR (OPEN)

FIG. 13C

FAILURE IN OPTICAL SENSOR 48

| | OPTICAL SENSOR 43 | OPTICAL SENSOR 44 | OPTICAL SENSOR 48 |
|---|---|---|---|
| UNCONNECTED | × | × | × |
| LOW BRIGHTNESS CONNECTED | × | × | × |
| MIDDLE BRIGNTNESS CONNECTED | ○ | × | × |
| HIGH BRIGHTNESS CONNECTED | × | ○ | × |

○ : SHIELDING PRESENT IN SENSING AREA OF OPTICAL SENSOR (SHORT)

× : SHIELDING ABSENT IN SENSING AREA OF OPTICAL SENSOR (OPEN)

F I G. 1 3 D

RESPONSE MOVING MEMBER 45 IS FIXED AT HIGH
BRIGHTNESS CONNECTOR POSITION

|  | OPTICAL SENSOR 43 | OPTICAL SENSOR 44 | OPTICAL SENSOR 48 |
| --- | --- | --- | --- |
| UNCONNECTED | × | ○ | ○ |
| LOW BRIGHTNESS CONNECTED | × | ○ | × |
| MIDDLE BRIGHTNESS CONNECTED | × | ○ | × |
| HIGH BRIGHTNESS CONNECTED | × | ○ | × |

○ : SHIELDING PRESENT IN SENSING AREA OF OPTICAL SENSOR (SHORT)

× : SHIELDING ABSENT IN SENSING AREA OF OPTICAL SENSOR (OPEN)

FIG. 14A

RESPONSE MOVING MEMBER 45 IS FIXED AT MIDDLE
BRIGHTNESS CONNECTOR POSITION

|  | OPTICAL SENSOR 43 | OPTICAL SENSOR 44 | OPTICAL SENSOR 48 |
|---|---|---|---|
| UNCONNECTED | ○ | × | ○ |
| LOW BRIGHTNESS CONNECTED | ○ | × | × |
| MIDDLE BRIGHTNESS CONNECTED | ○ | × | × |
| HIGH BRIGHTNESS CONNECTED | × | ○ | × |

○ : SHIELDING PRESENT IN SENSING AREA OF OPTICAL SENSOR (SHORT)

× : SHIELDING ABSENT IN SENSING AREA OF OPTICAL SENSOR (OPEN)

F I G. 1 4 B

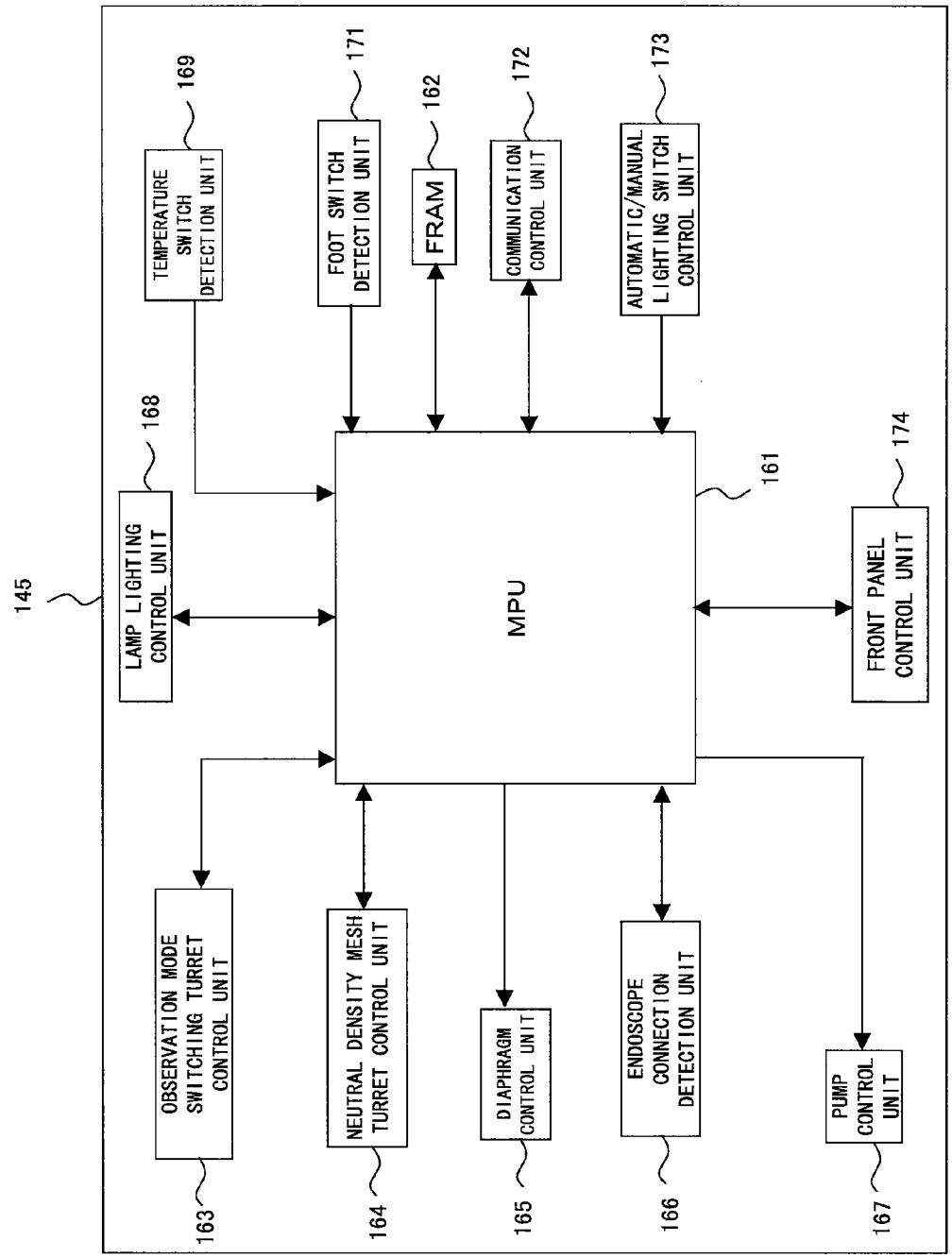
F I G. 17

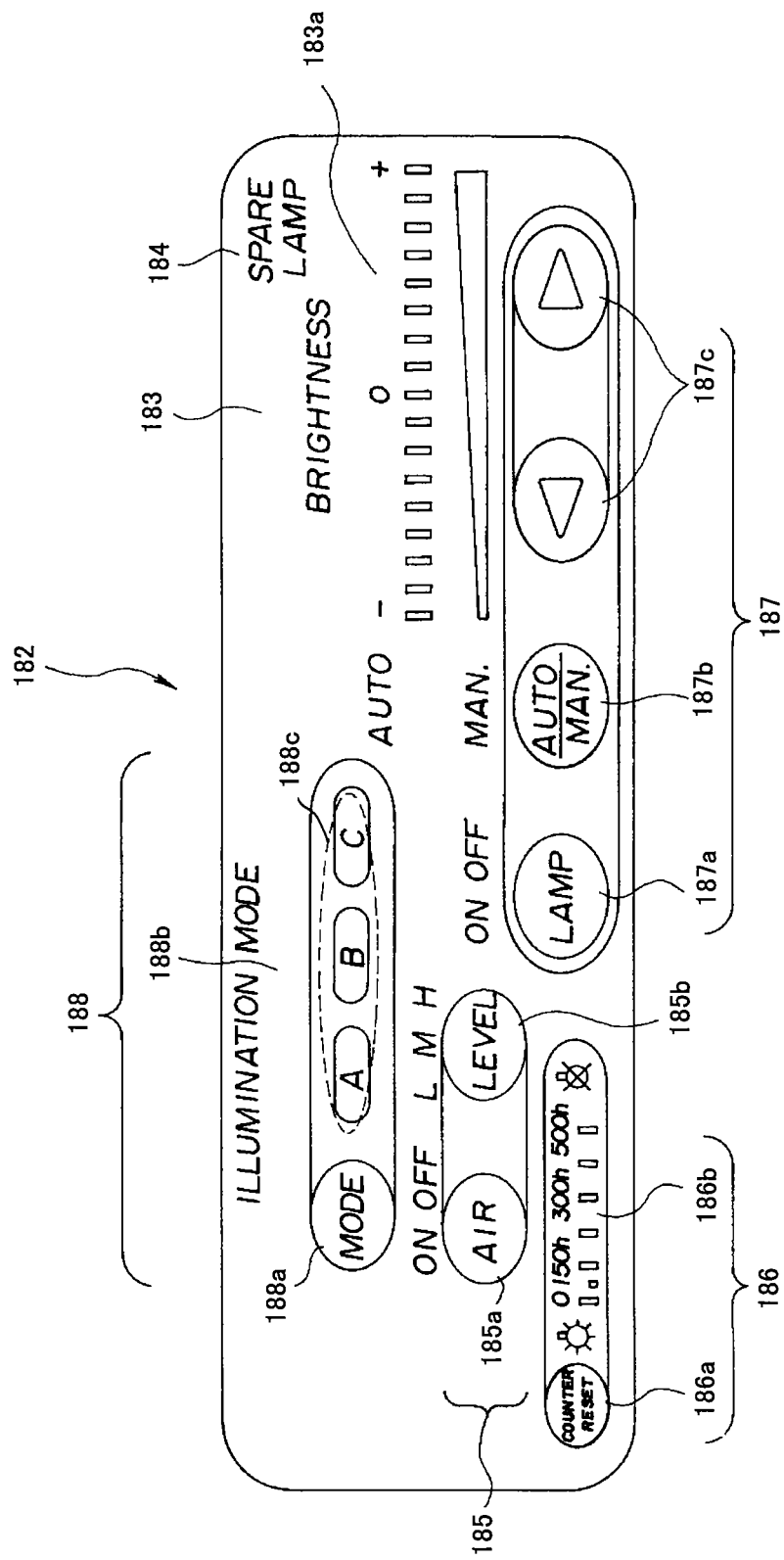
F I G. 19

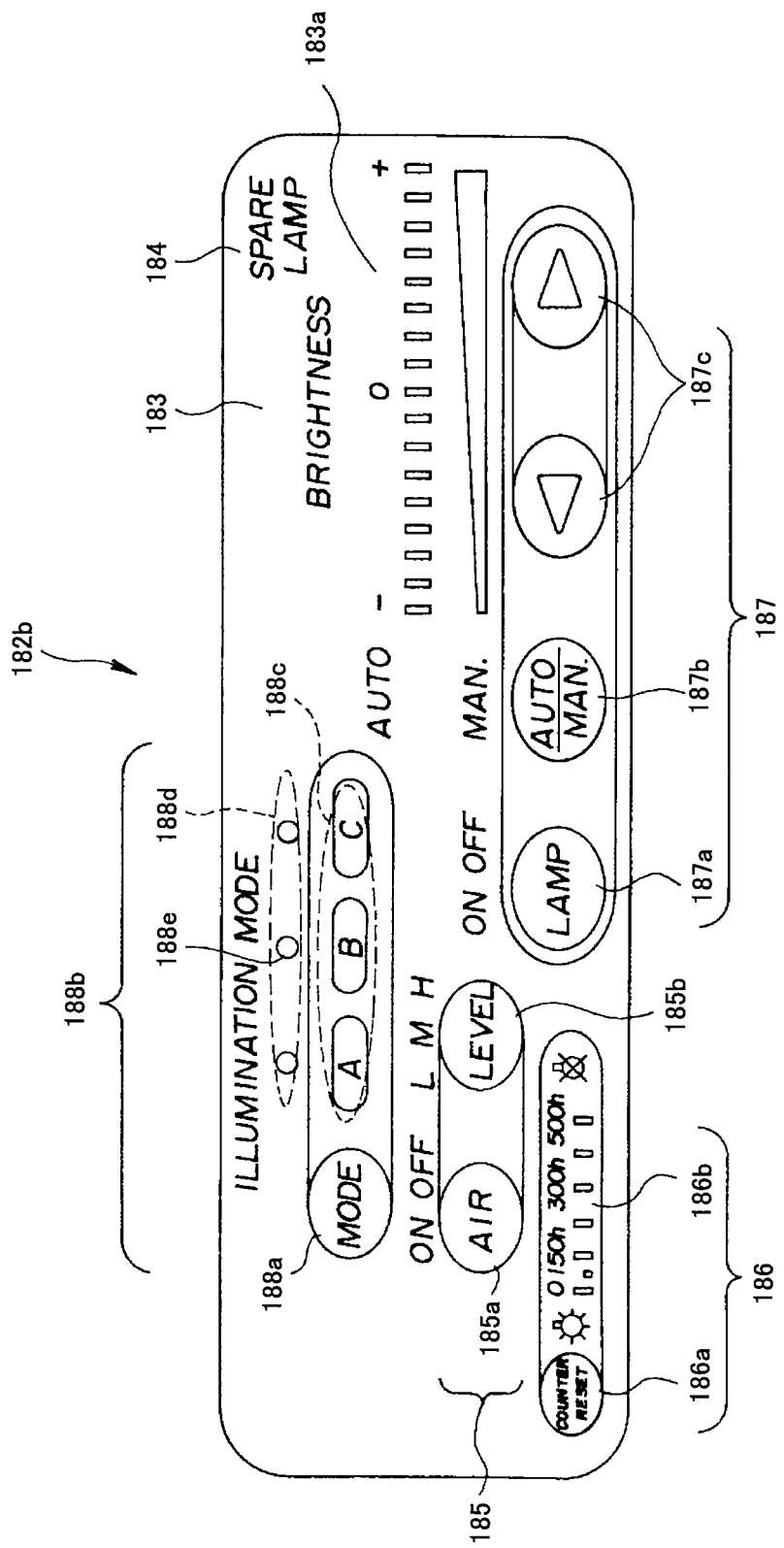
F I G. 21

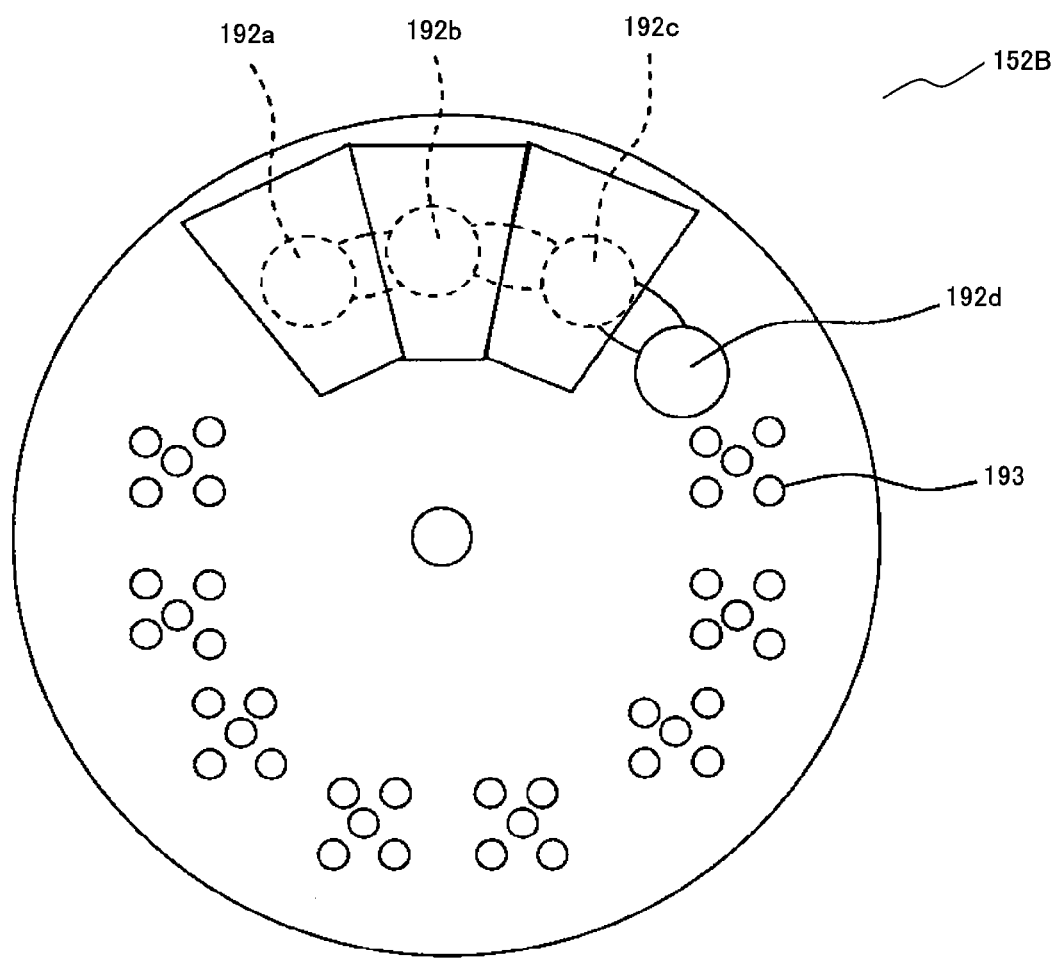
F I G. 25

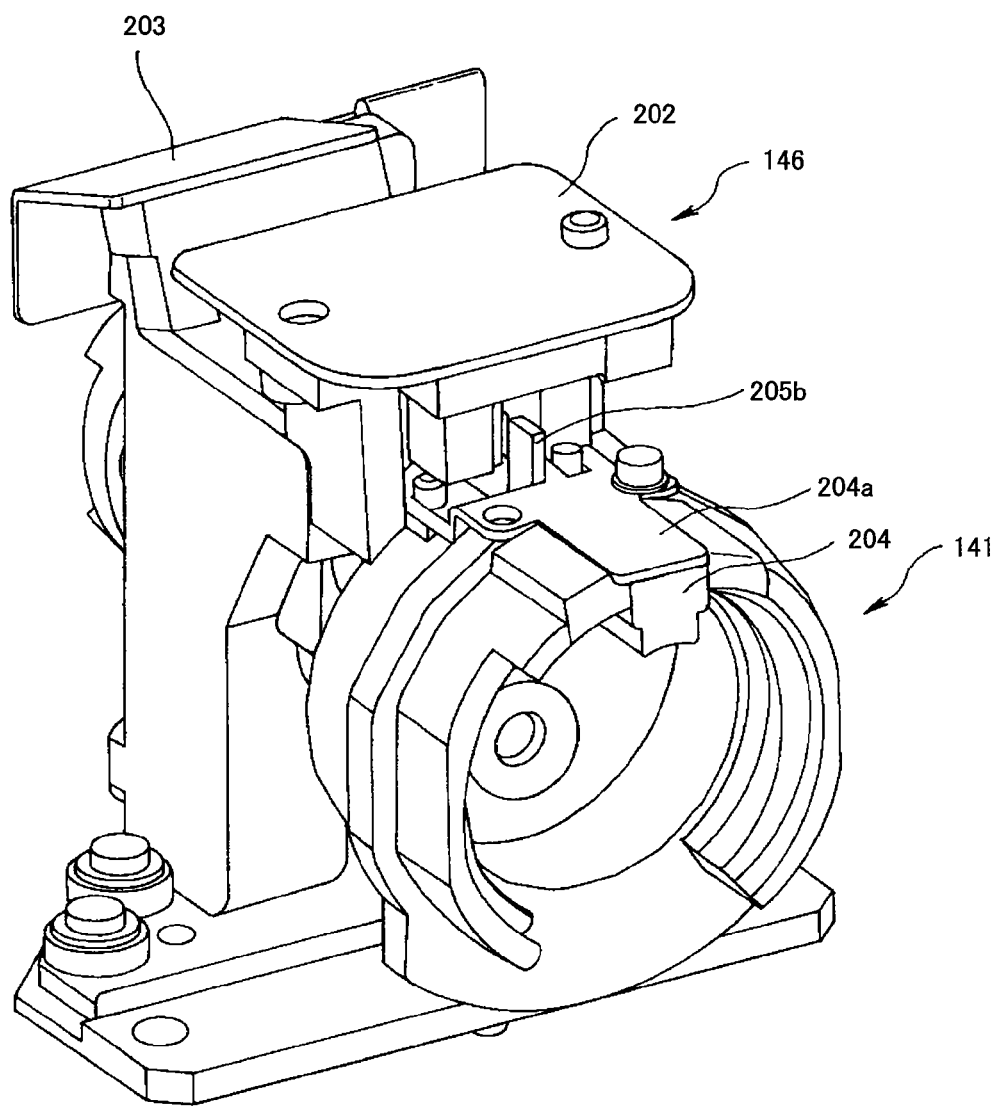
F I G. 31

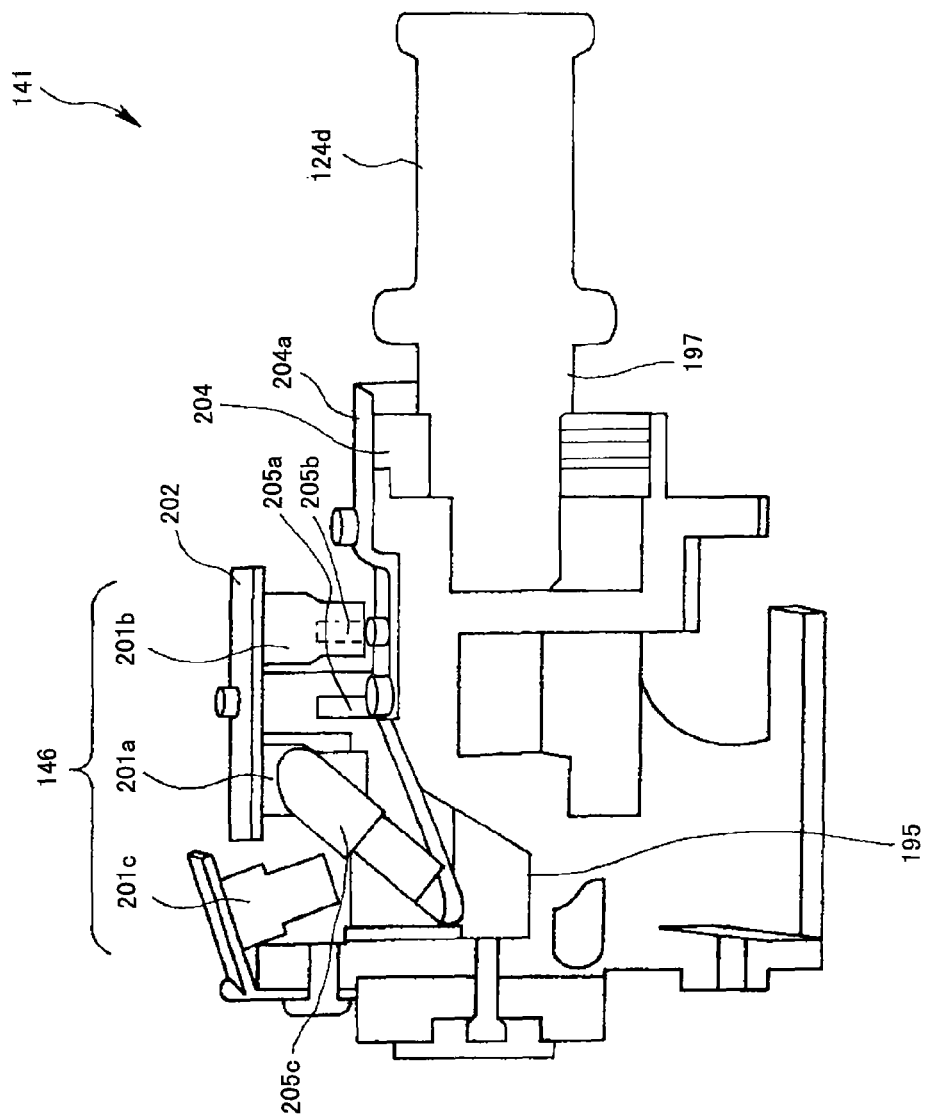
F I G. 3 4

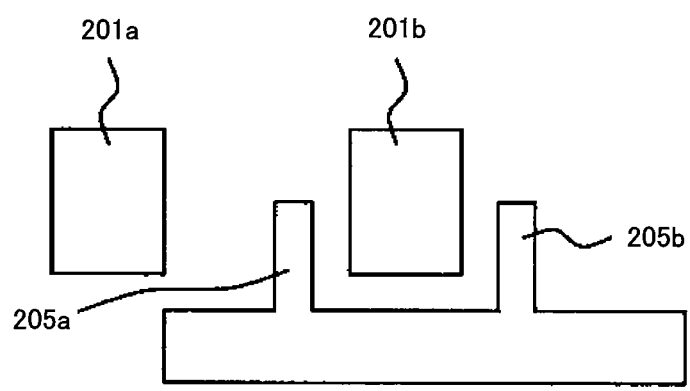
F I G. 3 6

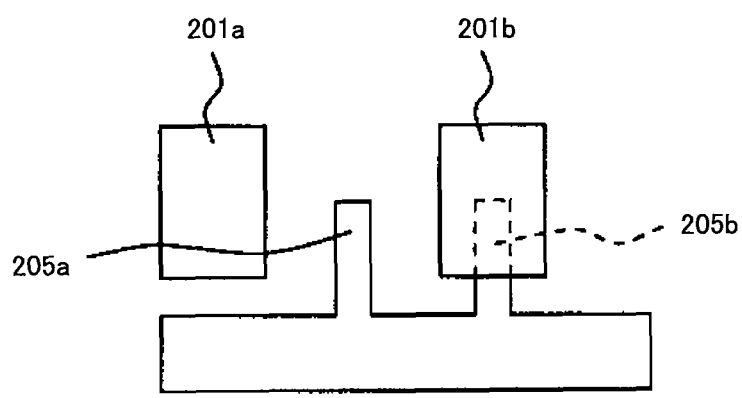
F I G. 3 7

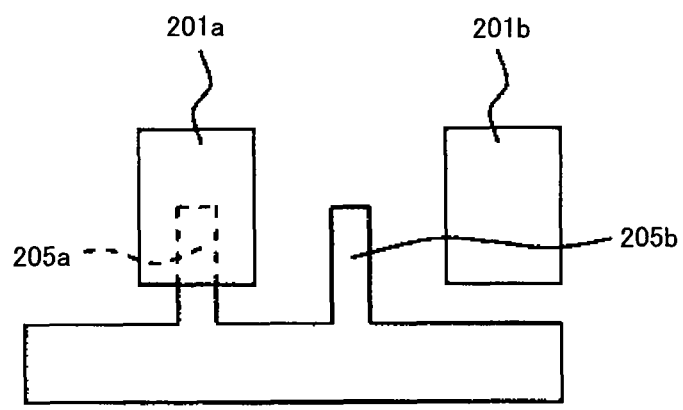
F I G. 3 8

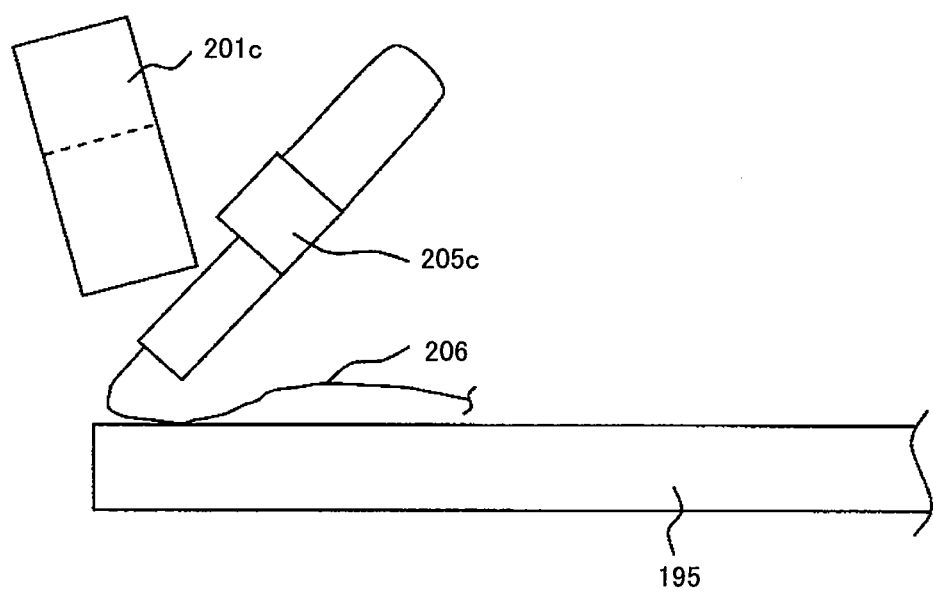
F I G. 4 0

CONTROLLING LIGHT SOURCE WITH ENDOSCOPE TYPE

CROSS REFERENCE TO RELATED APPLICATIONS

This is a Continuation Application of PCT Application No. PCT/JP2005/009480, filed May 24, 2005, which was not published under PCT Article 21(2) in English.

This application is based upon and claims the benefit of priority from the prior Japanese Patent Application No. 2004-152699, filed May 24, 2004, the entire contents of which are incorporated herein by reference.

This application is based upon and claims the benefit of priority from the prior Japanese Patent Application No. 2004-260135, filed Sep. 7, 2004, the entire contents of which are incorporated herein by reference.

This application is based upon and claims the benefit of priority from the prior Japanese Patent Application No. 2004-260134, filed Sep. 7, 2004, the entire contents of which are incorporated herein by reference.

BACKGROUND OF THE INVENTION

1. Field of the Invention

The present invention relates to a light source device for an endoscope.

2. Description of the Related Art

Endoscopes are widely used in medical and other fields. An endoscope comprises a long thin insertion unit. Endoscopes allow observations to be made of organs and body tissues in body cavities and also allow various treatments employing instruments inserted into an instrument insertion channel as necessary.

In an endoscope apparatus comprising such an endoscope, the subject body illuminates the object site by guiding illuminating light from a light source device employing a light guide etc., and an endoscope image is obtained by capturing the reflected light.

The above endoscope apparatus can capture an image by an endoscope image capturing means, and perform signal processing by a signal processor device (hereinafter referred to as "processor"), and display endoscope image on an observation monitor. Consequently body tissues can be observed.

As described above, an endoscope system comprises a light source device for supplying illuminating light to a light guide incorporated in the endoscope in order to irradiate the subject body. The light guide is used in combination with a light source device, and there are a variety of types of light guides. For example, in a type of light guide with a small incident end diameter, if the input illuminating light is too bright, it is probable that the heating value of the irradiated part in body cavities will become excessively large. Hence, when the endoscope is in use, the brightness of the supplied illuminated light has to be adjusted in accordance with the type of light guide. Consequently a light source device for an endoscope is disclosed that it should be able to obtain the appropriate brightness and light distribution of the illuminating light in accordance with the type of light guide connected to the light source device of an endoscope (for example, Patent Document 1).

FIG. 1 is a construction diagram of such a light source device for an endoscope. The light source device of FIG. 1 comprises light guide connector identifying means 81 and 82, limiting means 80, and light intensity adjustment means. The light guide connector identifying means 81 and 82 identifies the type of light guide connector 83 to be connected. The limiting means 80 limits the illuminating light that will be on the optical path of the illuminating light. The light intensity adjustment means appropriately adjusts the light intensity of the illuminating light incident on the light guide in accordance with the type of light guide connector 83 identified by the identifying means 81 and 82. In order to prevent the tip of the light guide from causing burns and heat damage in body cavities, it is possible to supply illuminating light with appropriate brightness to the endoscope so that the brightness of the incident illuminating light is not excessively intense, even if the endoscope has a light guide with a small incident end diameter.

In an endoscope apparatus, in usual cases of body tissue observation, the light source device emits white light (hereinafter referred to as normal light) in the visible light range, illuminates the object site of the subject body as frame sequential light by passing through a rotating filter such as RGB, for example, performs image processing by synchronization of an image signal based on the reflected light by a processor, and finally obtains color images (hereinafter referred to as the frame sequential method).

Alternatively, the endoscope apparatus is provided with color chips in front of the imaging area of a solid-state image sensor installed in the endoscope, captures images by separating the reflected light of the normal light into RGB in the color chips, performs image processing via a processor, and obtains color images (hereinafter referred to as the simultaneous method).

A variety of endoscope apparatuses for special light observations have been proposed since the optical absorption property and the optical scattering property are different according to the wavelength of the irradiating light in the body tissue.

For example, as a frame sequential method, as described in Japanese Patent Application Publication No. 2002-336196, an endoscope apparatus for fluorescent observation, which makes a diagnosis by utilizing a difference between normal tissue and lesions in autofluorescence generated from the body tissue by irradiating pump light such as ultraviolet rays and blue light on a body tissue, has been proposed in recent years.

As described in Japanese Patent Application Publication No. 2000-41942, an endoscope apparatus for infrared light observation, which enables an observation of the depth of the body tissue by irradiating infrared light on the body tissue as illuminating light, has been also been proposed. In addition, as described in Japanese Patent Application Publication No. 2002-95635, an endoscope apparatus for narrow-band light observation, which enables an observation around a superficial portion of the mucous membrane of the body tissue by irradiating the body tissue with blue narrow-band light as illuminating light, has been proposed.

Endoscopes used for the above observations need to be able to make at least two types of observations, a normal light observation and at least one special light observation. For example, with the use of the endoscope for fluorescent observation, normal light observation and fluorescent observation are possible. With the use of the endoscope apparatus for infrared light observation, normal light observation and infrared light observation are possible. Normal light observation and narrow-band light observation are possible using the endoscope apparatus for narrow-band light observation.

Similarly, in the simultaneous method, at least one special light observation in addition to normal light observation can be conducted, and, for example, normal light observation and a narrowband light observation are possible with the use of a narrowband light observation endoscope, and normal light observation and a fluorescent observation are possible with the use of a fluorescent observation endoscope.

In these endoscopes for special light observation, the switching operation between normal light observation and special light observation is performed by operating an operation unit of the endoscope, a processor, a switch provided on the front panel of the light source device, or a foot switch for the endoscope, etc.

In recent years, there have been increasing demands for a plurality of special light observation modes to be available to be used with one set of processor and light source device. The usage depends on the user, particularly whether the endoscope will be used for internal medicine or for surgery. For example, a physician may use an endoscope as a narrowband observation endoscope, a surgeon may use the endoscope as a fluorescent observation endoscope, and another surgeon may use the endoscope as an infrared light observation endoscope.

Here, the special light observations have different spectroscopic characteristics for the illuminating light supplied from the light source device, different transmission characteristics of the objective optical system of the endoscope, different types of solid-state image sensors, and different signal processing in their processor devices, etc., in accordance with the observation mode.

As described above, conventional light source devices are provided with filters for special light observation modes in an observation mode switching turret comprising a plurality of observation mode filters corresponding to the observation mode.

Patent Document 1:
Japanese Patent Application Publication No. 2003-210403

Patent Document 2:
Japanese Patent Application Publication No. 2002-336196

Patent Document 3:
Japanese Patent Application Publication No. 2000-41942

Patent Document 4:
Japanese Patent Application Publication No. 2002-95635

SUMMARY OF THE INVENTION

The light source device relating to the present invention comprises a light source for supplying illuminating light to an object, endoscope connection means optically connected to an endoscope that has identification information for identifying the type of endoscope, identification means for identifying the endoscope based on the identification information of the endoscope connected to the endoscope connection means, change means for changing the illumination condition of the illuminating light, and control means for controlling the change means based on the result of identification by the identification means.

The light source device for an endoscope relating to the present invention comprises endoscope connection means, which can be selectively connected to a plurality of types of endoscopes, a light source for generating illuminating light supplied to an endoscope connected to the endoscope connection means, an optical system guiding illuminating light generated from the light source to the endoscope, an observation filter turret comprising a plurality of types of observation filters for limiting the wavelength range of light from the light source in accordance with the observation mode of the endoscope and that can set an observation filter corresponding to the observation mode of the endoscope on an optical path of the optical system, and a neutral density filter turret comprising a plurality of types of neutral density filters for darkening light from the light source in accordance with the observation mode of the endoscope and that can set a neutral density filter corresponding to the endoscope on an optical path of the optical system.

The light source device for an endoscope relating to the present invention comprises endoscope connection means that can be selectively connected to a plurality of types of endoscopes, a detection sensor provided in the endoscope connection means for detecting the type of endoscope, detection means for detecting the type of endoscope based on a signal from the detection sensor, memory for storing the setting content in accordance with the type of endoscope, and control means for making an automatic setting in accordance with the setting content stored in the memory based on the detection result of the detection means.

BRIEF DESCRIPTION OF THE DRAWINGS

FIG. 1 shows diagrams explaining the configurations of a light source device for an endoscope relating to prior art;

FIG. 8A shows diagrams showing combinations of the detection states of two optical sensors in embodiment 1 of the first mode;

FIG. 8B shows diagrams showing combinations of the detection states of two optical sensors in embodiment 1 of the first mode;

FIG. 8C shows diagrams showing combinations of the detection states of two optical sensors in embodiment 1 of the first mode;

FIG. 9 is an example of the operation panel of embodiment 1 of the first mode;

FIG. 13A shows diagrams showing combinations of the detection states of the three optical sensors in embodiment 2 of the first mode;

FIG. 13B shows diagrams showing combinations of the detection states of the three optical sensors in embodiment 2 of the first mode;

FIG. 13C shows diagrams showing combinations of the detection states of the three optical sensors in embodiment 2 of the first mode;

FIG. 13D shows diagrams showing combinations of the detection states of the three optical sensors in embodiment 2 of the first mode;

FIG. 14A shows diagrams showing combinations of the detection states of the three optical sensors in a case in which the response moving member is fixed in embodiment 2 of the first mode;

FIG. 14B shows diagrams showing combinations of the detection states of the three optical sensors in a case in which the response moving member is fixed in embodiment 2 of the first mode;

FIG. 17 is a block diagram showing an inner configuration of the control board of FIG. 16;

FIG. 19 is an enlarged view showing the configuration of the operation panel of FIG. 18;

FIG. 21 is an enlarged view showing the configuration of the operation panel of FIG. 20;

FIG. 25 is a front view of the neutral density mesh turret showing an example (1) of a variation of FIG. 24;

FIG. 31 is a perspective view showing the surroundings of the connector receiver unit of FIG. 22;

FIG. 34 is a cross-sectional view of a case in which the light source connector of the high-brightness rigid endoscope is connected to the connector receiver unit of FIG. 32;

FIG. 36 is an overview explanatory diagram showing the relation between the first and second photosensors and the first and the second protrusions in FIG. 32;

FIG. 37 is an overview explanatory diagram showing the relation between the first and second photosensors and the first and second protrusions in FIG. 33;

FIG. 38 is an overview explanatory diagram showing the relating between the first and second photosensors and the first and the second protrusions in FIG. 34;

FIG. 40 is an overview explanatory diagram showing the relation between the third photosensor and the third protrusion in the state in which the third photosensor is ON in the second mode;

DESCRIPTION OF THE PREFERRED EMBODIMENTS

<First Mode>

From the perspective of safety, it is desirable to have an endoscope that is safe for both operators of the endoscope system and patients, or subject bodies, etc., at all times, even when a failure occurs in a part of the endoscope system, including failures in the light source device (hereinafter referred to as a single failure).

There is a light source device that satisfies this requirement: it has a switch that an operator can switch to a safe brightness according to the type of connected endoscope. The switch is provided on the operation panel. In such a light source device, if there is a failure of the light guide, the light intensity of the illuminating light of the light guide, in general, can be adjusted from the operation panel. However, even if an illuminating light with unexpected light intensity is input into the endoscope due to a signal failure of the light guide, the light intensity cannot be adjusted without operation of the switch by the operator. In an emergency such as this, a light source device with improved safety that enables light intensity adjustment via operation of the switch by an operator, is required.

In the present mode, a light source device for an endoscope that performs automatic adjustment within the light source device to ensure a safe light intensity even during a failure in means of identifying the type or the connection state of the light guide of the endoscope, etc., and that prevents heat damage to bodies and the light guide, is explained.

In the following description, details of the preferred embodiment of the present invention are set forth with reference to the drawings.

(Embodiment 1)

Figure 2:
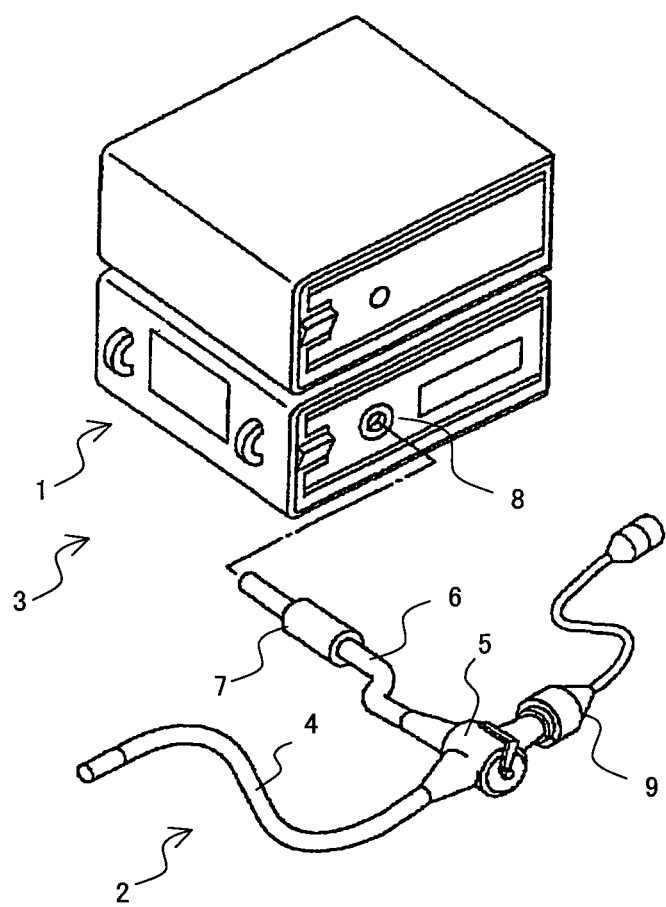
FIG. 2 is an overview of the whole configuration of the endoscope system relating to embodiment 1 of the first mode.

An explanation of a light source device of the first embodiment is provided below. FIG. 2 is an overview of the configuration of the entire endoscope system relating to embodiment 1 of the present invention. An endoscope system 3 comprises an endoscope 2 and a light source device 1. The light source device 1 supplies illuminating light into the endoscope 2.

The endoscope 2 is used for observation and treatment in body cavities, for example. The endoscope 2 comprises an insertion unit 4, an operation unit 5, and a light guide cable 6. The operation unit 5 is provided in the proximal end side of the insertion unit 4. The light guide cable 6 is connected to the side surface of the operation unit 5. The tip of the light guide cable 6 is provided with a light guide connector 7. The light guide connector 7 can be connected to a connector receiver unit 8, which is the output end of the light source device 1. The illuminating light supplied from the light source device 1 into the endoscope 2 is output from the distal end of the insertion unit 4 configured in the endoscope 2 toward the object. The image of the illuminated object is guided by an image guide configured in the endoscope 2, and observation and diagnosis are performed via the optical system.

It should be noted that in the case of adopting a TV camera system, when capturing images by attaching a TV camera head 9 in which an imaging apparatus such as CCD is built, the diagnosis is made in the following manner. Signal processing of the captured image's electrical signal from the TV camera head 9 is first performed in a camera control unit (CCU) 10. Next, the processed picture signal is transmitted to a monitor 11. The object image is projected on the screen of the monitor 11, and observation and diagnosis are made.

Figure 3:
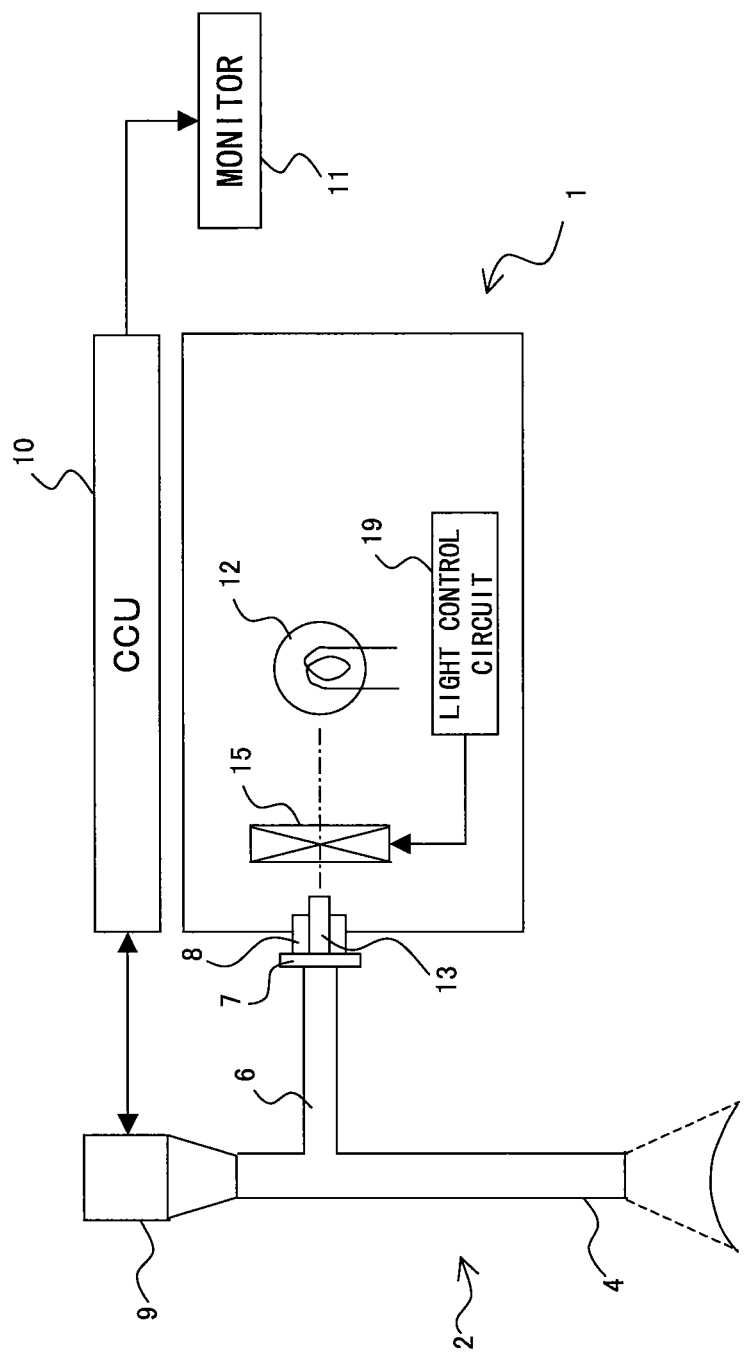
FIG. 3 is an overview of the light source device in the endoscope system of embodiment 1 of the first mode.

FIG. 3 is an overview of the light source device 1 in the endoscope system of FIG. 2. The light source device 1 comprises a lamp 12 within its device body. The illuminating light output from the lamp 12 is input into a light guide 13 of the light guide connector 7 of the endoscope 2 connected to the connector receiver unit 8 via the optical system.

Figure 4:
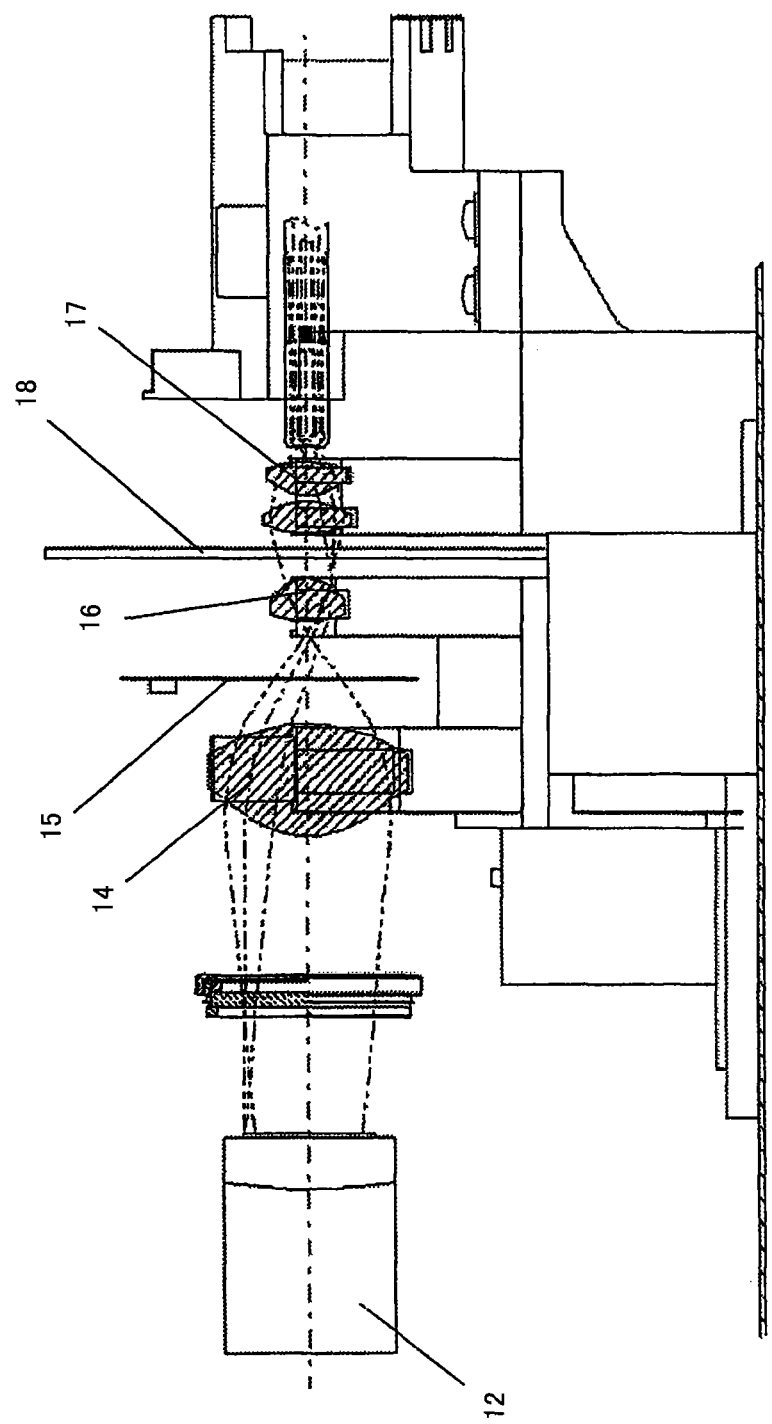
FIG. 4 is a diagram showing the configuration of the optical system of the light source device of embodiment 1 of the first mode.

FIG. 4 is a diagram showing the configuration of the optical system of the light source device 1 of FIG. 3. Arranged on the optical path of the illuminating light from lamp 12 are an output side lens 14, an aperture 15, a first input side lens 16, a second input side lens 17, and limiting means 18 in sequence.

The output side lens 14 first receives the illuminating light output from the lamp 12 and forms a collected light beam. The aperture 15 is arranged in a region immediately before the collecting point and controls the brightness by limiting the illuminating light. Note in FIG. 3 that the aperture 15 is controlled by a light control circuit 19 and is adjusted so that the brightness of the object is constant. The illuminating light is input into the first input side lens 16 via the aperture 15, and is converted into a collimated light beam. After being converted into a collimated light beam, the illuminating light is input into the second input side lens 17, and is collected once again. The collected illuminating light is input into the tip of the light guide 13 of the light guide connector 7 of the endoscope 2 connected to the connector receiver unit 8.

The limiting means 18 include a mask etc. The limiting means 18 is arranged in a position between the first input side lens 16 and the second input side lens 17 where the illuminating light converted into the collimated light beam by the first input side lens 16 is input. Based on an instruction from a control unit not shown in the drawing, the illuminating light input into the tip of the light guide 13 of the light guide connector 7 is limited by the mask etc. By the limiting means 18, the illuminating light input into the tip of the light guide 13 is limited to an appropriate light intensity in accordance with the type of light guide connector 7 of the endoscope 2.

Figure 5:
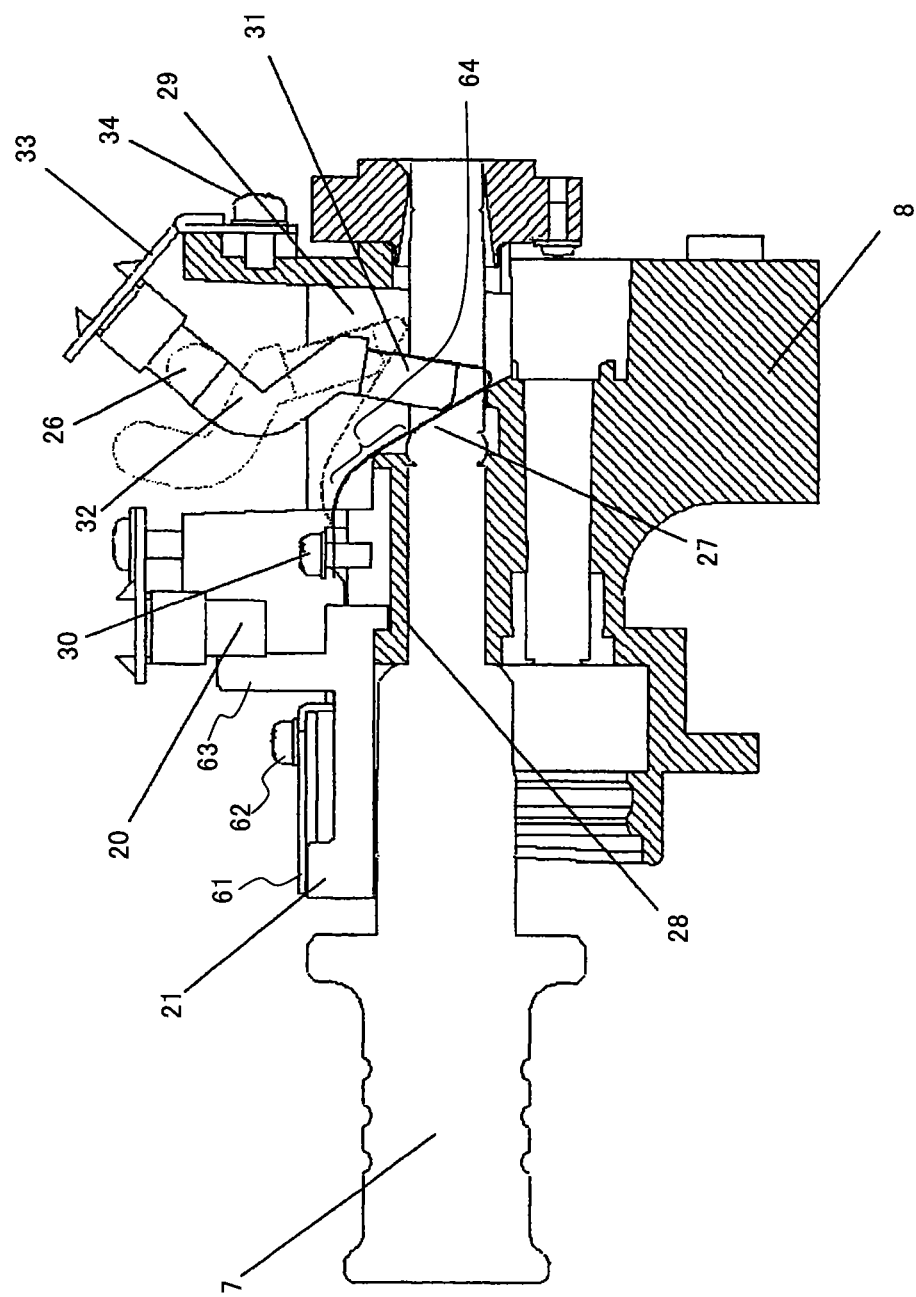
FIG. 5 is a cross-sectional diagram of the connector receiver unit of the light source device of the light source device of embodiment 1 of the first mode.

FIG. 5 is a cross-sectional diagram of the connector receiver unit 8 of the light source device 1. Two identification means are provided with the connector receiver unit 8 in the light source device 1.

The type identification means, which is one of the two identification means, comprises an optical sensor 20 and a response moving member 21 with a light-shielding unit 63. Force in the direction of the left of FIG. 5 is constantly applied to the response moving member 21 by an elastic body such as a spring along with a guide means not shown in the drawing. The response moving member 21 is provided so as to be movable toward the direction of the insertion axis of the light guide connector 7 when the light guide connector 7 of the endoscope 2 is connected to the connector receiver unit 8. The leftmost end of the response moving member 21 is provided with a stopper 61 fixed by a setscrew 62. The stopper 61 prevents the response moving member 21 from moving to the left.

Another identification means, the connection identification means, comprises an optical sensor 26 and a light-shielding spring 27 made of an elastic member. The optical sensor 26 is fixed on a bracket 33 by an engaging hook etc. and detects the presence/absence of the shielded object. The bracket 33 is screwed via setscrew 34 provided in the connector receiver unit 8. The light-shielding spring 27 is fixed in an approximate cantilevered state via setscrew 30 provided in the connector receiver unit 8. In addition, the light-shielding spring 27 is bent below a concave area 29 and is given force to form a slope 64. Accordingly, even when the light guide connector 7 is not connected, the illuminating light from the lamp 12, which is a light source, is shielded by the light-shielding spring 27. As a result, leakage of a large amount of light from the light source device 1, entering the endoscope 2, does not occur.

Figure 6:
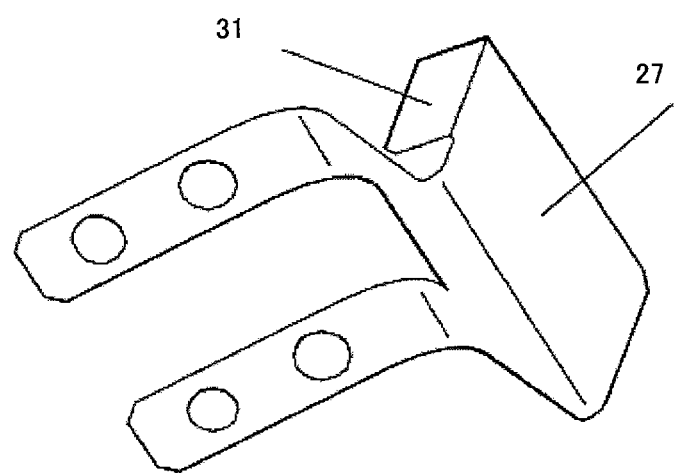
FIG. 6 is a diagram showing an example of the light-shielding spring of embodiment 1 of the first mode.

FIG. 6 is a diagram showing an example of the light-shielding spring 27. The light-shielding spring 27 is provided with an upward bend 31. If the light-shielding spring 27 is incorporated into the connector receiver unit 8, a black-colored insulation sheet 32 with good light shielding effect, or the like, for example, is fixed on the upward bend 31.

When the light guide connector 7 of the endoscope 2 is inserted into the insertion hole 28 of the connector receiver unit 8, the light-shielding spring 27 is pushed obliquely upward by a tip of the light guide connector 7 at a low strength (See FIG. 5). The light-shielding spring 27 withdraws obliquely upward making an approximate arc trajectory. The tip of the insulation sheet 32 moves obliquely upward when the light-shielding spring 27 moves obliquely upward for withdrawal.

The amount of movement of the insulation sheet 32 is set to be larger than the sensing area of the optical sensor 26. Therefore, the insulation sheet 32 is located in the sensing area of the optical sensor 26 when the light guide connector 7 is not connected; however, it withdraws outside the sensing area when the light guide connector 7 is connected. By doing this, that is, by moving the insulation sheet 32, the optical sensor 26 recognizes the state of "shielding object absent", sensing that the shielding object is absent in the sensing area. When the light guide connector 7 is not connected, the optical sensor 26, shielded by the insulation sheet 32, recognizes the state of "shielding object present".

The optical sensor 26 constitutes a part of a secondary circuit in the light source device 1. On the other hand, the light-shielding spring 27 constitutes a part of a patient circuit in the light source device 1. The insulation sheet 32 is provided in order to secure the insulation distance between the optical sensor 26 and the light-shielding spring 27 from the perspective of safety so that the optical sensor 26 of the secondary circuit and the light-shielding spring 27 of the patient circuit are not in electrical contact with each other.

The circuit configuration of the light source device, when the light guide connector 7 is not connected, may have the upward bend 31 of the light-shielding spring 27 arranged at a position in the direct sensing area. In such a case, when the light guide connector 7 is inserted, the upward bend 31 of the light-shielding spring 27 is to be arranged at a position outside of the sensing area of the optical sensor 26.

Figure 7:
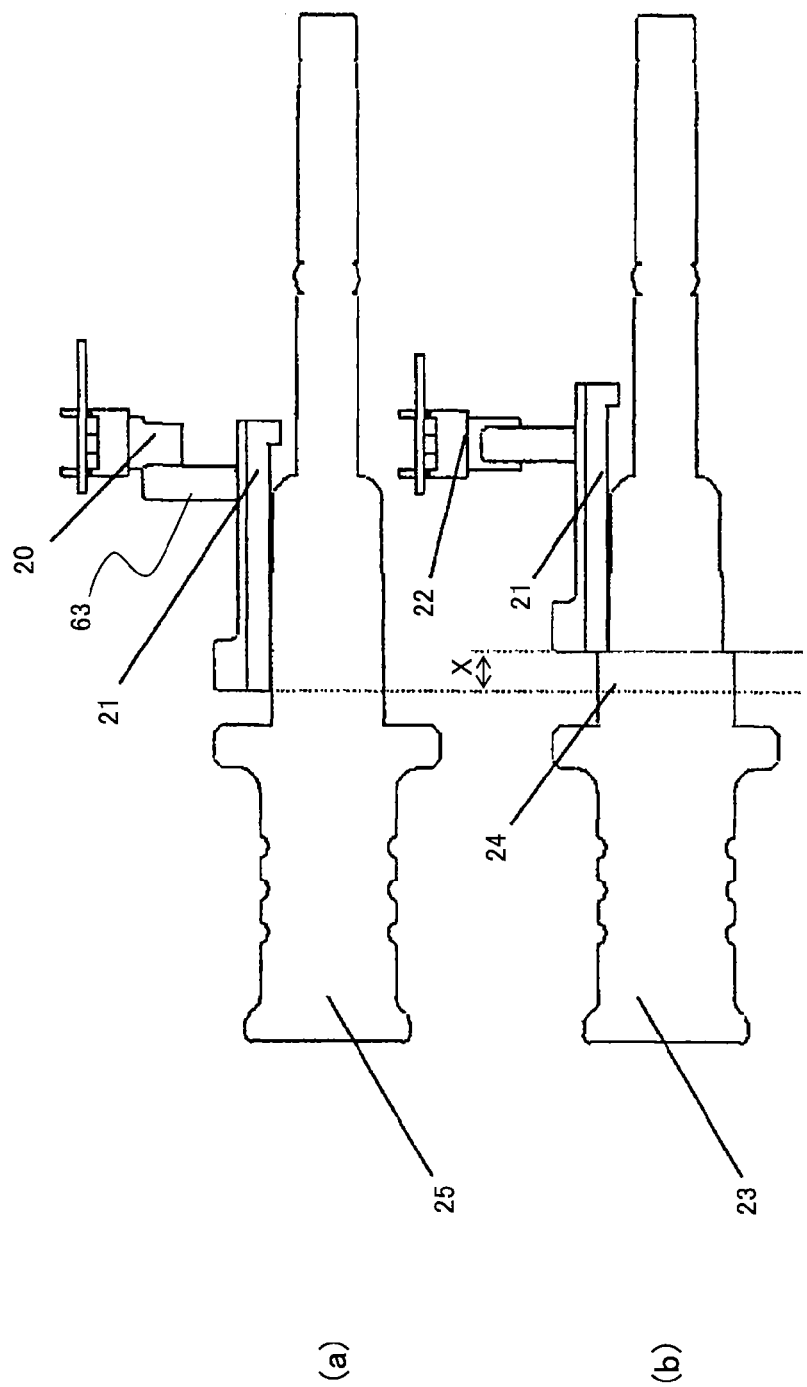
FIG. 7 shows diagrams explaining the relation between the light guide connector and the type identification means in embodiment 1 of the first mode.

FIG. 7 is a diagram explaining the relationship between the light guide connector and the type identification means in the present embodiment. With regard to the light guide connector shown in FIG. 7, FIG. 7(*a*) is the light guide connector 25 for low brightness and FIG. 7(*b*) is the light guide connector 23 for middle brightness. The light guide connector 25 for low brightness (hereinafter referred to as the low-brightness connector) in FIG. 7(a) is not provided with a flange configuration. Meanwhile, the light guide connector 23 for middle brightness (hereinafter referred to as the middle brightness connector) in FIG. 7(b) is provided with a flange unit 24. Given that the height dimension of the flange unit 24 is X, the height dimension of the flange unit 24 is determined by the position of the left end of the response moving member 21, that is, where the flange unit 24 has contact with the light guide connector, when the middle brightness connector 23 is connected from the position of the left end of the response moving member 21 when the light guide connector is not inserted.

Depending on the presence/absence of the flange unit 24, the position of the response moving member 21 when the low-brightness connector 25 is connected is different from when the middle brightness connecter 23 is connected by the height dimension X, as shown in FIG. 7. The height dimension X is set at the distance required when the low-brightness connector 25 moves from the initial position of the response moving member 21 shown in FIG. 7(a) to the position where a light-shielding unit 63 of the response moving member 21 falls within the sensing area of the optical sensor 20 shown in FIG. 7(b). Consequently, as shown in FIG. 7(a), when the low-brightness connector 25 is connected, the light-shielding unit 63 of the response moving member 21 is located outside the sensing area of the optical sensor 20, and the optical sensor 20 recognizes the state of "shielding object absent". When the middle brightness connector 23 is connected as in (b), the response moving member 21 is pushed in by the dimension X against the force of the spring in a state such that the end of the flange unit 24 (the right end in FIG. 7) is in contact with the end of the response moving member 21 (the left end in FIG. 7). Thus, the light-shielding unit 63 of the response moving member 21 is moved into the sensing area of the optical sensor 20, and the optical sensor 20 recognizes the state of "shielding object present". In such a manner, it is possible to identify the low-brightness connector 25 and the middle brightness connector 23 via the optical sensor 20 and the response moving member 21.

By the two identification means, the connection identification means consisting of the optical sensor 26 and the light-shielding spring 27 and the type identification means consisting of the optical sensor 26 and the response moving member 21, it is possible to distinguish the normal detection states of a case in which the low-brightness connector 25 is connected, a case in which the middle brightness connector 23 is connected, and a case in which the light guide connector is not connected.

FIG. 8A is a diagram showing combinations of the detection states of two optical sensors 20 and 26 when the light guide is normally connected in the present embodiment. "O" in FIG. 8A represents a case of the "shielding object present" state in the sensing area being determined by each of the optical sensors 20 and 26. At that time, in FIG. 4, a control unit not shown in the drawing receives a short signal. "X" represents a case of the "shielding object absent" state in the sensing area being determined for each of the optical sensors 20 and 26. At that time, the control unit receives an open signal. For example, when "shielding object present" is detected in the optical sensor 20 and "shielding object absent" is detected in the optical sensor 26, the combination of the detection states is represented as (O,X). The detection state of the two optical sensors when the light guide is not connected, the state when the low-brightness connector 25 is connected, and the state when the middle brightness connector 23 is connected are as follows.

(1) When the light guide connector is not connected, the combination is (X,O). The optical sensor 20 detects "shielding object absent", and the optical sensor 26 detects "shielding object present" due to the insulation sheet 32.

(2) When the low-brightness connector 25 of FIG. 7(a) is connected, the combination is (X,X). The optical sensor 20 remains as "shielding object absent" since the response moving member 21 does not move, and the optical sensor 26 detects "shielding object absent" due to the withdrawal of the insulation sheet 32.

(3) When the middle brightness connector 23 of FIG. 7(b) is connected, the combination is (O,X). The optical sensor 20 detects "shielding object present" since the response moving member 21 moves by the dimension X to the rear, and the optical sensor 26 detects "shielding object absent" due to the withdrawal of the insulation sheet 32.

As described above, from the combinations of the detection states of the two optical sensors it is possible to distinguish the state from among the following: the state in which the light guide connector is not connected, the state in which the low-brightness connector is connected, and the state in which the middle brightness connector is connected. On the basis of the combination of the detection states of the two optical sensors in FIG. 4, the control unit not shown in the drawing instructs the limiting means 18 to output the illuminating light with appropriate light intensity.

FIG. 8B is a diagram showing the detection states of the two optical sensors when the optical sensor 20 fails. Even if the middle brightness connector 23 is connected, the state cannot be recognized properly due to the failure of the optical sensor 20, and indicates a detection state identical to the state when the low-brightness connector 25 is connected (X,X). Even in such a case, the control unit of the light source device 1 causes the device to output illuminating light with a light intensity appropriate to the time when the low-brightness connector 25 is connected.

FIG. 8C is a diagram showing the detection states of the two optical sensors when the optical sensor 26 fails. Even if the light guide connector is not connected, the state cannot be recognized properly due to the failure of the optical sensor 26, and this indicates a detection state identical to the state when the low-brightness connector 25 is connected (X,X). Even in such a case, the illuminating light is shielded by the light-shielding spring 27, preventing the illuminating light from being leaked out of the light source device 1.

As explained with reference to FIG. 8, even when a failure occurs such as a disconnection of the optical sensor 20 or 26 or a connection terminal being pulled out, the light intensity output from the light source device 1 is appropriately limited on the basis of the change in the detection states of the optical sensors 20 and 26, and therefore, safety problems can be prevented.

It should be noted that in a case of failure caused by a loss of the insulation sheet 32 from the attached position, even though the light guide connector is not connected, the optical sensor 26 recognizes the state of "shielding object absent", and a detection state identical to that of FIG. 8C (X,X) can be obtained. Even when the light guide is not connected, the illuminating light is shielded by the light-shielding spring 27. For that reason, the illuminating light cannot leak out of the light source device 1.

Based on the combinations of the detection states of the two optical sensors of FIG. 8, the display on the operation panel of the light source device 1 can be switched FIG. 9 is an example of the operation panel of the present embodiment. A variety of setting switches 37 and a display LED 38 are arranged on the operation panel 36. As an example of the setting switches 37, a brightness switch 39 for setting the brightness, an air-supply/water-supply switch 41, and a transmission illumination switch 42, etc., are shown. As an example the display LEDs 38, a brightness display LED 40 and a transmission illumination display LED 43 are shown.

The brightness switch 39 is a switch for switching the illuminating light between the middle brightness and the low-brightness. The brightness switch 39 is used, for example, when connecting a surgical light guide with a tolerance to the middle brightness illuminating light. The air-supply/water-supply switch 41 is a switch for switching the air supply or water supply function ON and OFF. The transmission illumination switch 42 is a switch realizing a transmission illumination function, which is used when the position of the endoscope in a body cavity must be visually identified by irradiating with a high light intensity for a short time period. The air-supply/water-supply switch 41 and the transmission illumination switch 42 are used in a flexible scope for the digestive tract alone. Assume that the flexible scope for the digestive tract in this description is used at a low brightness.

Switching of the displays of the operation panel 36 in the present mode is explained with examples. When connecting the light guide of the flexible scope for a digestive tract used with low brightness, the unused brightness switch 39 is set to OFF and the brightness display LED 40 is turned off. The air-supply/water-supply switch 41 and the transmission illumination switch 42 are set to ON, and the transmission illumination display LED 43 is turned on.

For example, when connecting a light guide used with a middle brightness such as a surgical light guide, the brightness switch 39 is set to ON and the brightness display LED 40 is turned on. The unused air-supply/water-supply switch 41 and the transmission illumination switch 42 are set to OFF and the transmission illumination display LED 43 is turned off.

When the light guide connector is not connected, in order to reduce noise, pump driving in the light source device 1 is brought to a halt. In addition, under the assumption that none of the functions indicated by the setting switches 37 and display LED 38 on the operation panel 36 are to be used, all setting switches 37 are set to OFF and the display LED 38 is turned off.

As described above, according to the light source device of the present mode, type identification means for identifying the type of the light guide connected to the connector receiver unit and connection identification means for identifying whether or not the light guide is connected to the connector receiver unit are provided. Additionally, a light-shielding spring, which is an optical shielding means for preventing the illuminating light from the light source lamp from leaking out of the light source device when the light guide connector is not connected, is provided. By the type identification means and the connection identification means, the presence/absence of the connection of the light guide connector and the type of the connected light guide connector are identified. When the light guide connector is not connected, the illuminating light does not leak out due to the light-shielding spring, which is the optical shielding means. When the light guide connector is connected, the intensity is controlled so as to adjust to a safe light intensity based on the identification result.

The connection state of the light guide and the types of connected light guide connectors are determined by combining the identification result of each of the type identification means and the connection identification means. Therefore, with a failure in a single identification means, based on the combination of the identification result of the two identification means, it is possible to prevent the light guide from heat damage, and prevent the subject body from heat damage, and so on. Furthermore, in accordance with the type of the connected light guide connector, it is possible to realize a display on the operation panel that is operator-friendly and prevents operation errors.

(Second Embodiment)

The light source device of the present embodiment is to be explained. The present embodiment is different from the first embodiment in the following two ways: there are two optical sensors constituting the type identification means for identifying the type of the light guide connector; and there is a hinge constituting the light-shielding means for shielding illuminating light. The configuration of the optical system in the endoscope system and the light source device is the same as that of the system relating to the first embodiment; therefore, in this description the explanation of the configuration is omitted and the feature different from the first embodiment alone is explained.

Figure 10:
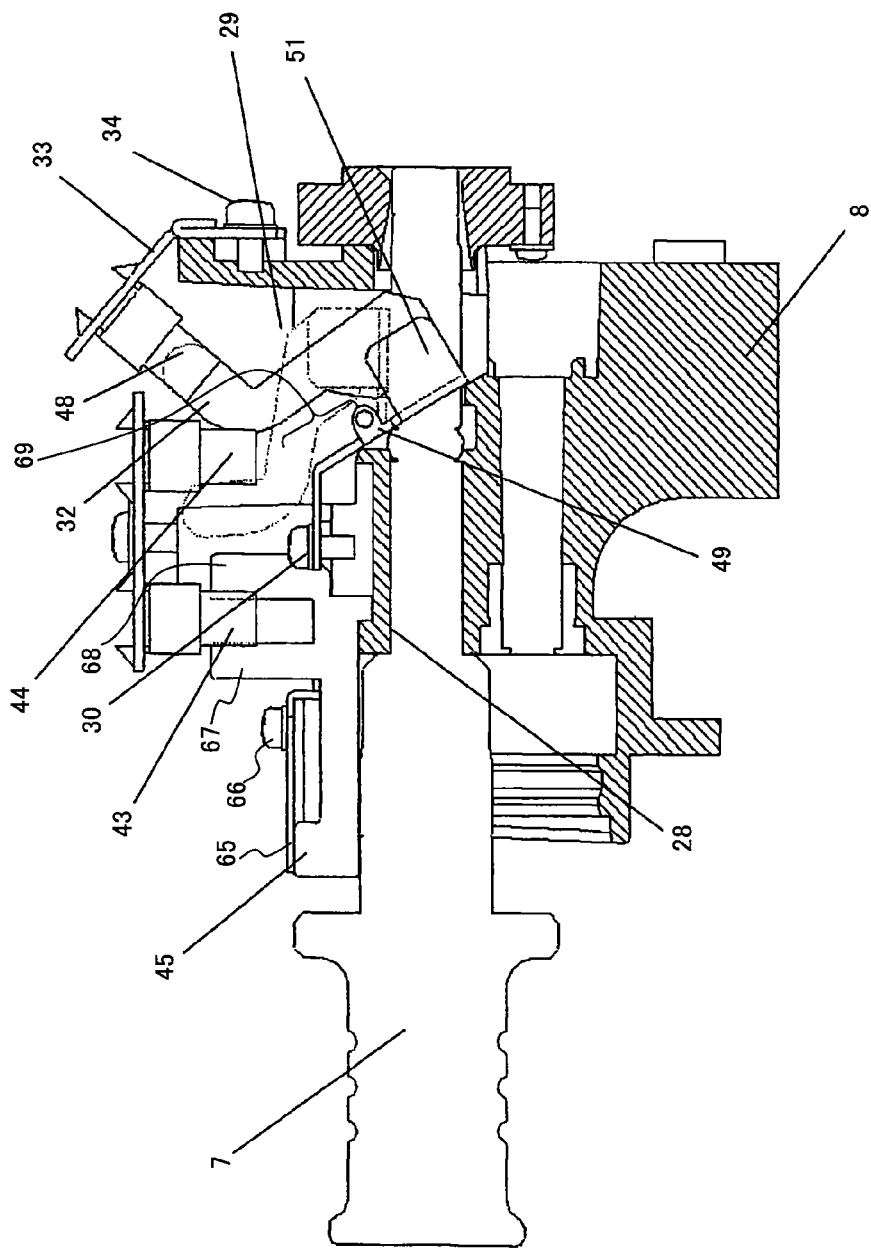
FIG. 10 is a cross-sectional diagram of the connector receiver unit of embodiment 2 of the first mode.

FIG. 10 is a cross-sectional diagram of the connector receiver unit of the light source device of the endoscope system relating to the present embodiment. The type identification means for identifying the type of the light guide connector comprises two optical sensors 43 and 44, and a response moving member 45. The connection identification means for identifying the presence/absence of the connection of the light guide connector comprises an optical sensor 48, a hinge 49, and a coil spring 50 (see FIG. 11). The response moving member 45 comprises two light-shielding units 67 and 68 in the present embodiment. The explanations of operations of the response moving member 45 and the light-shielding units 67 and 68 are omitted since they are the same as the response moving member 21 of the first embodiment. The hinge 49 and the coil spring 49 operate as light-shielding means.

Figure 11:
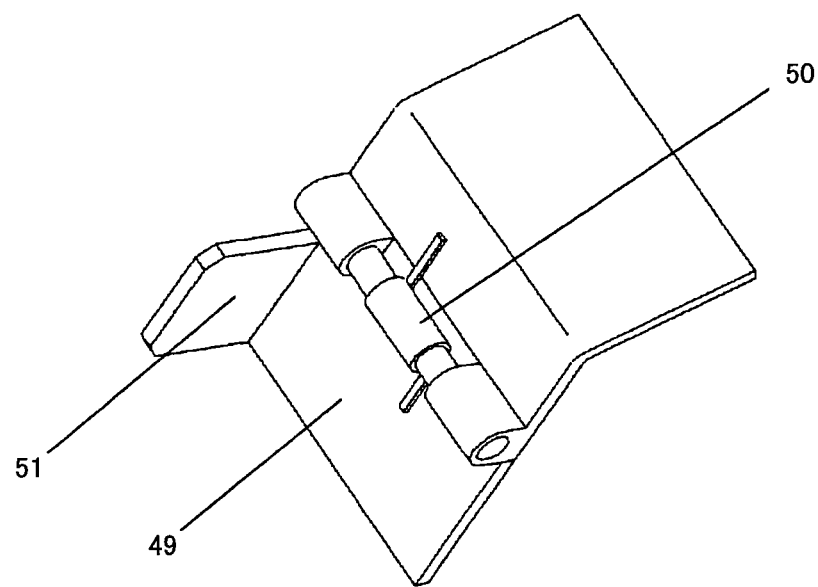
FIG. 11 is a diagram showing an example of the hinge and the coil spring of embodiment 2 of the first mode.

FIG. 11 is a diagram showing an example of the hinge and the coil spring. The hinge 49 is fixed by a setscrew 30 provided on the connector receiver unit 8 in an approximate cantilevered state. In addition, a force is applied to the hinge 49 to constantly press the slope 69 of the concave area 29 by the coil spring 50. When the light guide connector 22 is not connected, the hinge 49 covers the insertion hole 28. At that time, the detection state of the optical sensor 48 is "shielding object present" due to the insulation sheet 32 adhered on the upward bend 51 of the hinge 49.

The light guide connector 22 of the endoscope 2 is inserted into the insertion hole 28 of the connector receiver unit 8. By doing this, the hinge 49 is pushed obliquely upward by the tip of the light guide connector 22 at a low strength (see FIG. 10). The hinge 49 withdraws obliquely upward making an approximate arc trajectory around the axis that serves as a fulcrum. The tip of the insulation sheet 32 is, along with the obliquely upward withdrawal movement of the hinge 49, pushed by the upward bend 51 of the hinge 49 and moves obliquely upward.

The amount of movement of the insulation sheet 32 is set larger than the sensing area of the optical sensor 48. When the light guide connector 22 is not connected, the insulation sheet 32 is located in the sensing area of the optical sensor 48. When the light guide connector 22 is connected, the insulation sheet 32 is withdrawn to outside of the sensing area. Then, by the movement of the insulation sheet 32 in the optical sensor 48, the detection state becomes "shielding object absent" as the shielding object is not present in the sensing area.

Figure 12:
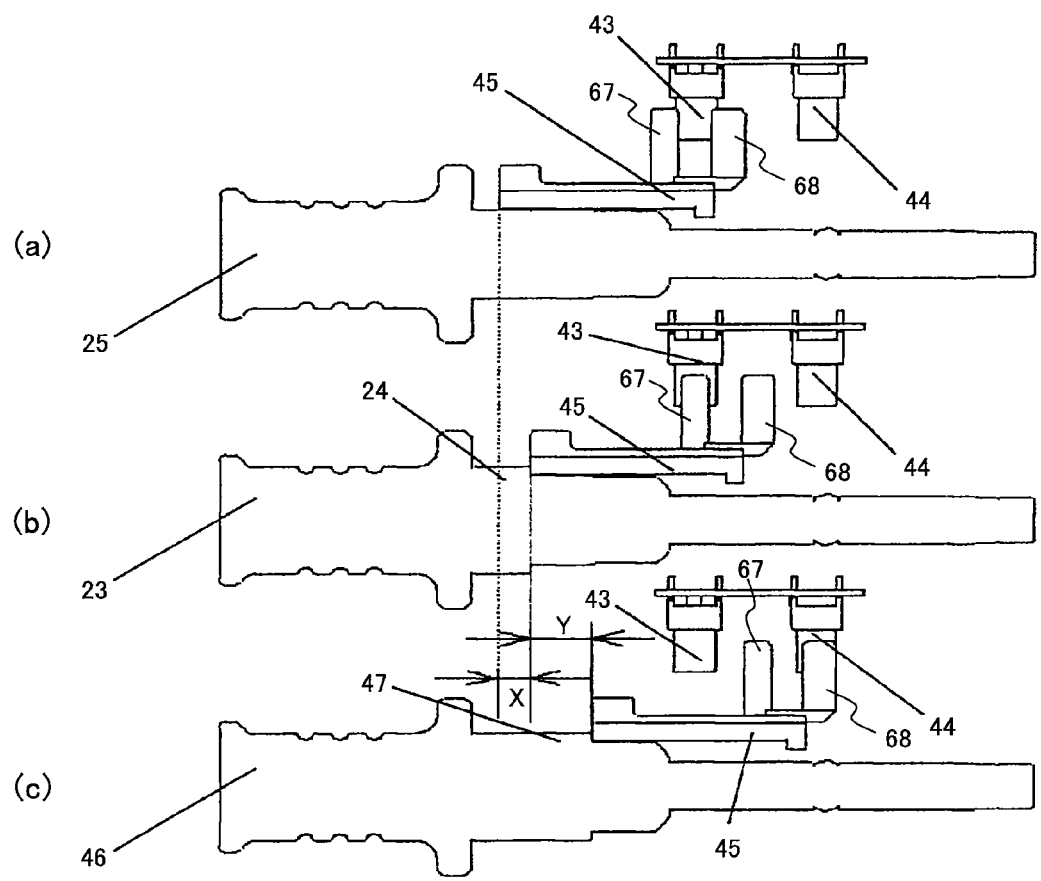
FIG. 12 shows diagrams explaining the relation between the light guide connector and the type identification means in embodiment 2 of the first mode.

FIG. 12 is a diagram explaining the relationship between the light guide connector and the type identification means in the present embodiment. Among the light guide connectors in FIG. 12, FIG. 12(a) is a light guide connector 25 for low brightness, FIG. 12(b) is a light guide connector 23 for middle brightness 23, and FIG. 12(c) is a light guide connector 46 for high-brightness. Similarly to the first embodiment, the light guide connector 25 for low brightness (hereinafter referred to as the low-brightness connector) of (a) is not provided with a flange configuration; however, the light guide connector 23 for middle brightness (hereinafter referred to as the middle brightness connector) of (b) is provided with a flange unit 24 with the height dimension being X. The light guide connector 46 for high-brightness (hereinafter referred to as a high-brightness connector) of (c) is provided with a flange unit 47 with the height dimension being X+Y.

When inserting the light guide connector into the insertion hole 28, the location of the response moving member 45 varies depending on the presence/absence of the flange configuration and the height dimension of the flange unit. In (a), it is not located in any of the sensing areas of the two optical sensors 43 and 44 constituting the type identification means. In (b), the light-shielding unit 67 of the response moving member 45 is within the sensing area of the optical sensor 43 located on the near side of the insertion entry point of the light guide connector. In (c), the light-shield unit 68 of the response moving member 45 is within the sensing area of the optical sensor 44.

The connection state of the light guide connector can be classified by the combination of the detection states of the optical sensors 43, 44, and 48. For example, when the optical sensor 43 detects "shielding object absent", the optical sensor 44 detects "shielding object present", and the optical sensor 48 detects "shielding object absent", it is represented as (X, O, X).

FIG. 13A is a diagram showing combinations of the detection states of the three optical sensors 43, 44 and 48 when a light guide is connected normally in the present embodiment. The definitions of "O" and "X" in FIG. 13A are the same as those in the first embodiment.

In FIG. 13A, the combinations of the detection states of the three optical sensors 43, 44 and 48 are, regarding the connection state of the light guide connector, all different depending on whether the state is unconnected, low-brightness connector connected, middle brightness connector connected, or high-brightness connector connected, respectively represented by (X, X, O), (X, X, X), (O, X, X), or (X, O, X). Therefore, on the basis of the combination of the detection state of the three optical sensors, it is possible to determine the connection state of the light guide connector.

FIG. 13B is a diagram showing the combinations of the detection states of the three optical sensors when the optical sensor 43 fails in the present embodiment. When the optical sensor 43 cannot correctly detect the presence/absence of the shielding object, even in the state in which the middle brightness connector is connected, the detection state shows (X, X, X), which is the same as the detection state when the low-brightness connector is connected, due to incorrect sensing. On the basis of the detection state of the optical sensor, even if the middle brightness connector is actually connected, the light intensity of the illuminating light is adjusted to the light intensity appropriate for the time when the low-brightness connector is connected by limiting means 18 of FIG. 4.

FIG. 13C is a diagram showing the combinations of the detection states of the three optical sensors when the optical sensor 44 fails in the present embodiment. The connection state of the high-brightness connector cannot be correctly sensed, even in a state in which the high-brightness connector is actually connected, the detection state is (X, X, X), which is incorrect in that it indicates that a low-brightness connector is connected. Since the light intensity of the illuminating light is based on the detection state of the optical sensors, when a high-brightness connecter is connected, the light intensity is adjusted to the intensity it would be if a low-brightness connector were connected by the limiting means 18 of FIG. 4.

FIG. 13D is a diagram showing combinations of detection states of the three optical sensors when the optical sensor 48 fails. If the presence/absence of the connection of the light guide connector cannot be sensed correctly, the detection state is (X, X, X) even if the light guide connector is not connected; this state is incorrect in that it indicates that a low-brightness connector is connected. In such a case, the illuminating light is shielded by the hinge 49 and cannot leak out of the light source device 1.

FIG. 14A-14B is a diagram showing combinations of the detection states of the three optical sensors when the response moving member 45 of the light source device 1 is fixed on the flange unit of the light guide connector. Being fixed in the description means a state in which the elastic force of a spring etc. that gives force to the response moving member 45 is no longer effective, and the response moving member cannot move freely, staying in a particular position even with the insertion or ejection of a light guide connector.

Assume that when connected to the high-brightness connector, the response moving member 45 is fixed on the flange unit 47 of the connector. FIG. 14A is a diagram showing the combinations of the detection states of the three optical sensors when the response moving member is fixed at the position of the flange unit 47 and a high-brightness connector is connected. Because it is fixed during the high-brightness connector 46 connection, even in the state in which the light guide connector is not connected after ejecting the high-brightness connector 46, the optical sensor 44 still senses the state of "shielding object present", and the detection state changes from (X, O, X), which is the high-brightness connector connected state, to (X, O, O).

The control unit, which receives a signal of the state (X, O, O) when the light guide connector is not connected, recognizes that a failure is occurring with regard to the state of the connector receiver unit 8 of the light source device, and switches the operation mode to "failure mode". In failure mode, the illuminating light is adjusted to have a low light intensity as in the low-brightness connector connection, and the operator is notified of failure occurrence via a flashing display etc. on the operation panel 36 of FIG. 9.

When the response moving member 45 is fixed at a position of the flange unit 47 of the connector and the high-brightness connector is connected, the low-brightness connector 25 or the middle brightness connector 23 may be connected by mistake after ejecting the high-brightness connector 46. In such a case, the detection state is (X, O, X), which is the same as the case of connecting the high-brightness connector in a normal state. However, since the operation mode has been previously switched to the failure mode, the light intensity output is the same as the light intensity when the low-brightness connector 25 is connected, and illuminating light with a high light intensity cannot be output from the light source device 1.

FIG. 14B is a diagram showing the combinations of the detection states of the three optical sensors when the response moving member 45 is fixed at the flange unit 24 and when connected to the middle brightness connector. Because it is fixed when the middle brightness connector 23 is connected, the optical sensor 43 senses the state of "shielding object present" and the detection state is changed from (O, X, X) to (O, X, O), even in the state in which the light guide connector is not connected after ejecting the middle brightness connector 23.

The control unit, which receives a signal of the state (O, X, O) when the light guide connector is not connected, recognizes a failure occurring with regard to the state of the connector receiver unit 8 of the light source device, and switches the operation mode to "failure mode". In failure mode, the illuminating light is adjusted to have a low light intensity as when the low-brightness connector is connected, and the operator is notified of a failure occurrence via a flashing display etc. on the operation panel 36 of FIG. 9.

Assume that the response moving member 45 is fixed, when connecting to the middle brightness connector, at the position of the flange unit 24 of the connector. After ejecting the middle brightness connector, the low-brightness connector 25 may be connected by mistake. Since the response moving member 45 is fixed, the detection state is (O, X, X), which is the same state as when the middle brightness connector is connected in a normal state. However, after ejecting the middle brightness connector 23, the fixing of the response moving member 45 is recognized, and the operation mode is switched to the failure mode. Consequently, in a case of the low-brightness connector connection being incorrectly sensed as the middle brightness connector connection since the response moving member 45 is fixed, the light intensity is adjusted to the light intensity of the low-brightness connector 25 connection, and illuminating light with a high light intensity cannot be output from the light source device 1.

Similarly, a case is examined in which, after the response moving member 45 is fixed, the middle brightness connector 23 is ejected and the high-brightness connector 46 is connected when connecting to the middle brightness connector at the position of the flange unit 24. The response moving member 45 is, even in the fixed state, forcibly moved toward the right in FIG. 10 by the high-brightness connector 46. The detection state of the three optical sensors is (X, O, X), which is the same as the state that exists when connecting the high-brightness connector in the normal state. In such a case, since the fact that the response moving member 45 is fixed is recognized when ejecting the middle brightness connector 23 and since the operation mode has been switched to the failure mode, illuminating light with a high light intensity cannot be output from the light source device 1.

In response to the failure caused by the loss of the insulation sheet 32, the same processing is performed as in the case of failure in the optical sensor 48 explained with reference to FIG. 13D.

In the present embodiment, the display on the operation panel of the light source device 1 can be switched based on the combination of the detection state of the three optical sensors. Similarly to the previous embodiment, the operation panel 36 of FIG. 9 is used, for example. The types of switches 37 and the display LED 38 arranged on the operation panel 36 are the same as those of the first embodiment.

A brightness switch 39 is a switch for switching the illuminating light to high-brightness or to low brightness, and is used when connecting a surgical light guide with a tolerance against the high-brightness illuminating light. An air-supply/water-supply switch 41 is a switch for switching ON/OFF the air supply or water supply function. A transmission illumination switch 42 is a switch realizing a transmission illumination function, which is used when the position of the endoscope in a body cavity is visually confirmed with by irradiating the body cavity with a high light intensity for a limited time period. The air-supply/water-supply switch 41 and the transmission illumination switch 42 are used only in a flexible scope for digestive tracts. Assume that the flexible scope for digestive tracts in this description is used at a middle brightness.

The switching of the display on the operation panel 36 in the present embodiment is explained with an example. When connecting the light guide of the flexible scope (used at a middle brightness) for use in a digestive tract, the brightness switch 39 is set to OFF and the brightness display LED 40 is turned off. The air-supply/water-supply switch 41 and the transmission illumination switch 42 are set to ON, and the transmission illumination display LED 43 is lit.

When connecting a light guide used with high-brightness such as a surgical light guide, the brightness switch 39 is set to ON and the brightness display LED 40 is lit. The air-supply/water-supply switch 41 and the transmission illumination switch 42, which are not to be used, are set to OFF, and the transmission illumination display LED 43 is turned off.

In the state of the light guide used with low brightness being connected or the light guide not being connected, pump driving in the light source device 1 is stopped in order to reduce noise. In addition, since none of the functions indicated by the setting switch 37 and the display LED 38 on the operation panel 36 are used, all the setting switches 37 are set to OFF and the display LED 38 is turned off.

As explained above, according to the light source device of the present embodiment, the type identification means for identifying the type of the connected light guide connector comprises two optical sensors. Identification of more types of light guide connectors in addition to a low-brightness connector, a middle brightness connector and a high-brightness connector becomes possible. The light-shielding means for preventing the illuminating light from leaking outside of the light source device when the light guide connector is not connected is configured with a hinge. When the light guide connector is inserted, the upward bend of the hinge moves, making an approximate arc trajectory. By using the hinge, a stable trajectory can be obtained without making clearance in consideration of the variation of the trajectory. Therefore, it is possible to realize a small light source device for an endoscope.

Note that the present embodiment employs three optical sensors and a hinge; however, these do not limit the invention. For example, the use of a hinge as the light-shielding means in the light source device of the first embodiment, or the use of a light-shielding spring as the light-shielding means in the light source device of the present embodiment, are also possible. Regarding the number of optical sensors, the above first and second embodiments of the light source device use two or three; however, the number of provided sensors may be larger than two or three.

Additionally, the present invention is not limited to the above-described embodiments, but various modifications may be made for its implementation.

The light source device for an endoscope of the present embodiment comprises a light source lamp for generating illuminating light, a connector receiver to which the light guide connector of an endoscope is detachably connected, connection identification means for determining whether or not the light guide connector is connected to the connector receiver, type identification means for identifying the type of the light guide connector connected to the connector receiver, and a control unit for controlling based on the identification result of the connection identification means and the type identification means.

In the above light source device for an endoscope, the control unit can set the light intensity of the light source lamp.

Additionally, the light source device for an endoscope further comprises light-shielding means, arranged on an optical path of the illuminating light emitted from the light source lamp, for shielding the illuminating light from the connector receiver when the light guide connector is not connected.

In the light source device for an endoscope, the light-shielding means is movable between the first position, shielding the illuminating light from the connector receiver when the light guide connector is not connected, and the second position, where the light-shielding means withdraws from the first position when the light guide connector is connected, and the connection identification means detects whether the light-shielding means is located at the first position or in the second position. When detecting that the light-shielding means is located at the first position, it is determined that the light guide connector is not connected to the connector receiver, and when detecting that the light-shielding means is located at the second position, it is determined that the light guide connector is connected to the connector receiver.

In the light source device for an endoscope, the type identification means that is movable along the direction of the light guide connector inserted into/ejected from the connector receiver comprises a response moving member moving to a position in accordance with the type of light guide connector connected to the connector receiver and detection means for detecting the position to which the response moving member has moved, and determines the type of light guide connector connected to the connector receiver based on the position of the response moving member detected by the detection means.

In the light source device for an endoscope, the light-shielding means is configured with an elastic member.

In the light source device for an endoscope, the light-shielding means is configured with a hinge.

In the light source device for an endoscope, the control unit switches the setting switch to the display unit of the light source device for an endoscope on the basis of the identification result of the connection identification means and the type identification means.

As described above, according to the present embodiment, it is possible to determine the presence/absence of the light guide connector connection and the type of connected light guide connector. The illuminating light can be adjusted to an appropriate light intensity in accordance with the connection state of the light guide connector.

<Second Mode>

Every endoscope has the maximum allowable light intensity that can enter the endoscope inlet end determined in accordance with its intended use, such as for internal medicine or surgical use. For that reason, the light source device is required to automatically control the maximum light intensity to be supplied in accordance with the type of endoscope, and is also required to have a neutral density filter adopted to the type of endoscope.

However, when the maximum allowable light intensity of a common surgical endoscope is "1", for example, the intensity varies such that a surgical endoscope with high-brightness has twice as much, and an internal medicine endoscope with a high-brightness has 1.3-1.6 times as much; a neutral density filter is thus required for darkening.

If all of the neutral density filters, an optical filter, and a special light filter are provided on the turret plate of the observation mode switching turret, the turret will become large, resulting in the entire device having a large size.

Every endoscope has a different setting content in accordance with its type, e.g., internal medicine or surgical use. For example, a flexible endoscope is provided with an air-supply channel and can supply air from an air pump provided in the light source device. On the other hand, since a rigid endoscope does not contain an air-supply channel, air cannot be supplied from the air pump provided in the light source device.

For that reason, for the light source device that is connected to a flexible endoscope and that supplies air from an air pump, if the flexible endoscope is removed and a rigid endoscope is connected, the air pump remains running. In this case, the air pump in the light source device must be turned off manually.

Accordingly, the conventional light source device requires changes in settings to be made by the user him/herself in accordance with the connected endoscope, which is an inconvenience.

In the present mode, a downsized light source device, despite comprising various optical filters, filters for special observation, and neutral density filters, is explained. In the present mode, additionally, a light source device that can change the setting automatically in accordance with the type of connected endoscope is explained. In the following description, details of the embodiment of the present invention are set forth first.

Figure 15:
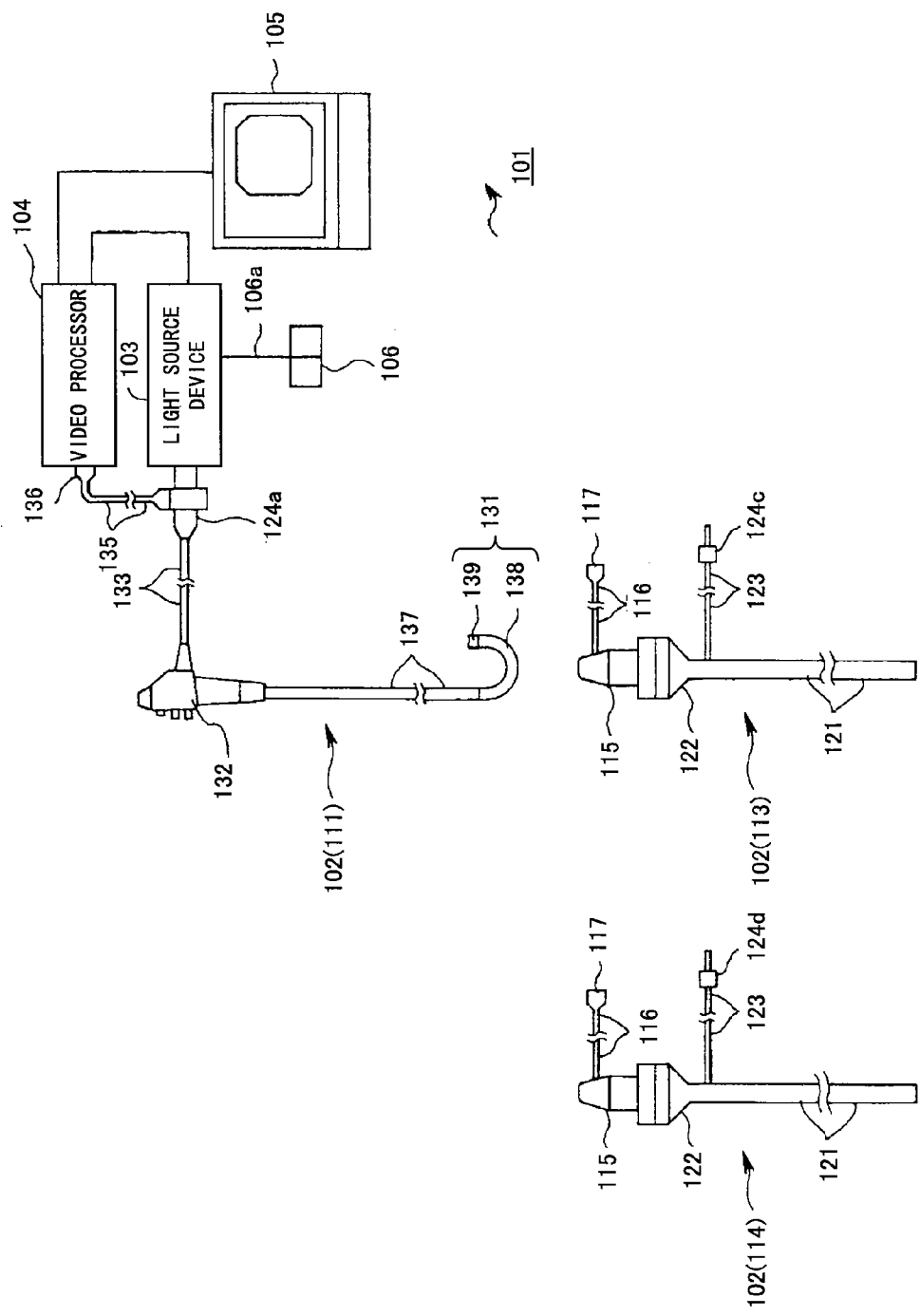
FIG. 15 is a diagram showing the entire configuration of an endoscope system comprising the light source device for an endoscope of the second mode.

FIG. 15 is a diagram showing the configuration of an entire endoscope system comprising the light source device for an endoscope of the present mode. An endoscope system 101 comprises a plurality of types of endoscopes 102, a light source device for an endoscope (hereinafter referred to as a light source device) 103, a video processor 104, and a monitor 105. Note that a foot switch 106 is to be connected to the light source device 103.

The plurality of types of endoscopes 102 comprises a normal flexible endoscope 111, a normal rigid endoscope 113, and a high-brightness rigid endoscope 114.

A camera head 115 is installed in each of the normal rigid endoscopes 113 and the high-brightness rigid endoscope 114. An electrical connector 117 is provided at the end of a camera cable 116 extended from the camera head 115. The electrical connector 117 is detachably connected to the video processor 104. Note that an image pickup device for picking up endoscopic images supplied from the normal rigid endoscope 113 and the high-brightness rigid endoscope 114 is embedded in the camera head 115, although it is not shown in the drawing.

The normal rigid endoscope 113 and the high-brightness rigid endoscope 114 are provided with an insertion unit 121 and an eyepiece 122. The insertion unit 121 is inserted into the abdominal cavities of a patient via a trocar not shown in the drawing. The eyepiece 122 is connected serially to the proximal end of the insertion unit 121.

The normal rigid endoscope 113 is provided with a light source connector 124c on the end of a light guide cable 123 extending from the eyepiece 122. A light source connector 124c is provided. The light source connector 124c is detachably connected to the light source device 103. The high-brightness rigid endoscope 114 is provided with a light source connector 124d on the end of the light guide cable 123 extending from the eyepiece 122. The light source connector 124d is detachably connected to the light source device 103.

The normal flexible endoscope 111 comprises an insertion unit 131 and an operation unit 132. The insertion unit 131 is a long and thin section inserted into body cavities. The operation unit 132 is a part serially connected to the proximal end of the insertion unit 131.

The normal flexible endoscope 111 is provided with a light connector 124a on the end of a universal cable 133 extended from the operation unit 132. The light source connector 124a is detachably connected to the light source device 103.

An electrical cable 135 is extended from the side of the light source connector 124a. An electrical connector 136 is attached to the end of the electrical cable 135. The electrical connector 136 is detachably connected to the video processor 4.

The insertion unit 131 comprises a bendable tube unit 137, a bent section 138 and a distal end 139. The bendable tube unit 137 is flexible. The bent section 138 is attached to the distal end side of the bendable tube unit 137. The distal end 139 is attached to the distal end of the bent section 138. The distal end 139 is installed with an image pickup device, as explained later, for picking up images of an observation target in body cavities. Note that in FIG. 15 the normal flexible endoscope 111 is connected to the light source device 103 and the video processor 104.

Figure 16:
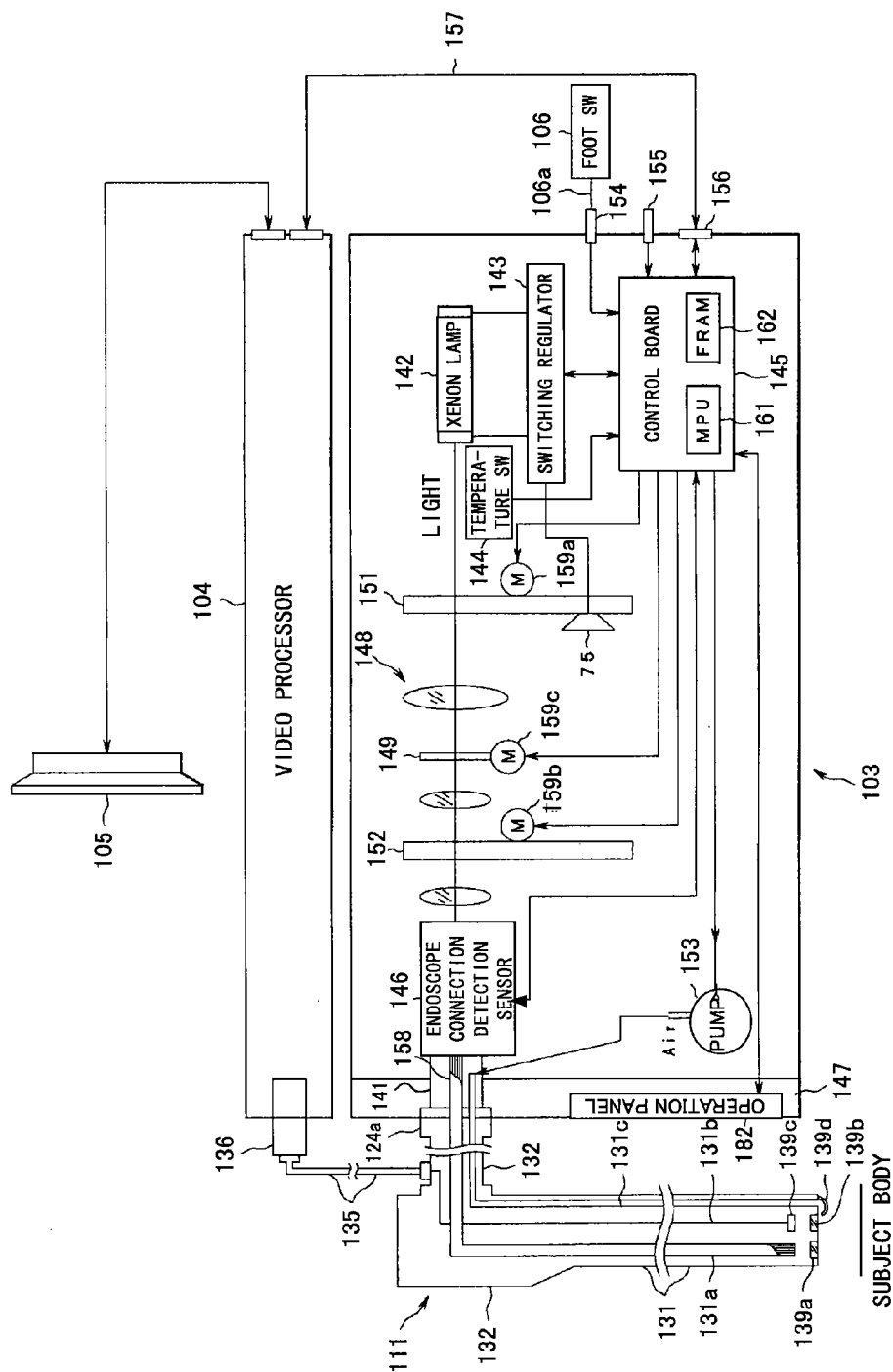
FIG. 16 is a block diagram showing the inner configuration of the light source device of FIG. 15.

FIG. 16 is a block diagram showing the inner configuration of the light source device of FIG. 15. The normal flexible endoscope 111 has a light guide 131a inserted and set. Since the light source connector 124a is detachably connected to the light source device 103, the light guide 131a can supply the illuminating light.

The illuminating light supplied from the light source device 103 is transmitted to the distal end of the insertion unit 131 by the light guide 131a. The illuminating light transmitted to an output end face of the light guide 131a is for illuminating the observation target part of the subject body from an illumination optical system 139a provided in the end face.

An objective optical system 139b is set on the distal end 139 of the insertion unit 131. The objective optical system 139b is adjacent to the illumination optical system 139a, and is for capturing the light from the observation target part and for forming optical images. A CCD 139c is provided as an image pickup device in the back of the objective optical system 139b.

A signal line 131b is extended from the CCD 139c. The signal line 131b is inserted through the insertion unit 131, runs through the electrical cable 135, and reaches the electrical connector 136. Therefore, the signal line 131b is electrically connected to the video processor 104 via the electrical connector 136.

The CCD 139c is driven by a driving signal output from a CCD driving circuit, not shown in the drawing, provided in the video processor 104. The CCD 139c generates an image pickup signal by performing optoelectrical conversion of the formed optical images, and the image pickup signal is output to the video processor 104.

The video processor 104 processes the image pickup signal output from the CCD 139c by an image signal processing circuit not shown in the drawing, and generates a standard image signal. The video processor 104 outputs the image signal to a monitor 105 and causes the monitor 105 to display the image on the display screen.

In addition, the normal flexible endoscope 111 has an air-supply channel 131c inserted and set. Since the light source connector 124a is detachably connected to the light source device 103, the air-supply channel 131c can supply the air.

The air provided from the light source device 103 is supplied to the distal end side of the insertion unit 131 by the air-supply channel 131c. The air supplied to the output end face of the air-supply channel 131c is supplied toward the most distal end side of the objective optical system 139b from a nozzle 139d provided on the surface of the end face.

The light guide 131a, the illumination optical system 139a, and the objective optical system 139b in both the normal rigid endoscope 113 and the high-brightness rigid endoscope 114 have the same configuration. Note that since the normal rigid endoscope 113 and the high-brightness endoscope 114 are provided with an image transmission optical system such as a relay lens system in the posterior of the objective optical system 139b (not shown in the drawing), optical images can be transmitted to the eyepiece 122.

Next, the light source device 103 is set forth.

The light source device 103 comprises a connector receiver unit 141 as an endoscope connection unit, a xenon lamp 142 as a light source, a switching regulator 143, a temperature switch 144, a control board 145, an endoscope connection detection sensor 146, a front panel 147, an optical system 148, a diaphragm 149, an observation mode switching turret 151, a neutral density mesh turret 152, an air-supply pump (hereinafter referred to as the pump) 153, a foot-switch connection unit 154, an automatic/manual lighting switching switch 155, and a communication connector 156.

One of the light source connectors 124a, 124c or 124d of the endoscope 102 (the normal flexible endoscope 111 with two types of maximum light intensity able to be set, the normal rigid endoscope 113, and the high-brightness rigid endoscope 114) is selectively detachably connected to the connector receiver unit 141.

The connector receiver unit 141 is provided with the endoscope connection detection sensor 146. The endoscope connection detection sensor 146 detects the type of connected endoscope 102. The endoscope connection detection sensor 146 is configured with, for example, three photosensors, first through third, explained later. Note that the configuration of the endoscope connection detection 146 is set forth in detail later.

At this point, the setting content of the light source device 103 varies in accordance with the type of endoscope 102 (normal flexible endoscope 111, normal rigid endoscope 113, or high-brightness endoscope 114).

For example, since a normal flexible endoscope 111 is provided with the above-explained air-supply channel 131c, it is possible to supply the air via the pump 153 of the light source device 103. On the other hand, the normal rigid endoscope 113 and the high-brightness rigid endoscope 114 have a configuration in which the pump 153 is not used because the air supply is unnecessary.

Additionally, in the endoscope 102 (normal flexible endoscope 111, normal rigid endoscope 113, or high-brightness rigid endoscope 114), the maximum light intensity of the illuminating light that can be entered is determined in accordance with the type.

The present embodiment has a configuration in which the type of endoscope 102 (normal flexible endoscope 111, normal rigid endoscope 113, or high-brightness rigid endoscope 114) connected to the light source device 103 is detected, and the light source device 103 is automatically set. In addition, the present embodiment has a configuration in which the maximum light intensity of the illuminating light supplied is automatically set in accordance with the type of endoscope 102 connected to the light source device 103.

The xenon lamp 142 is a lamp utilizing electrical discharge in xenon gas. The spectrum of the xenon lamp 142 is similar to natural sunlight, and therefore natural light illumination (high illumination intensity) light can be obtained.

The switching regulator 143 is a power source stabilizer adopted a method for converting input voltage into pulses by switching between ON and OFF at a high speed and for obtaining smoothed and stable DC voltages. The switching regulator 143 converts input voltage supplied from the control board 145 into DC voltage and supplies the voltage to each part of the device.

The temperature switch 144 is provided in proximity to the xenon lamp 142. The temperature switch 144 turns ON when the temperature around the xenon lamp 142 reaches a prescribed value and outputs an ON signal to the control board 145. By exchanging signals, the control board 145 can turn OFF the xenon lamp 142.

The automatic/manual lighting switching switch 155 is a switch that allows the selection of automatic or manual lighting of the xenon lamp 142 when the power of the light source device 103 is ON.

Connected to the communication connector 156 is a communication cable 157 of the video processor 104.

The optical system 148 comprises a lens group for collecting the light generated by the xenon lamp 142 in the input end face of the light guide 158. The light guide 158 is connected to selected one of the light source connectors 124a, 124b and 124d, and projects from the selected light source connector.

The observation mode switching turret 151, the neutral density mesh turret 152, and the diaphragm 149 are provided on an optical path comprising this lens group.

Each of the turrets 151 and 152 and the diaphragm 149 is provided with motors 159a, 159b, and 159c, respectively.

Figure 22:
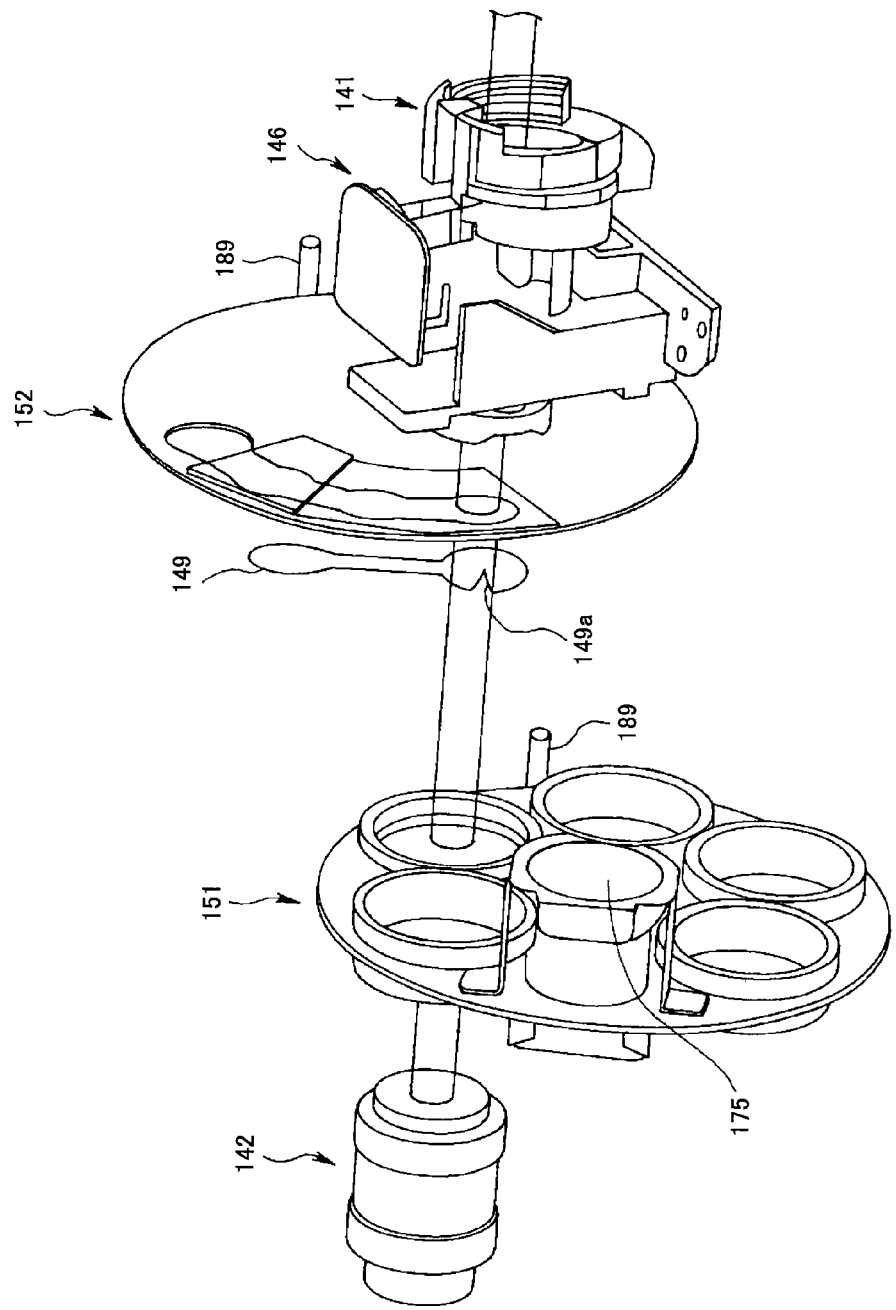
FIG. 22 is a schematic perspective view showing an optical path from the xenon lamp of FIG. 2.

The diaphragm 149 has a formation of a fan-shaped concavity 149a (see FIG. 22). The diaphragm 149 can limit the illuminating light to a desired light intensity by moving the position of the fan-shaped concavity 149a on the optical path by driving the motor 159c.

In the observation mode switching turret 151 and the neutral density mesh turret 152, a desired filter is set on the optical path by driving the motors 159a and 159b. The configurations of the observation mode switching turret 151 and the neutral density mesh turret 152 are given in detail later.

A foot switch cable 106a for the foot switch 106 is connected to the foot switch connection unit 154. The front panel 147 can have various settings and show various displays. Details of the configuration of the front panel 147 are given later.

The pump 153 can supply air to the normal flexible endoscope 111. The air from the pump 153 is supplied from the connector receiver unit 141 to the normal flexible endoscope 111 via a channel not shown in the drawing.

The control board 145 comprises an MPU (Micro Processing Unit) 161, FRAM (Ferroelectric Random Access Memory) 162, and ROM (READ Only Memory) or SRAM (Static Random Access Memory); the ROM and SRAM are not shown in the drawing.

The MPU (Micro Processing Unit) 161 is for controlling each of the units in the device. The ROM or SRAM is for storing programs of the MPU 161. The FRAM 162 is for storing data being run.

It should be noted that the FRAM 162 stores the settings of the light source device 103 in advance according to the type of endoscope 102 connected, as explained later. The settings are rewritable.

FIG. 17 is a block diagram showing an inner configuration of the control board of FIG. 16. The control board 145 comprises, in addition to the MPU 161 and the FRAM 162, an observation mode switching turret control unit 63, a neutral density mesh turret control unit 164, a diaphragm control unit 165, an endoscope connection detection unit 166, a pump control unit 167, a lamp lighting control unit 168, a temperature switch detection unit 169, a foot switch detection unit 171, a communication control unit 172, an automatic/manual lighting switch control unit 173, and a front panel control unit 174. The above control units are controlled by the MPU 161.

The observation mode switching turret control unit 163 controls the motor 159a to set a desired optical filter of the observation mode switching turret 151 on the optical path.

Note that the observation mode switching turret 151 is provided with a spare halogen lamp 175 in case the xenon lamp 142 goes out.

When the xenon lamp 142 goes out, the observation mode switching turret control unit 163 provides light to the endoscope 102 by driving the motor 159a of the observation mode switching turret 151 so that the spare halogen lamp 175 is set on the optical path.

The neutral density mesh turret control unit 164 controls the motor 159b to set a desired filter of the neutral density mesh turret on the optical path.

The diaphragm control unit 165 controls the motor 159c for adjusting the position of the diaphragm 149 so that the illuminating light from the xenon lamp 142 has the desired light intensity.

In the present embodiment, if the light source connectors (124a, 124c, 124d) of the endoscope 102 are pulled out of the connector receiver unit 141, the communication cable 157 is pulled out, a failure occurs in the endoscope connection detection unit 166, or the power of the video processor 104 is off, the diaphragm 149 is controlled so as to have a prescribed opening.

By doing this, the light intensity of the illuminating light required for medical treatment can be maintained without totally closing the diaphragm 149 even when the endoscope connection detection unit 166 detects incorrectly due to a failure or when the communication cable 157 is disconnected or pulled out of the light source device 103 during a medical examination.

Note that the connector receiver unit 141 has a configuration in which, when the light source connectors (124a, 124c, 124d) are not connected, an opening/closing member (the flexible member 206 in FIG. 32, explained later) prevents unintended illuminating light from leaking out.

The endoscope connection detection unit 166 detects the ON/OFF signal from the endoscope connection detection sensor 146 and outputs it to the MPU 161.

The pump control unit 167 controls and drives the pump 153.

The temperature switch detection unit 169 detects the ON signal from the temperature switch 144 and outputs it to the MPU 161.

The foot switch detection unit 171 detects the ON/OFF signal of the foot switch 106 and outputs it to the MPU 161.

The communication control unit 172 controls communications between the video processor 104 etc. and the MPU 161.

The lamp lighting control unit 168 controls the lighting of the xenon lamp 142.

The automatic/manual lighting switching control unit 173 detects the signal from the automatic/manual lighting switching switch 155 and outputs the signal to the MPU 161.

Here, when the power is turned on in conventional light source devices, lighting is automatic in endoscopes for surgery (rigid endoscopes) and lighting is manually controlled in endoscopes for internal medicine (flexible endoscope) because the usage environments are different.

In the present embodiment, either automatic lighting or manual lighting of the xenon lamp 142 is possible in accordance with the user usage environment when the power of the light source device 103 is turned ON.

In other words, if the automatic/manual lighting switching switch 155 is pressed by a user in advance and is set to the automatic setting, the xenon lamp 142 automatically lights upon start-up when the power is turned on. In addition, with the manual setting the automatic/manual lighting switching switch 155 manually controls the lighting of the xenon lamp 142 via a switch on the operation panel (e.g. the "LAMP" switch 187a of FIG. 19) upon start-up when the power is turned on.

By doing this, either automatic lighting or manual lighting of the xenon lamp 142 in the light source device 103 is possible when the power is turned on, in accordance with the user usage environment.

The front panel control unit 174 can control various settings and displays in the front panel 147 via the MPU 161.

On the basis of various settings on the front panel 147, the MPU 161 controls each unit in the light source device 103 by controlling each unit of the control board 145.

The present embodiment detects the connection state in the connector receiver unit 141 and automatically sets each of the various settings stored in the RAM 162 based on the connection state.

Next, the front panel 147 of the light source device 103 is explained.

Figure 18:
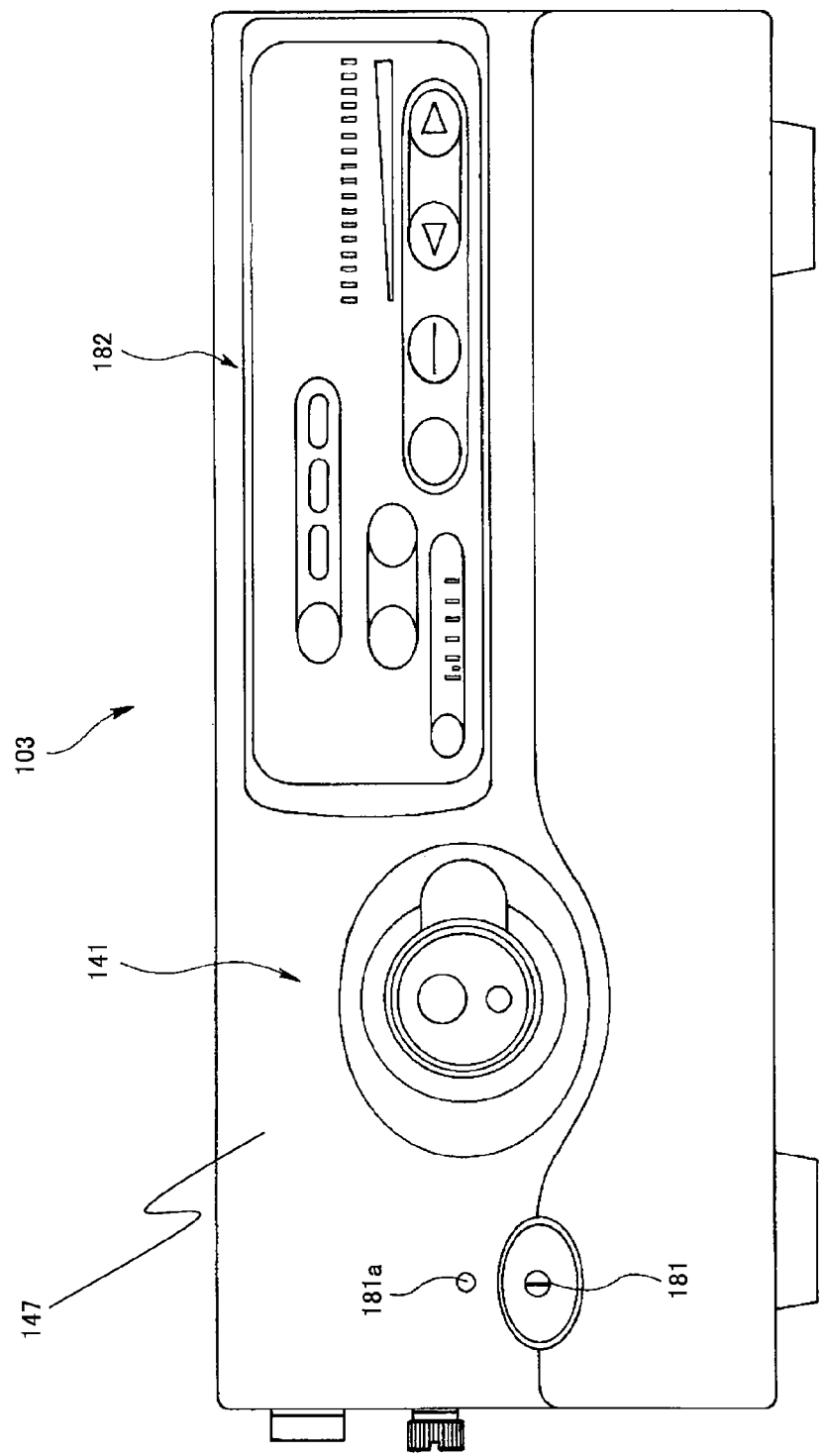
FIG. 18 shows a front view of the light source device of FIG. 15.

FIG. 18 shows a front view of the light source device in FIG. 15. The front panel 147 of the light source device 103 comprises a power switch 181, an operation panel 182, and the connector receiver unit 141.

A power display 181a is provided on the power switch 181. In other words, when the power switch 181 is pressed and the power of the light source device 103 comes on, the power display 181a lights up and indicates a power-on state.

One of the light source connectors 124a, 124c, or 124d of the endoscope 102 (the normal flexible endoscope 111, the normal rigid endoscope 113, or the high-brightness endoscope 114) is selectively connected to the connector receiver unit 141.

An example of a configuration of the operation panel 182 is shown in FIG. 19.

FIG. 19 is an enlarged view showing the configuration of the operation panel of FIG. 18. The operation panel 182 comprises a brightness display unit 183, a spare lamp display unit 184, an air-supply setting display unit 185, a usage time display unit 186, a lamp control setting display unit 187, and an illumination mode setting display unit 188.

The brightness display unit 183 is provided with an indicator 183a for displaying the brightness of the xenon lamp 142. The spare lamp display unit 184 lights when the xenon lamp 142 has gone out and is switched to the spare halogen lamp 175 of the observation mode switching turret 151.

The display "spare lamp" of the spare lamp display unit 184 flashes when the spare halogen lamp 175 is disconnected, pulled out, or not in place.

The air-supply setting display unit 185 comprises an air-supply on/off switch 185a and an air-level switch 185b. The air-supply on/off switch 185a is a switch for supplying air to the endoscope 102. The air-supply level switch 185b is a switch for setting the air-supply level.

The usage time display unit 186 comprises a counter reset switch 186a and the usage time display unit 186b. The usage time display unit 186b displays the usage time of the xenon lamp 142.

The lamp control setting display unit 187 comprises a lamp on/off switch 187a, an automatic/manual setting switch 187b, and operation buttons 187c.

The lamp on/off switch 187a is a switch for turning on/off the lamp after the power switch 181 is turned on. In the lamp on/off switch 187a, the switch has to be held down; this prevents the lamp from being turned off unintentionally.

The automatic/manual setting switch 187b is for switching between automatic/manual performance of brightness adjustment.

The operation buttons 187c are buttons for turning up or down the brightness adjustment value when the brightness is adjusted manually. Manipulation of the up/down buttons gradually increases the setting value or gradually decreases the setting value.

The illumination mode setting display unit 188 comprises a filter mode switch 188a and a special light observation display unit 188b.

The filter mode switch 188a is a switch for selecting the special light observation mode when performing special light observation.

The special light observation display unit 188b comprises a mode LED 188c indicating three special light observation modes usable (valid) for special light observations such as narrow bandwidth light observation or fluorescent light observation. Note that in FIG. 19 the mode LED 188c shows three names for the special light observation modes, "A", "B", and "C".

In the configuration in which a board including optional functions of the special light observation (or a DIP switch etc.) is present in the video processor 104, green light is on in the mode LED 188c corresponding to an available special light observation mode when the power switch 181 is held down and the light source device 103 is in a power ON state in the special light observation display unit 188b. For example, if special light observations A and B are being used, the special light observation mode indicator lights "A" and "B" light in green, and "C" remains off.

In the special light observation display unit 188b, when the endoscope 102 corresponding to each of the special light observation devices is connected, the mode LED 188c corresponding to the special light observation mode corresponding to the special observation mode of the connected endoscope 102 remains lit in green and the other displays are turned off. For example, for connecting an endoscope that enables the special light observation A, the special light observation mode "A" remains lit in green, "B" is turned off, and "C" remains off.

In addition, in this situation, the filter mode switch 188a is turned on and is active. This allows the special light observation display unit 188b to be placed into special light observation mode by holding down the filter mode switch 188a; the display corresponding to each of the special light observation devices changes from white to green (the switch may be a foot switch or a switch on the endoscope etc., depending on the setting). For example, "A" is switched from being lit in green to being lit in white. The mode LED 188c is formed so that, in the special light observation display unit 188b, it is difficult to recognize the display (characters) when they are not lit.

Figure 20:
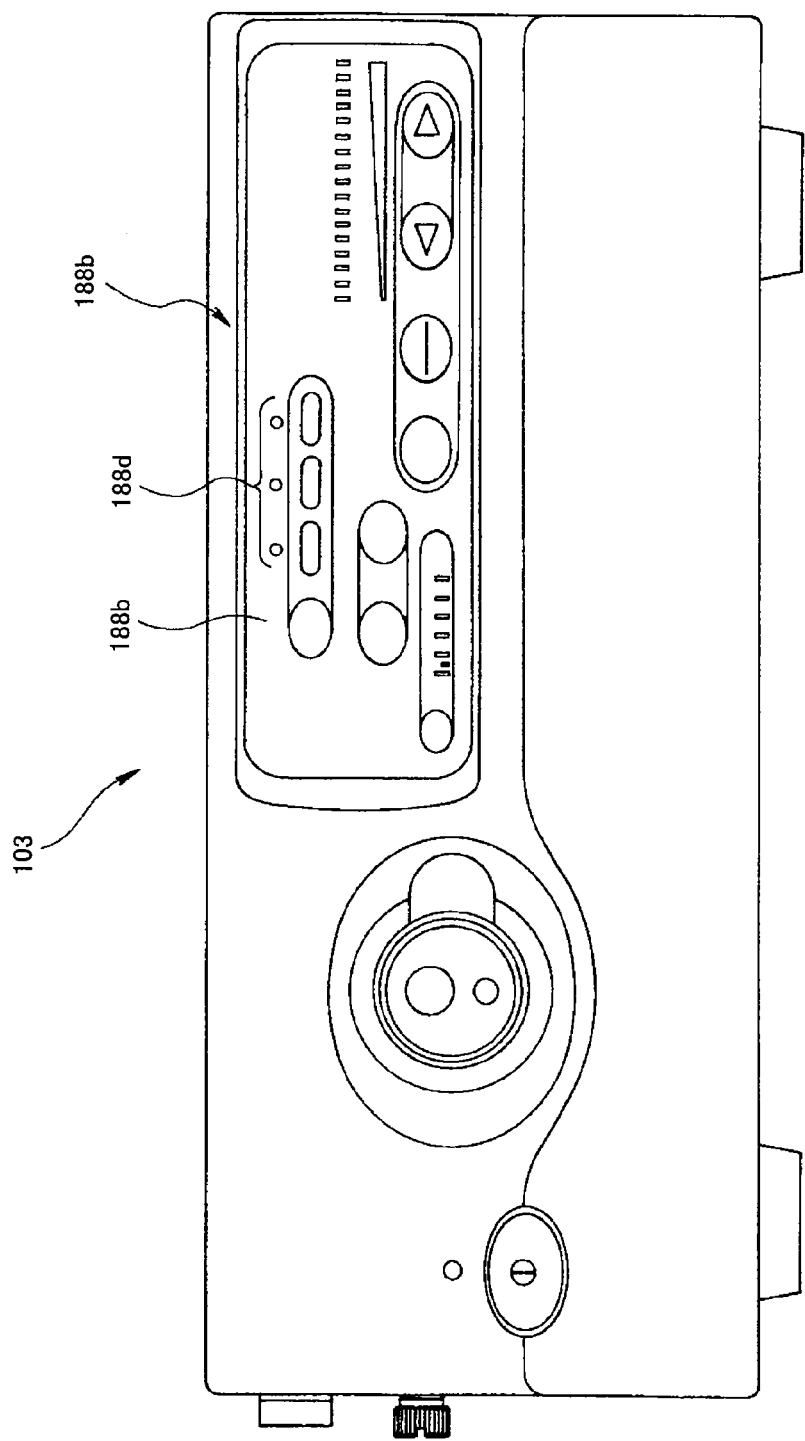
FIG. 20 is a front view of the light source device showing an example of variations of FIG. 18.

It should be noted that the operation panel may be configured as shown in FIG. 20 and FIG. 21.

FIG. 20 is a front view of an example of a variation of the light source device shown in FIG. 18. FIG. 21 is an enlarged view showing the configuration of the operation panel of FIG. 20. As shown in FIG. 20 and FIG. 21, the operation panel 182B comprises a special light observation mode display unit 188d in an illumination mode setting display unit 188B.

In the special light observation mode display unit 188d, a dot LED 188e is provided above each mode LED 188c. When the endoscope 2 corresponding to the special light observation is connected and the corresponding special light observation is prepared, the dot LED 188e is lit.

For example, in the special light observation mode display unit 188d, the LEDs 188e which correspond to the special light observation modes "A" and "B" not including functions of the special light observations "A" and "B", emit green light, and the LED 188e which corresponds to the mode "C" remains being off.

Keeping the same conditions, if the endoscope 102 can perform special light observation "A" and is connected to the light source device 103, the special light observation mode display unit 188d will have only the dot LED 188e above the special light observation light "A" lit. If the endoscope 102 can perform special light observation "B", then the special light observation mode display unit 188d will have only the LED 188e above the special light observation light "B" lit.

When this happens, the filter mode switch 188a will also be lit and the device will be in a condition in which the filter mode switch 188a can be used.

In the light source device 103, when the filter mode switch 188a is held down, the special light observation light "A" of the mode LED 188c lights in white. This indicates the condition in which an observation via the special light observation "A" can be conducted.

When returning to a normal observation, if the filter mode switch 188a is held down once again, the light source device 103 will have the special light observation light "A" of the mode LED 188c lit in green and normal observation can be conducted.

Next, the configurations of the observation mode switching turret 151 and the neutral density mesh turret 152 are explained in detail.

FIG. 22 is a schematic perspective view showing an optical path from the xenon lamp of FIG. 16. The observation mode switching turret 151 is set in the xenon lamp 142 side. The neutral density mesh turret 152 is set in the connector receiver unit 141 side. Note that the connector receiver unit 141 has the endoscope connection detection sensor 146. The configuration of the endoscope connection detection sensor 146 is described in detail later.

Both the observation mode switching turret 151 and the neutral density mesh turret 152 are provided with an initial position detection pin 189.

Figure 23:
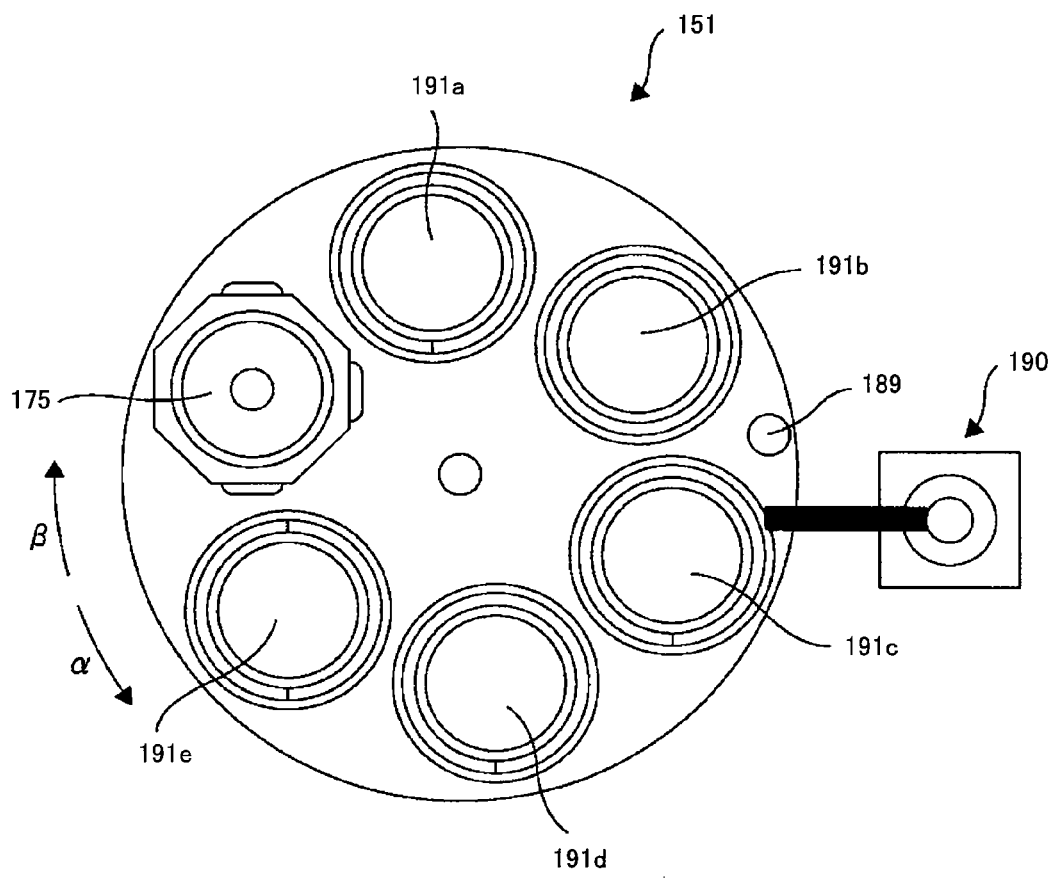
FIG. 23 is a front view showing the surroundings of the observation mode switching turret of FIG. 22.
Figure 24:
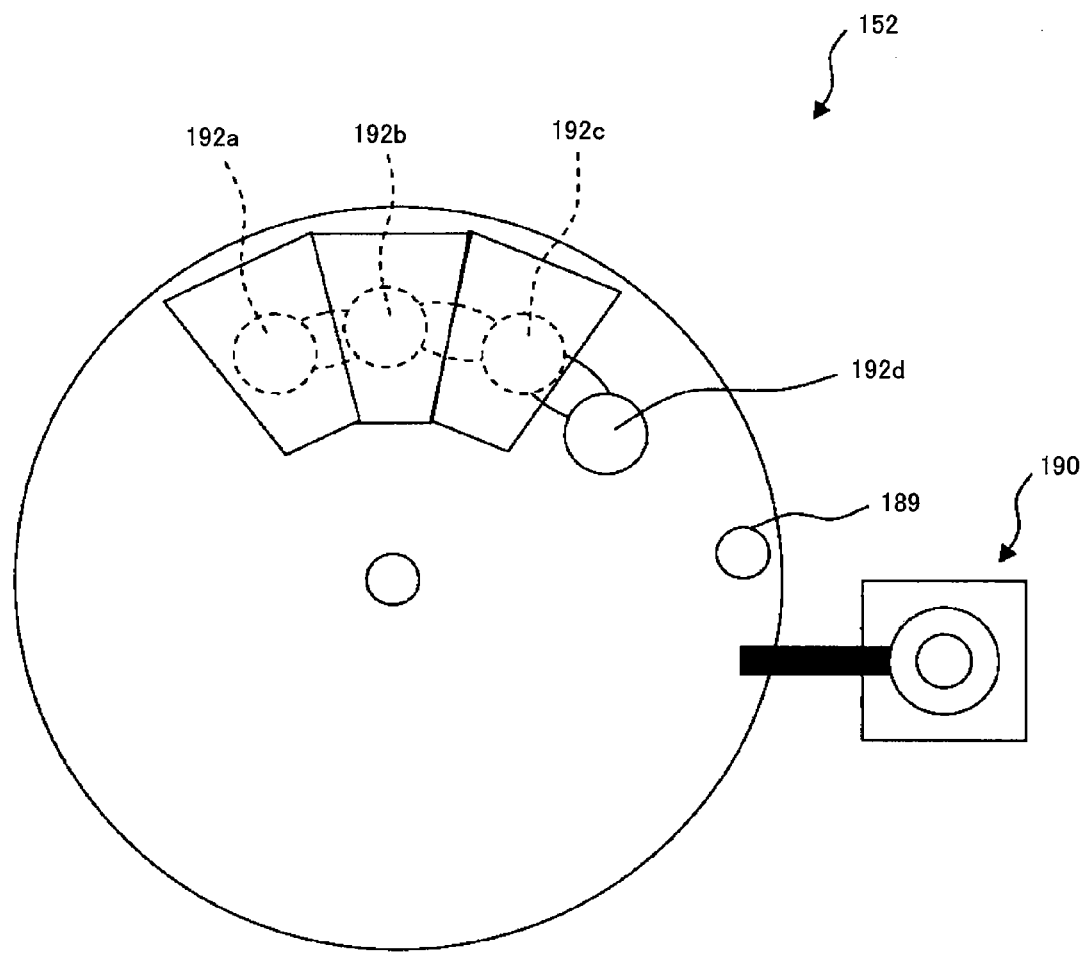
FIG. 24 is a front view showing the surroundings of the neutral density mesh turret of FIG. 22.

FIG. 23 is a front view showing the surroundings of the observation mode switching turret of FIG. 22. FIG. 24 is a front view showing the surroundings of the neutral density mesh turret of FIG. 22. Both the observation mode switching turret 151 and the neutral density mesh turret 152 have their initial position detection pin 189 detected via an initial position detection switch 190, and the initial position of the rotation position can thus be detected.

As shown in FIG. 23, the observation mode switching turret 151 comprises five observation filters in addition to the spare halogen lamp 175.

These observation filters may be, for example, a special observation light transmission filter for infrared light 191a, a normal observation light transmission filter 191b, a special observation light transmission filter for narrowband light 191c, a special observation light transmission filter for fluorescent light 191d, and a special observation light transmission filter for fluorescent/infrared light 191e. These filters are arranged from the right side of the spare halogen lamp 175.

It should be noted that such an arrangement is made because the usages are mainly the following: a: normal 191b≶narrowband 191c, b: fluorescent/infrared 191e≶fluorescent 191d, and c: fluorescent/infrared 191e≶infrared 191a. Therefore, in these three cases, the initial position detection pin 189 has to be located in a reference position detected by the initial position detection switch 190 at least once. The turret 151 rotates in the α direction (forward rotation) and in the β direction (backward rotation) as shown in FIG. 23. The turret 151 realizes the above 'a' and 'b' by rotating in the α direction (forward rotation) and the above 'c' by rotating in the β direction (backward rotation), and has a filter arrangement in which each of the switching speeds can be enhanced fastest to the maximum.

As shown in FIG. 24, the neutral density mesh turret 152 comprises four neutral density mesh filters 192a-192d.

As an example, these neutral density mesh filters 192a-192d are arranged so that the transmission (porosity) becomes higher from left to right, and is set in the following order of transmission: 50%, 65%, 75% and 100% (no mesh).

In the light source device 103 of the present embodiment, when the light source connectors 124a, 124c, and 124d of the endoscope 102 (the normal flexible endoscope 111, the normal rigid endoscope 113, and the high-brightness rigid endoscope 114) are pulled out from the connector receiver unit 141, or when initializing, the turret 152 is set to the initial position so that the neutral density mesh filter 192a with a transmission of 50% is set on the optical path.

It should be noted that even if the turret stops at a non-transmissive part other than the neutral density mesh filters 192a-192d for some reason, the neutral density mesh turret may have the configuration shown in FIG. 25 so that the light is not shielded.

FIG. 25 is a front view of the neutral density mesh turret showing example (1) of a variation of FIG. 24. As shown in FIG. 25, the neutral density mesh turret 152B forms small holes for optical transmission 193. It is possible to prevent complete shielding of the illuminating light supplied to the endoscope 102 via these small holes for optical transmission 193.

Figure 26:
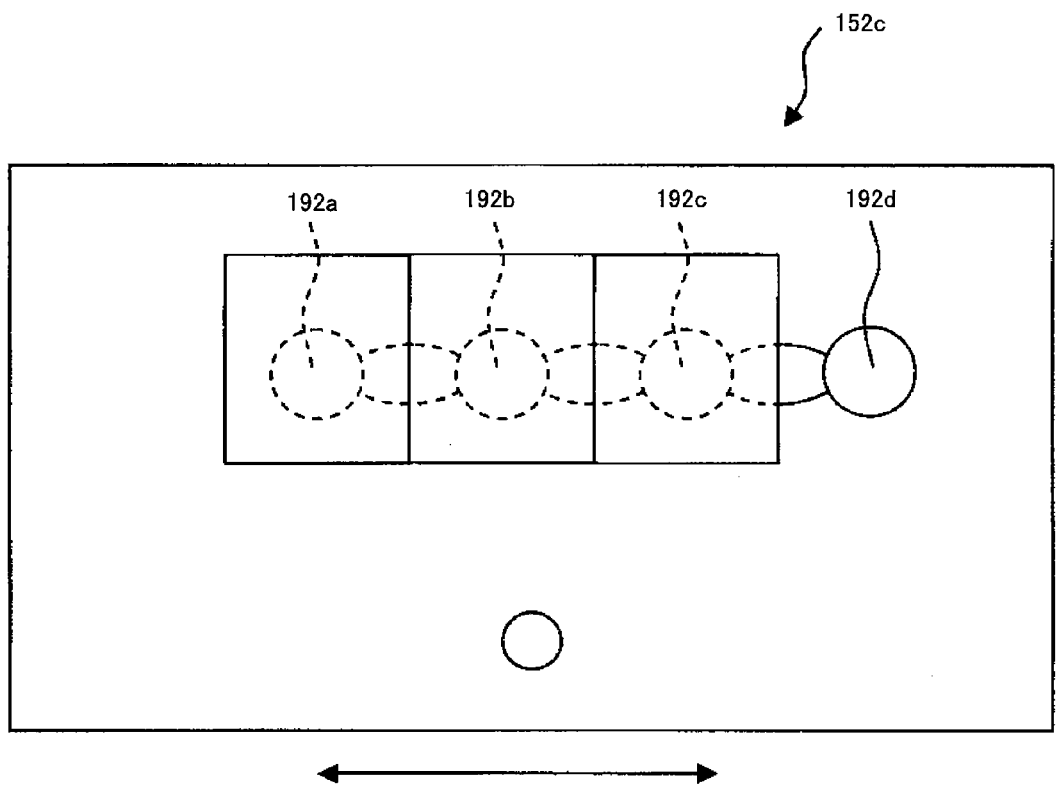
FIG. 26 is a front view of the neutral density mesh turret showing an example (2) of a variation of FIG. 24.

In addition, the neutral density mesh turret 152 is configured so as to be able to rotate under the power of the motor 159b; however, a slide neutral density mesh 152C may be used as shown in FIG. 26.

FIG. 26 is a front view of the neutral density mesh turret showing example (2) of a variation of FIG. 24. The slide neutral density mesh 152C is formed in an approximate rectangle. The slide neutral density mesh 152C can be driven in parallel by linear driving of the motor.

By moving in parallel via linear driving, the neutral density mesh turret 152C can have a configuration similar to that of the turret moving in rotation using a motor.

Next, further aspects of the configuration of the neutral density mesh turret 152 are explained in detail.

Figure 27:
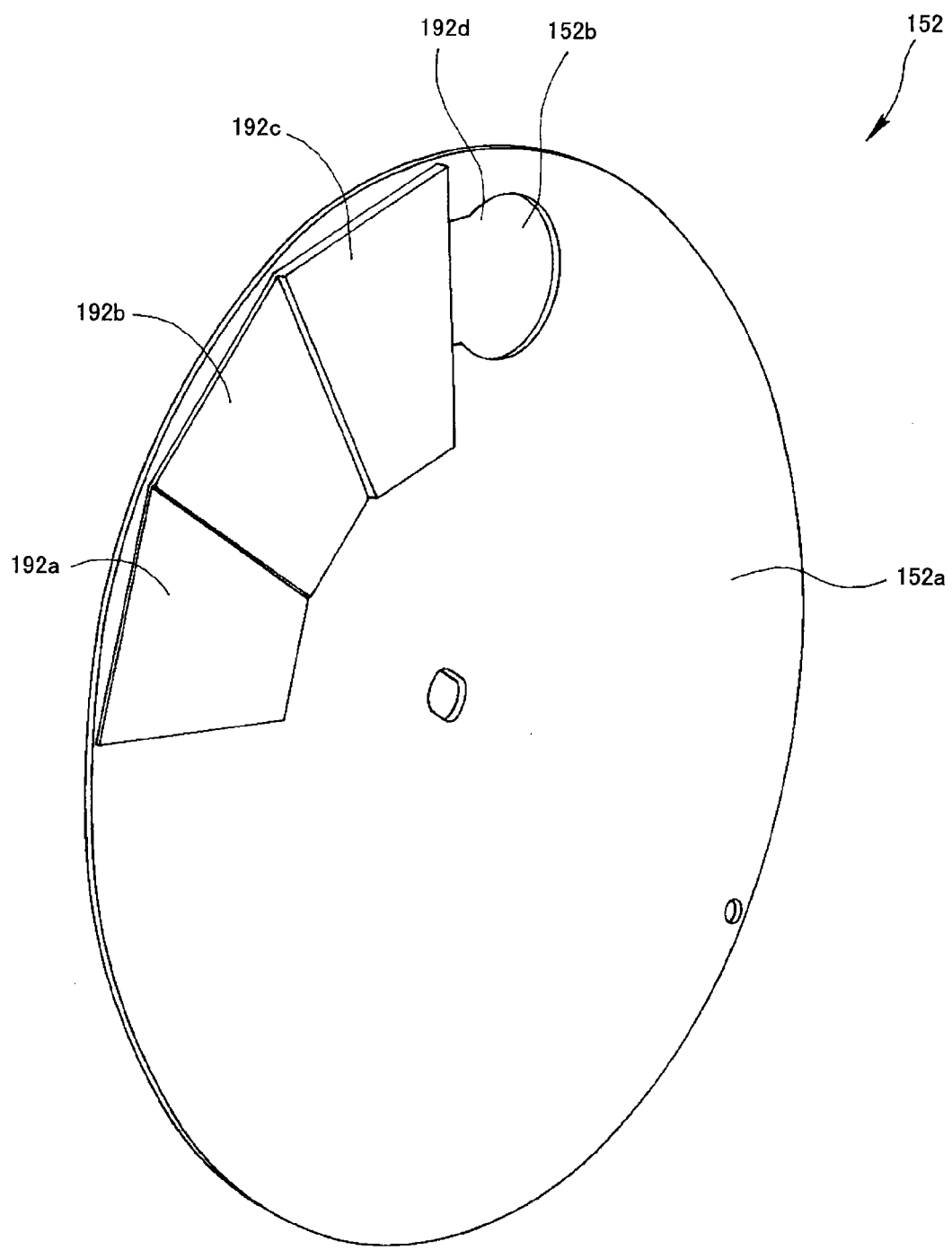
FIG. 27 is a perspective view showing a configuration of the neutral density mesh turret of FIG. 24 in detail.
Figure 28:
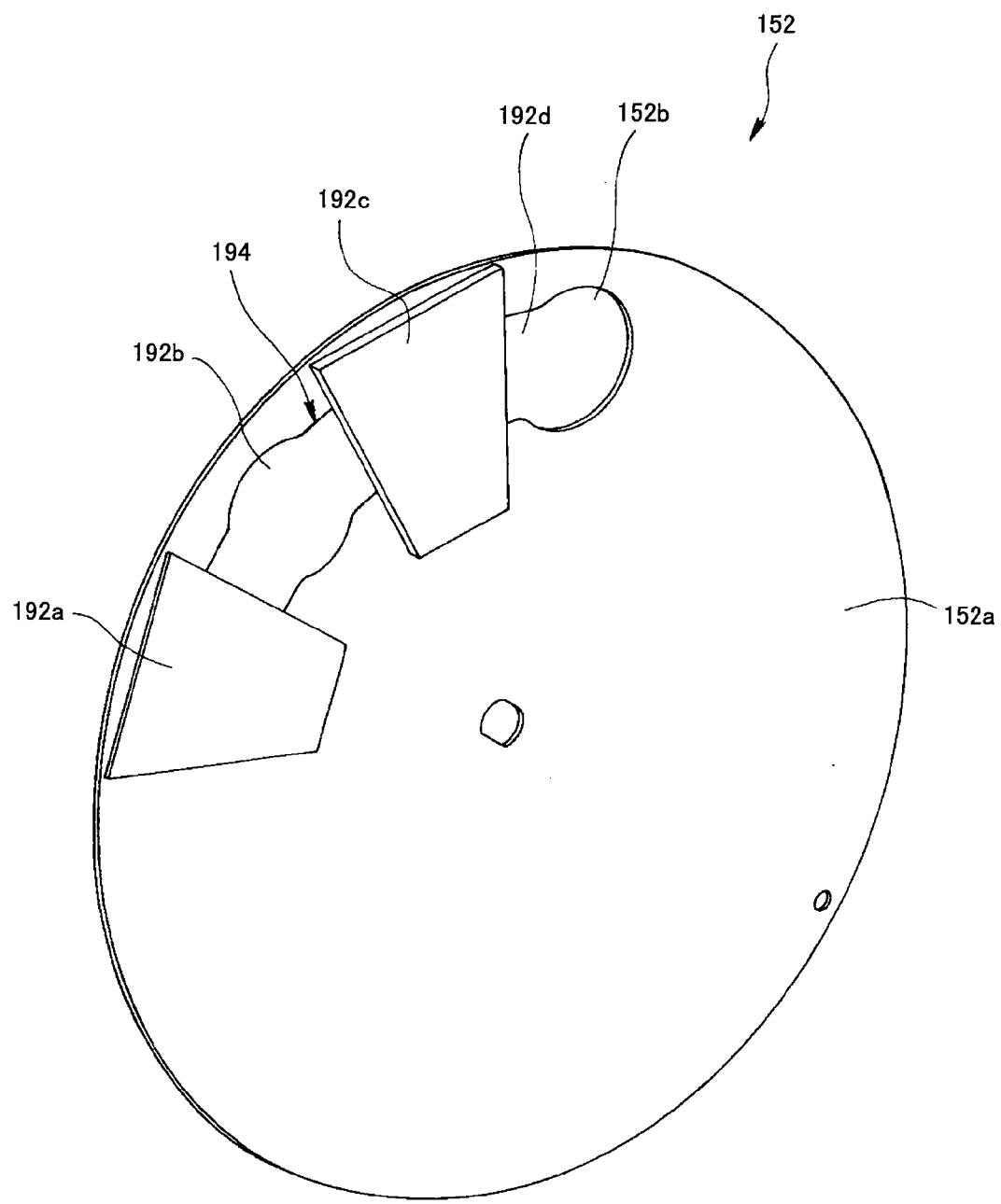
FIG. 28 is a perspective view showing an example of a modification in the attachment of the neutral density mesh of FIG. 27.
Figure 29:
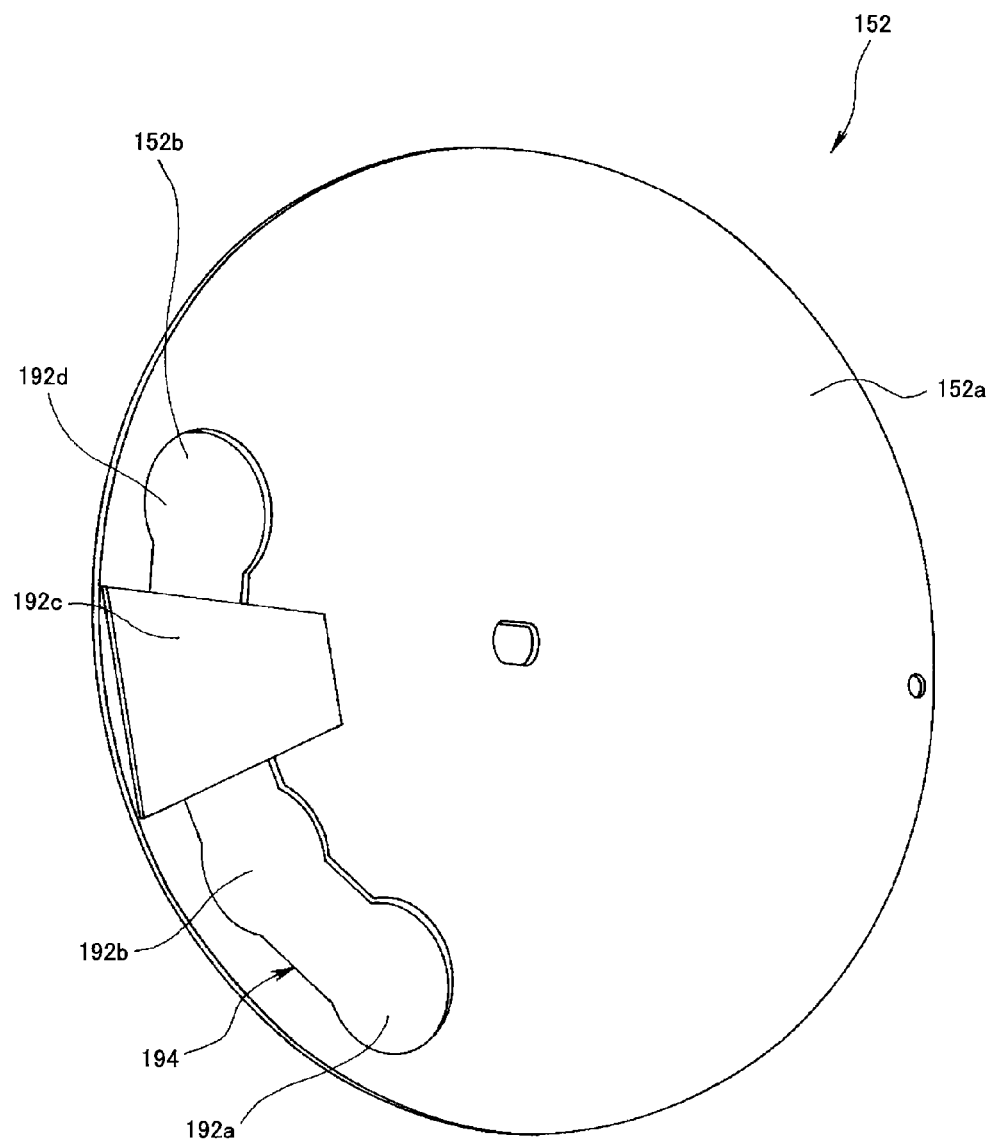
FIG. 29 is a perspective view showing the back of the neutral density mesh turret of FIG. 28.

FIG. 27 is a perspective view showing in detail the configuration of the neutral density mesh turret of FIG. 24. FIG. 28 is a perspective view showing an example of a modification in the attachment of the neutral density mesh of FIG. 27. FIG. 29 is a perspective view showing the back of the neutral density mesh turret of FIG. 28.

As shown in FIGS. 27-29, the neutral density mesh turret 152 is configured by attaching the trapezoid-shaped neutral density mesh filters 192a-192d to a hole unit 194 formed by having four holes linked together in a row on a turret board 152a.

The neutral density mesh filters 192a-192d have weaved wires such as metallic material wires with a thin wire diameter, and are formed in a single layer or multiple layers. The neutral density mesh filters 192a-192d are attached to a hole 194 (on one side or both sides). The neutral density mesh filters 192a-192d are formed to have transmissions of 50%, 65%, 75%, 100% (no mesh), respectively, as explained in an example above, in accordance with the hole 194.

In FIG. 28 and FIG. 29, the neutral density mesh filters 192a-192d are attached to both sides of the hole 194 with no space left between. With this configuration, it is possible to prevent the mesh from misaligning for some reason, which cannot be done with the mesh filters attached on only one side as in FIG. 27. Thus, the maximum light intensity cannot be above the setting even if a space is generated between the meshes. Additionally, it is possible to attach the meshes so that the adjacent meshes overlap each other, further preventing unintended light leakage. Furthermore, the mesh filters are made so as to be processed easily, and therefore the adjacent meshes can be attached in a configuration in which they overlap each other.

As explained later, combinations of the neutral density mesh filters 192a-192d and the observation filters 191a-191d are determined by the combination of the endoscope 102 (the normal flexible endoscope 111 in which two types of maximum light intensity can be set, the normal rigid endoscope 113, or the high-brightness endoscope 114) and the observation mode (normal observation, narrowband observation, infrared observation, or narrowband/infrared normal observation).

First, detection of the endoscope type is explained.

The light source device 103 detects the endoscope type via the endoscope connection detection sensor 146 when one of the light source connectors 124, 124c and 124d of the endoscope 102 (the normal flexible endoscope 111, the normal rigid endoscope 113, or the high-brightness rigid endoscope 114) are selectively connected to the connector receiver unit 141.

Figure 30:
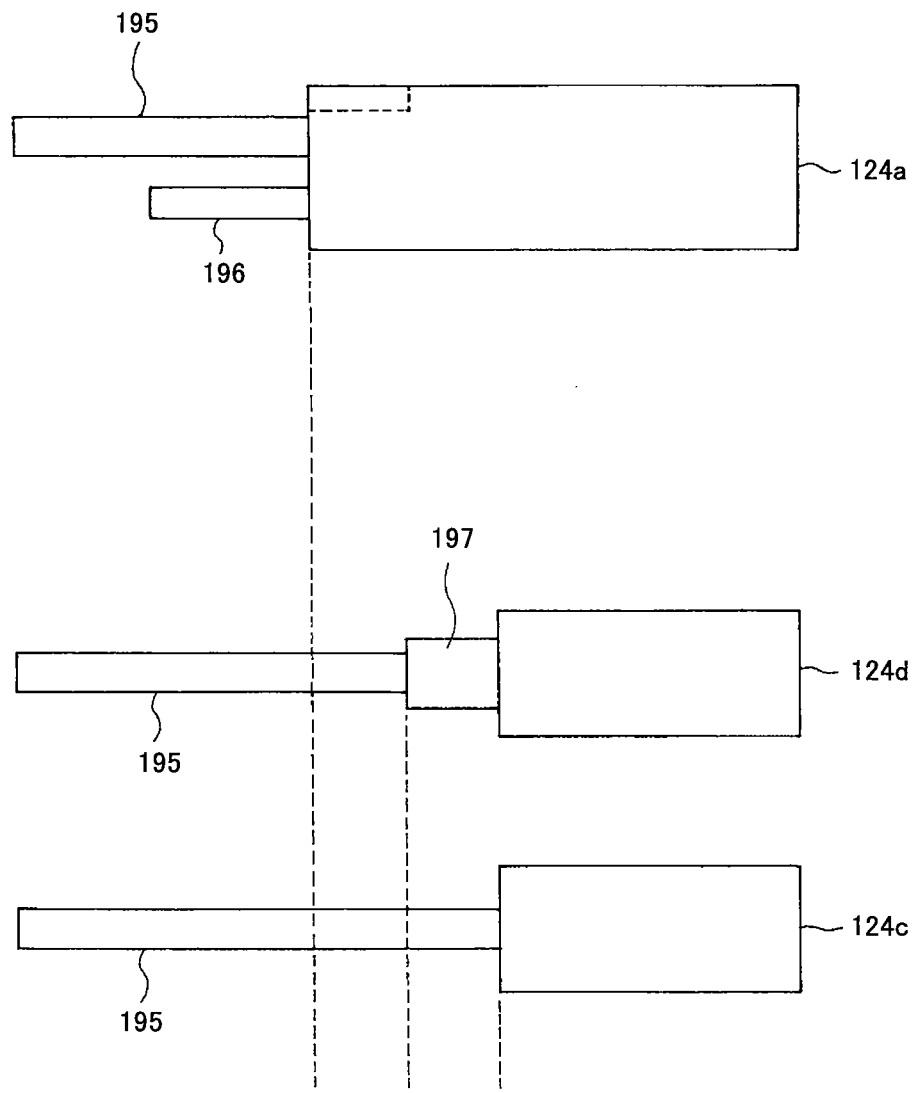
FIG. 30 is an overview explanatory diagram showing the relative positions in the state in which the connector of the endoscope of FIG. 15 is connected to the light source.

Here, the endoscope 102 (the normal flexible endoscope 111, the normal rigid endoscope 113, or the high-brightness rigid endoscope 114) comprises the light source connectors 124a, 124c, and 124d, as shown in FIG. 30.

FIG. 30 is an overview explanatory diagram showing the relative positions in a state in which the connector of the endoscope of FIG. 15 is connected to the light source. A light guide end 195, which is an input end face of the light guide 131a, and an air-supply end 196 of the air-supply channel 131c are extended from the light source connector 124a of the normal flexible endoscope 111.

On the other hand, the light guide end 195 alone is extended from both the normal rigid endoscope 113 and the high-brightness rigid endoscope 114.

In the light source connector 124d of the high-brightness rigid endoscope 114, the light guide end 195 is provided with a protrusion 197. Because of the protrusion, the endoscope connection detection sensor 146 can detect the difference between the normal rigid endoscope 113 and the high-brightness rigid endoscope 114 as explained above.

Note that the use of a high-brightness flexible endoscope is also possible. In such a case, a groove is formed, as shown by the broken line of FIG. 30, on the distal end connector 124a of the normal flexible endoscope at a position in which an advance/withdraw member 204 of FIG. 31 etc. is pushed in, explained later. When this occurs, the distal end connector 124a can be pushed in only to the same position as the high-brightness rigid endoscope. Such a configuration can be easily obtained.

Next, the configuration of the endoscope connection detection sensor 146 is explained in detail.

Figure 32:
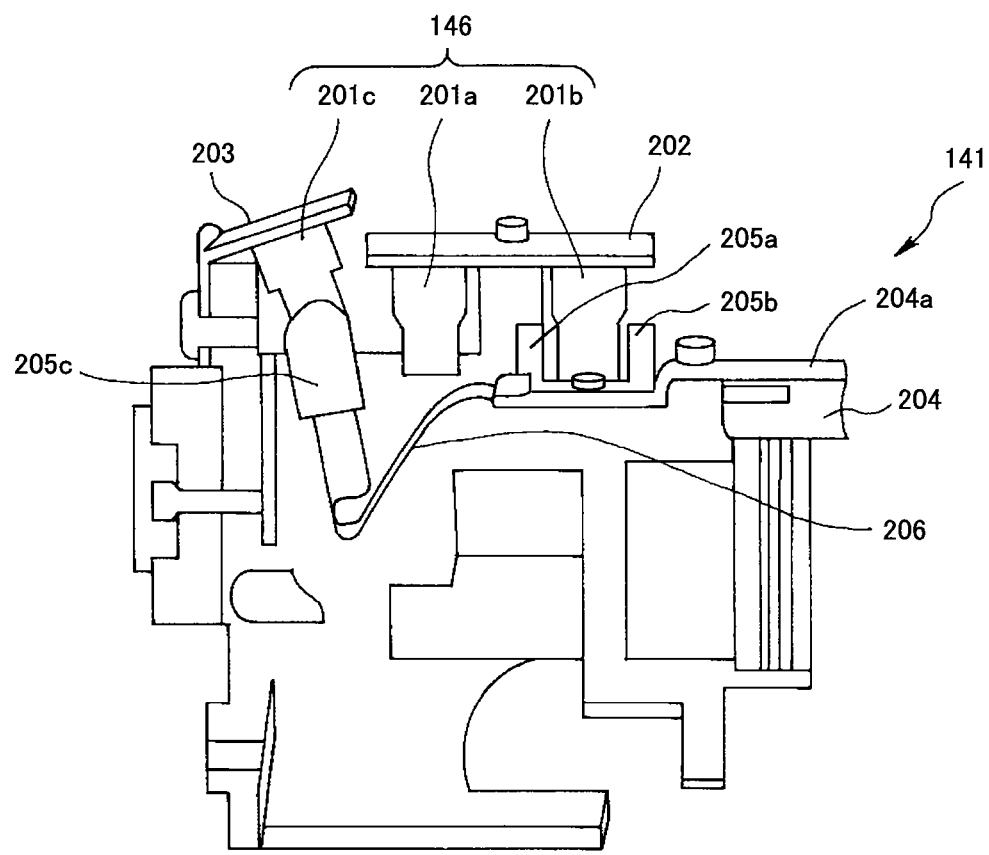
FIG. 32 is a cross-sectional view of the surroundings of the connector receiver unit of FIG. 31.

FIG. 31 is a perspective view showing the surroundings of the connector receiver unit of FIG. 22. FIG. 32 is a cross-sectional view of the surroundings of the connector receiver unit of FIG. 31. The endoscope connection detection sensor 146 is attached to the connector receiver unit 141.

The endoscope connection detection sensor 146 comprises three sensors, the first through third photosensors 201a-201c.

The first photosensor 201a and the second photosensor 201b are carried in the first fixing member 202 and are set in the direction of the insertion axis of the connector. The third photosensor 201c is carried in the second fixing member 203 and is set in a direction different from that of the first photosensor 201a and the second photosensor 201c. Note that the first fixing member 202 and the second fixing member 203 may be one.

The connector receiver unit 141 is provided with an advance/withdraw member 204 which is held on by a holding member 204a that advances and withdraws by being pushed by the distal end when the endoscope of one of the light source connectors 124a, 124c and 124d to be connected is inserted.

The advance/withdraw member 204 comprises a first protrusion 205a and a second protrusion 205b, which can pass through the first photosensor 201a and the second photosensor 201b, respectively. A flexible member (made of an elastic material such as leaf spring) 206 is extended from the distal end side of the advance/withdraw member 204. The ends of the flexible member 206 are provided with a third protrusion 205c, which can pass through the third photosensor 201c at the insertion of the light guide end 195 when it is pushed by the light guide end 195.

In this example, the first through third photosensors 201a-201c define the state where the light is not shielded as 1 (ON) and the state where the light is shielded by the first through third protrusions 205a-205c as 0 (OFF).

In a state in which the light source connectors 124a, 124c, and 124d shown in FIG. 30 are not connected to the connector receiver unit 141, the state is "1" in the first photosensor 201a and the second photosensor 201b since the light is not shielded by the first protrusion 205a and the second protrusion 205b, and the state is "0" in the third photosensor 201c since the light is shielded by the third protrusion 205c. In other words, the first through third photosensors 201a-201c are (1, 1, 0) (see FIG. 36 and FIG. 39).

Figure 33:
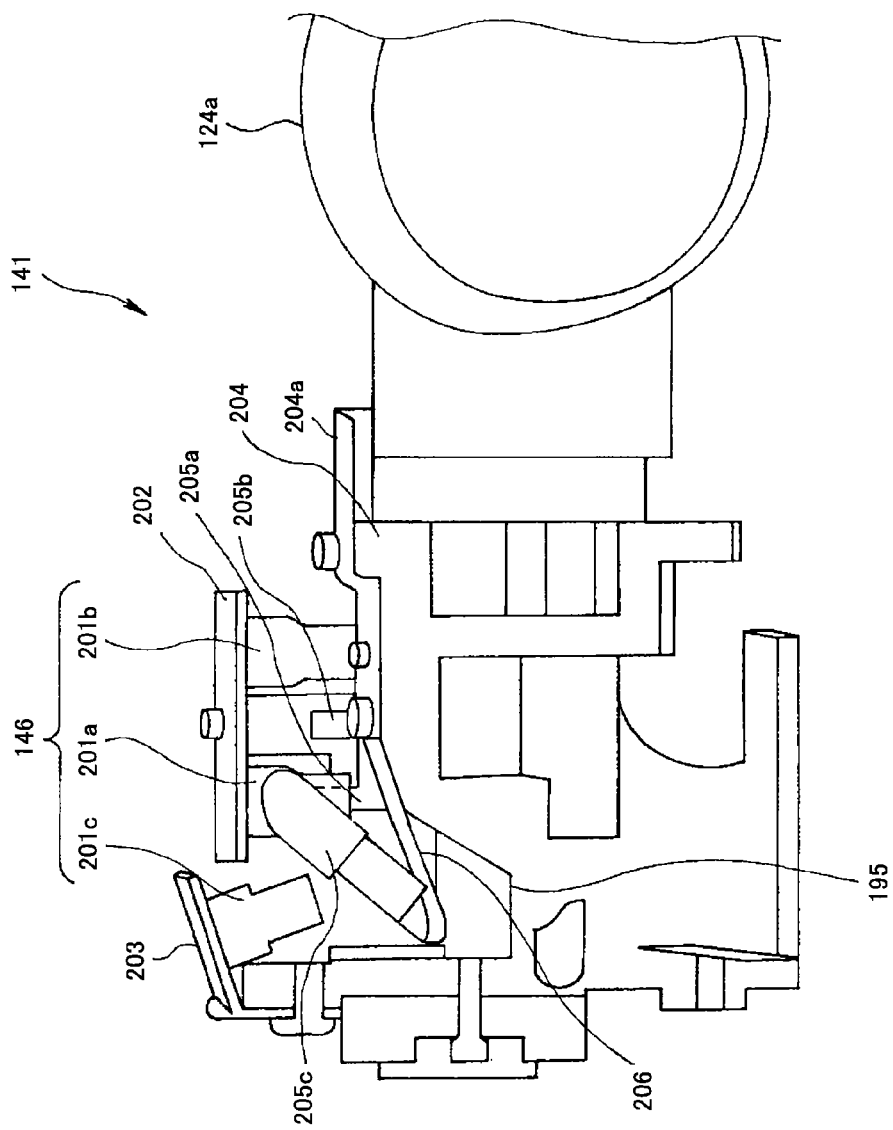
FIG. 33 is a cross-sectional view of the light source connector of the normal flexible endoscope to the connector receiver unit of FIG. 32.
Figure 35:
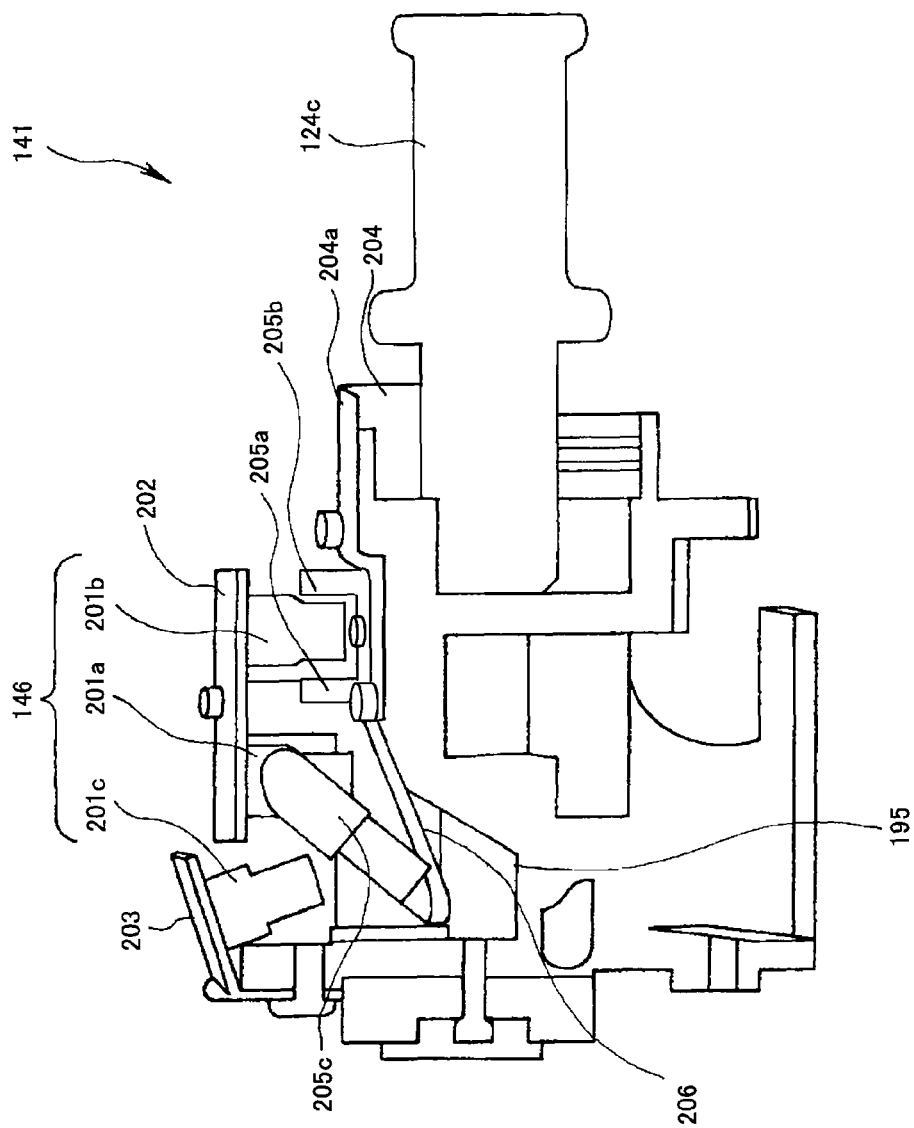
FIG. 35 is a cross-sectional view of a case in which the light source connector of the normal rigid endoscope is connected to the connector receiver unit of FIG. 32.

The light source connectors 124a, 124c, and 124d of the endoscope 102 (the normal flexible endoscope 111, the normal rigid endoscope 113, the high-brightness rigid endoscope 114) are in the states shown in FIG. 33, FIG. 34, and FIG. 35 when being inserted into the connector receiver unit 141. The different possible relations between the first through third photosensors 201a-201c and the first through third protrusions 205a-205c are the states shown in FIGS. 36-40.

Further details are explained.

FIG. 33 is a cross-sectional view of the connection of the light source of the normal flexible endoscope to the connector receiver unit of FIG. 32. As shown in FIG. 33, the light source connector 124a of the normal flexible endoscope 111 is inserted into the connector receiver unit 141. When this happens, the first photosensor 201a and the second photosensor 201b shift from the state shown in FIG. 36 to the state shown in FIG. 38.

FIG. 36 is an overview explanatory diagram showing the relationship between the first and second photosensors and the first and the second protrusions in FIG. 32. FIG. 38 is an overview explanatory diagram showing the relationship between the first and second photosensors and the first and the second protrusions in FIG. 34. As shown in FIG. 38, the first photosensor 201a is OFF since the light is shielded by the first protrusion 205a. On the other hand, the second photosensor 201b is ON since the light is not shielded by the second protrusion 205b.

Figure 39:
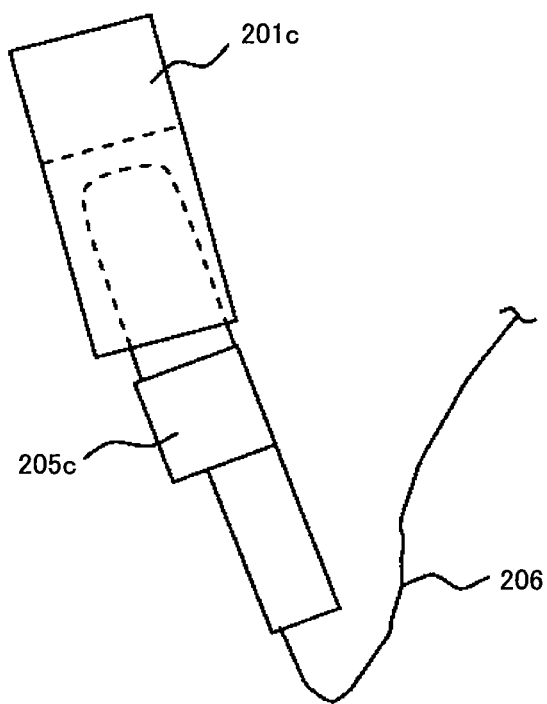
FIG. 39 is an overview explanatory diagram showing the relation between the third photosensor and the third protrusion in the state in which the third photosensor is OFF in the second mode.

The state of the third photosensor 201c shifts from the state shown in FIG. 39 to the state shown in FIG. 40.

FIG. 39 is an overview explanatory diagram showing the relation between the third photosensor and the third protrusion in the state in which the third photosensor is OFF. FIG. 40 is an overview explanatory diagram showing the relation between the third photosensor and the third protrusion in the state in which the third photosensor is ON. As shown in FIG. 40, the third photosensor 201c is ON since it is in a state in which the third protrusion 205c is moved by the distal end of the light guide end 195 and the light is not shielded.

Then, in the first through third photosensors 201a-201c, when the light source connector 124a of the normal flexible endoscope 111 is connected to the connector receiver unit 141, the state changes from the unconnected (1, 1, 0) to (0, 1, 1).

FIG. 34 is a cross-sectional view of a case in which the light source connector of the high-brightness rigid endoscope is connected to the connector receiver unit of FIG. 32. As shown in FIG. 34, the light source connector 124d of the high-brightness rigid endoscope 114 is inserted into the connector receiver unit 141. At that time, the states of the first photosensor 201a and the second photosensor 201b shift from the state shown in FIG. 36 to the state shown in FIG. 37.

FIG. 37 is an overview explanatory diagram showing the relationship between the first and second photosensors and the first and second protrusions in FIG. 33. As shown in FIG. 37, since the light is not shielded, the first photosensor 201a is ON, and since the light is shielded by the second protrusion 205b, the second photosensor 210b is OFF.

The third photosensor 201c shifts its state from the state shown in FIG. 39 to the state shown in FIG. 40, in the same manner as with the insertion of the normal flexible endoscope 111, and becomes ON since the light is not shielded.

Then, for the first through third photosensors 201a-201c, when the light source connector 124d of the high-brightness rigid endoscope 114 is connected to the connector receiver unit 141, the state changes from the unconnected (1, 1, 0) to (1, 0, 1).

FIG. 35 is a cross-sectional view of a case in which the light source connector of the normal rigid endoscope is connected to the connector receiver unit of FIG. 32. As shown in FIG. 35, the light source connector 124c of the normal rigid endoscope 113 is inserted into the connector receiver unit 141. When that happens, since the advance/withdraw member 204 is not pushed and parallel movement does not occur, the first photosensor 201a and the second photosensor 201b are in the same state as the unconnected state shown in FIG. 36, and since the light is not shielded, both of the sensors are ON.

The third photosensor 201c shifts from the state shown in FIG. 39 to the state shown in FIG. 40 in the same manner as the insertion of the normal flexible endoscope 111, and since the light is shielded, the sensor is ON.

Then, the state changes from the unconnected (1, 1, 0) to (1, 1, 1) in the first through third photosensors 201a-201c when the light source connector 124c of the normal rigid endoscope 113 is connected to the connector receiver unit 141.

The states of the first through third photosensors 201a-201c are summarized in Table 1.

TABLE 1

| Type | First photosensor (101a) | Second photosensor (101b) | Third photosensor (101c) |
|---|---|---|---|
| Normal flexible endoscope | 0 | 1 | 1 |
| Normal rigid endoscope | 1 | 1 | 1 |
| High-brightness rigid endoscope | 1 | 0 | 1 |
| Unconnected | 1 | 1 | 0 |
| Error | Other than the above | | |

Note that the last row of Table 1 is for the case of error. In such a case, the first through third photosensors 201a-201c exhibit a combination other than the above combinations.

With the above combinations, the light source device 3 can determine the connection state in the connector receiver unit 141 and can determine the type of connected endoscope 102 (the normal flexible endoscope 111, the normal rigid endoscope 113, or the high-brightness rigid endoscope 114).

Accordingly, the light source device 103 can set the position of the mesh of the mesh turret, which determines each maximum allowable light intensity, on the basis of connection state D (explained later) in the connector receiver unit 141. Additionally, it is possible to automatically set the other settings.

Examples of the settings are described in Table 2. The settings in Table 2 are stored in advance as setting information in the FRAM 162.

TABLE 2

| Setting item | Setting contents | Initial setting |
|---|---|---|
| Normal flexible endoscope connection setting D = 0 | Automatic/manual light adjustment (set at startup) | Automatic |
| | Brightness level (set at startup) | Median value |
| | Automatic/manual light adjustment (set at automatic/manual setting) | Manual |
| | Brightness level (set at automatic/manual setting) | Minimum value |
| | Pump ON/OFF | ON |
| | Pump level | Maximum value |
| | High-brightness OFF (internal operation, display off) | — |
| Normal rigid endoscope connection setting D = 2 | Automatic/manual light adjustment (set at startup) | Automatic |
| | Brightness level (set at startup) | Median value |
| | Automatic/manual light adjustment (set at automatic/manual setting) | Manual |
| | Brightness level (set at automatic/manual setting) | Minimum value |
| | Pump (internal operation OFF, display off) | — |
| | Pump level (display off) | — |
| | High-brightness OFF (internal operation, display off) | — |
| High-brightness rigid endoscope connection setting D = 3 | Automatic/manual light adjustment (set at startup) | Automatic |
| | Brightness level (set at startup) | Median value |
| | Automatic/manual light adjustment (set at automatic/manual setting) | Manual |
| | Brightness level (set at automatic/manual setting) | Minimum value |
| | Pump (internal operation OFF, display off) | — |
| | Pump level (display off) | — |
| | High-brightness OFF/OFF | ON |
| Unconnected setting D = 4 | Setting display information of flexible/rigid endoscope immediately before being disconnected | Initial setting is D = 0 |
| | Pump (internal operation OFF) | — |
| | Diaphragm fixing (internal operation) | — |
| Connection detection error setting D = 5 | Normal flexible endoscope connection setting | — |

Note that the normal flexible endoscope 11, since the air-supply channel 131c is provided as described above, can supply air via the pump 153 of the light source device 3. On the other hand, the normal rigid endoscope 113 and the high-brightness rigid endoscope 114 do not use the pump 153.

In addition, the illuminating switches and display of the operation panel may be turned on/off in accordance with these setting items.

Based on the combination type of observation mode (normal observation, narrowband observation, infrared observation, or narrowband/ infrared normal observation) and type of endoscope 102 (normal flexible endoscope 111, normal rigid endoscope 113, or high-brightness rigid endoscope 114), the combination of neutral density mesh filters 192a-192d and observation filters 191a-191e is determined as shown in Table 3.

TABLE 3

| Connected endoscope type | Observation mode | Observation mode switching turret | | Neutral density mesh turret | |
|---|---|---|---|---|---|
| | | Filter type | Transmission (%) | Mesh type | Transmission (%) |
| Normal flexible endoscope | Normal observation 1 | Normal observation light transmission filter | 85 | Neutral density mesh 2 | 65 |
| Normal flexible endoscope | Normal observation 2 | Normal observation light transmission filter | 85 | Neutral density mesh 3 | 75 |
| Normal flexible endoscope | Special light observation 1 | Special observation light transmission filter 4 | 50 | Neutral density mesh 4 | 100 |
| Normal/high-brightness rigid endoscope | Special light observation 2 | Special observation light transmission filter 3 | 60 | Neutral density mesh 4 | 100 |
| Normal/high-brightness rigid endoscope | Special light observation 3 | Special observation light transmission filter 1 | 75 | Neutral density mesh 4 | 100 |
| Normal/high-Brightness rigid endoscope | Special light observation 4 | Special observation light transmission filter 2 | 65 | Neutral density mesh 4 | 100 |
| Normal/high-Brightness rigid Endoscope | Normal observation 3 | Normal observation light transmission filter | 85 | Neutral density mesh 1 | 50 |
| High-brightness rigid endoscope | High-brightness normal observation 1 | Normal observation light transmission filter | 85 | Neutral density mesh 4 | 100 |
| Flexible endoscope/ rigid endoscope | Abnormal observation | Emergency lighting: halogen lamp | — (no transmission) | Neutral density mesh 4 | 100 |
| Unconnected | Unconnected | Filter used immediately before being disconnected | Depends on filter used immediately before being disconnected | Neutral density mesh 1 | 50 |

In a case in which the light input into the endoscope 102 is lamp light with an intensity of 100, the high-brightness light intensity is, for example, 100 (lamp light intensity)×0.85 (85% transmission of the observation mode switching turret 151)×1 (100% transmission of the neutral density mesh turret 52)=85.

In the light source device 103 with the above configuration, one of the light source connectors 124a, 124c, or 124d of the endoscope 102 (the normal flexible endoscope 11, the normal rigid endoscope 113, or the high-brightness rigid endoscope 114) is selectively connected in a detachable manner, as shown in FIG. 15, and is used for endoscopic examination.

A user turns on the power, starts the light source device 103, and conducts the endoscopic examination.

If the automatic/manual lighting switching switch 155 is set to automatic, the MPU 161 controls the lamp lighting control unit 168 by a detection signal from the automatic/manual lighting switching control unit 173 (which received a signal from the automatic/manual lighting switching switch 155) so that the xenon lamp 142 lights at the startup time when the power switch is turned ON.

In contrast, when the automatic/manual lighting switching switch 155 is set to manual, the MPU 161 controls the lamp lighting control unit 168 so that the xenon lamp 142 lights when the lamp ON/OFF switch 187a of the operation panel 182 is held down after startup when the power switch is turned ON.

Figure 41:
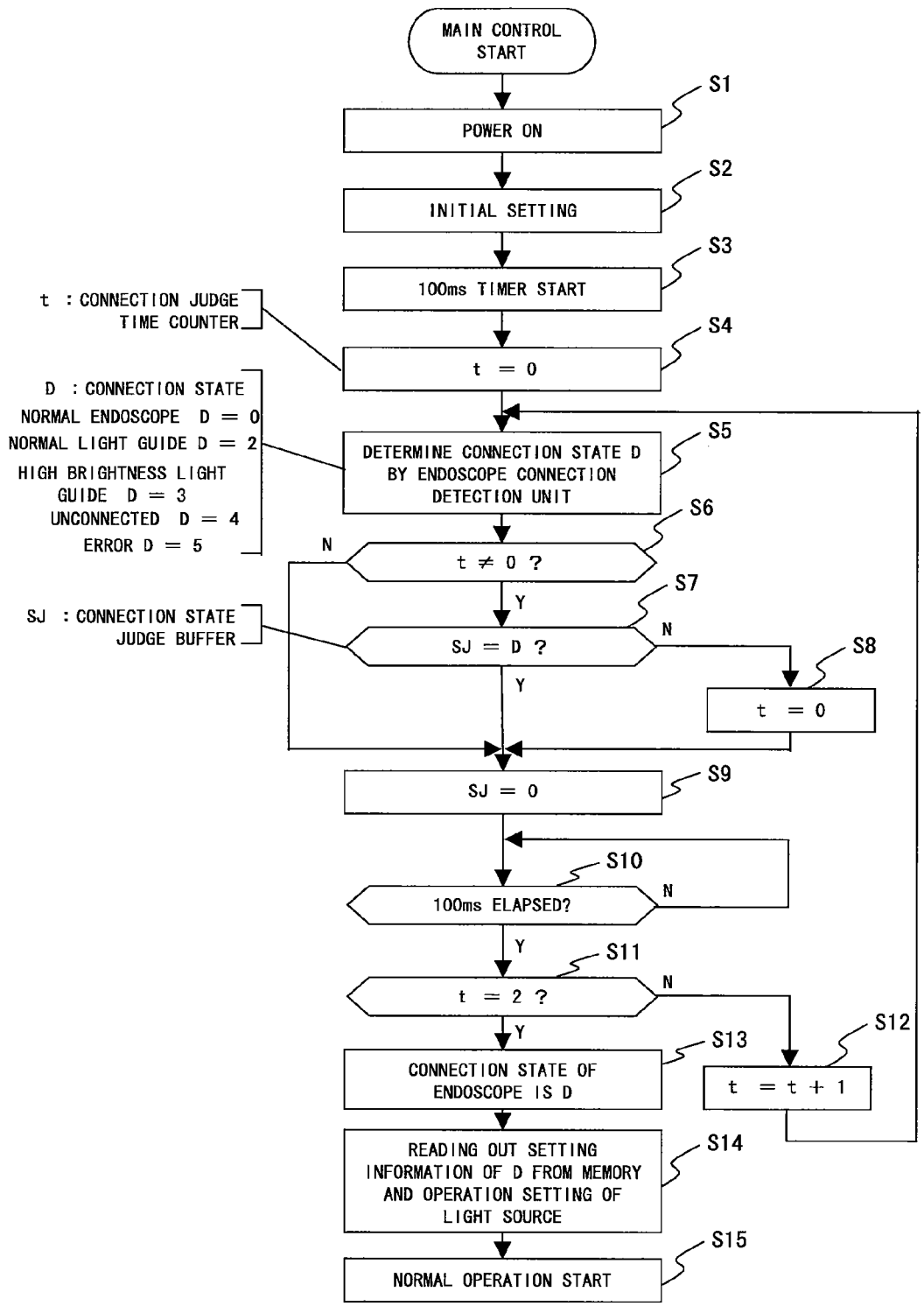
FIG. 41 is the main flowchart showing the operation of the MPU in the second mode.

When that happens, the MPU 161 of the light source device 103 controls each unit in the device by controlling each unit of the control board 145 in a manner following the main flowchart shown in FIG. 41.

FIG. 41 is a flowchart showing the operation of the MPU. In the MPU 161, the initial setting is performed (step S2) when the power of the light source device 103 is turned ON by turning on the power switch 181 (step Si).

In addition, the MPU 161 starts a 100 ms count with a 100 ms timer (step S3).

In the following description, the MPU 161 assigns a connection state D, which is the current connection detection result, to a connection state judge buffer SJ for every 100 ms. For the MPU 161, the connection state is determined to be the connection state D if the connection state judge buffer SJ(D) does not change for 200 ms (until removal of noise or chattering). Note that the connection judge buffer SJ is provided in the FRAM 162.

First, the MPU 161 assigns 0 to a connection judge time counter t (step S4). Next, the MPU 16 determines the connection state D in the connector receiver unit 141 detected by the endoscope connection detection unit 166 (step S5). Note that the connection judge time counter t represents an elapsed time of 100 ms when t=1 and an elapsed time of 200 ms when t=2.

Here, on the basis of an ON/OFF signal input from the endoscope connection detection sensor 146 (the first through third photosensors 201a-201c), the endoscope connection detection unit 166 obtains one of five values, from 1 to 5 shown below, as the connection state D, as described in Table 1.

Connection state D=0: when the normal flexible endoscope 111 is connected

Connection state D=2: when the normal rigid endoscope 113 is connected

Connection state D=3: when the high-brightness rigid endoscope 114 is connected

Connection state D=4: when no endoscope is connected

Connection state D=5: when an error is generated

Next, the MPU 161 determines whether the connection determination time counter t is at a value other than 0 (step S6).

When the connection determination time counter t is at a value other than 0, the MPU 161 determines whether or not the connection state judge buffer SJ is in connection state D (step S7).

When the connection state judge buffer SJ is the connection state D, the MPU 161 proceeds to the next step.

When the connection state judge buffer SJ is not in the connection state D, the MPU 161 assigns 0 to the connection determination time counter t (step S8) and proceeds to the next step.

Next, the MPU 161 assigns the connection state D to the connection state judge buffer SJ (Step S9).

Next, the MPU 161 determines whether or not 100 ms has elapsed (step S10).

The MPU 161 repeats S10 until 100 ms has elapsed.

Next, the MPU 161 determines whether or not the connection determination time counter t has become t=2 (step S11).

When the connection determination time counter t is not t=2, the MPU 161 assigns t+1 to the connection determination time counter t (step S12) and repeats S5-S12.

When the connection determination time counter t is t=2, the MPU 161 determines that the connection state of the endoscope 102 is D (step S13). In such a case, the MPU 161 reads out setting information of the connection state D from the FRAM 162 and performs operation setting of the light source (Step S14).

Here, the setting information of the connection state D has the settings shown in Table 2, and the setting of the light source device 103 is conducted in accordance with these settings.

The MPU 161 starts the normal operation of the light source device 103 (step S15).

A user holds down the filter mode switch 188*a* of the illumination mode setting display unit 188, and selects the special light observation mode displayed in the special light observation display unit 188*b*.

The light source device 103, based on the selected special light observation mode, controls each unit in the device via the MPU 161 controlling each unit on the control board 145.

Here, the MPU 161 controls the observation mode switching turret control unit 163 so that the observation filter from among the observation filters 191*a*-191*e* that corresponds to the selected observation mode is set on the optical path. The MPU 161 also controls and drives the motor 159*a*.

At the same time, the MPU 161 controls the neutral density mesh turret control unit 164 so that the neutral density mesh filter from among the neutral density mesh filters 192*a*-192*d* that corresponds to the selected observation mode is set on the optical path. The MPU 161 also controls and drives the motor 159*b*.

The MPU 161 controls the diaphragm control unit 165 so that the diaphragm 149 limits the light intensity of the illuminating light in accordance with the selected observation mode and controls and drives the motor 159*c*.

There is a case in which a user, during the endoscopic examination, removes the high-brightness rigid endoscope 114 from the light source device 103 and connects a normal rigid endoscope 113 to the light source device 103 for a particular use.

In such a case, during the high-brightness mode, the light source connector 124*d* of the high-brightness rigid endoscope 114 is pulled out of the connector receiver unit 141 and the light source connector 124*c* of the normal rigid endoscope 113 is newly connected to the connector receiver unit 141.

At that time, high-brightness illuminating light must not be supplied to the normal rigid endoscope 113 from the light source device 103.

For that reason, when the light source connector 124*d* of the high-brightness rigid endoscope 114 is ejected from the connector receiver unit 114 while in high-brightness mode, the light source device 103 sets the maximum of the light intensity of the illuminating light to be low. The same is set when the connection is changed from the high-brightness rigid endoscope 114 to the normal flexible endoscope 111.

The MPU 161 prevents high-brightness light intensity from being supplied to the normal endoscope 111 by the combination of the observation filters 191*a*-191*e* of the observation mode switching turret 151 and the neutral density mesh filters 192*a*-192*d* of the neutral density mesh turret 52, as described in Table 3.

Here, the endoscope connection detection unit 166 changes the detection time of the ON/OFF signal detected by the endoscope connection detection sensor 201*a*-201*c* on the bases of whether or the light source connectors (124*a*, 124*c* or 124*d*) are connected to the connector receiver unit 141.

In other words, the endoscope connection detection unit 166 detects the endoscope 102 with a longer ON/OFF signal detection time detected by the endoscope connection detection sensor 201*a*-201*c* when the light source connector (124*a*, 124*c*, or 124*d*) is connected to the connector receiver unit 141.

On the other hand, the endoscope connection detection unit 166 shortens the detection time of the ON/OFF signal detected by the endoscope connection detection sensor 201*a*-201*c* when the light source connector (124*a*, 124*c* or 124*d*) is ejected from the connector receiver unit 141, and immediately changes the setting of the light source device 103 to the unconnected setting. At that time, in addition, the diaphragm 149, as explained above, is controlled to be half open.

Figure 42:
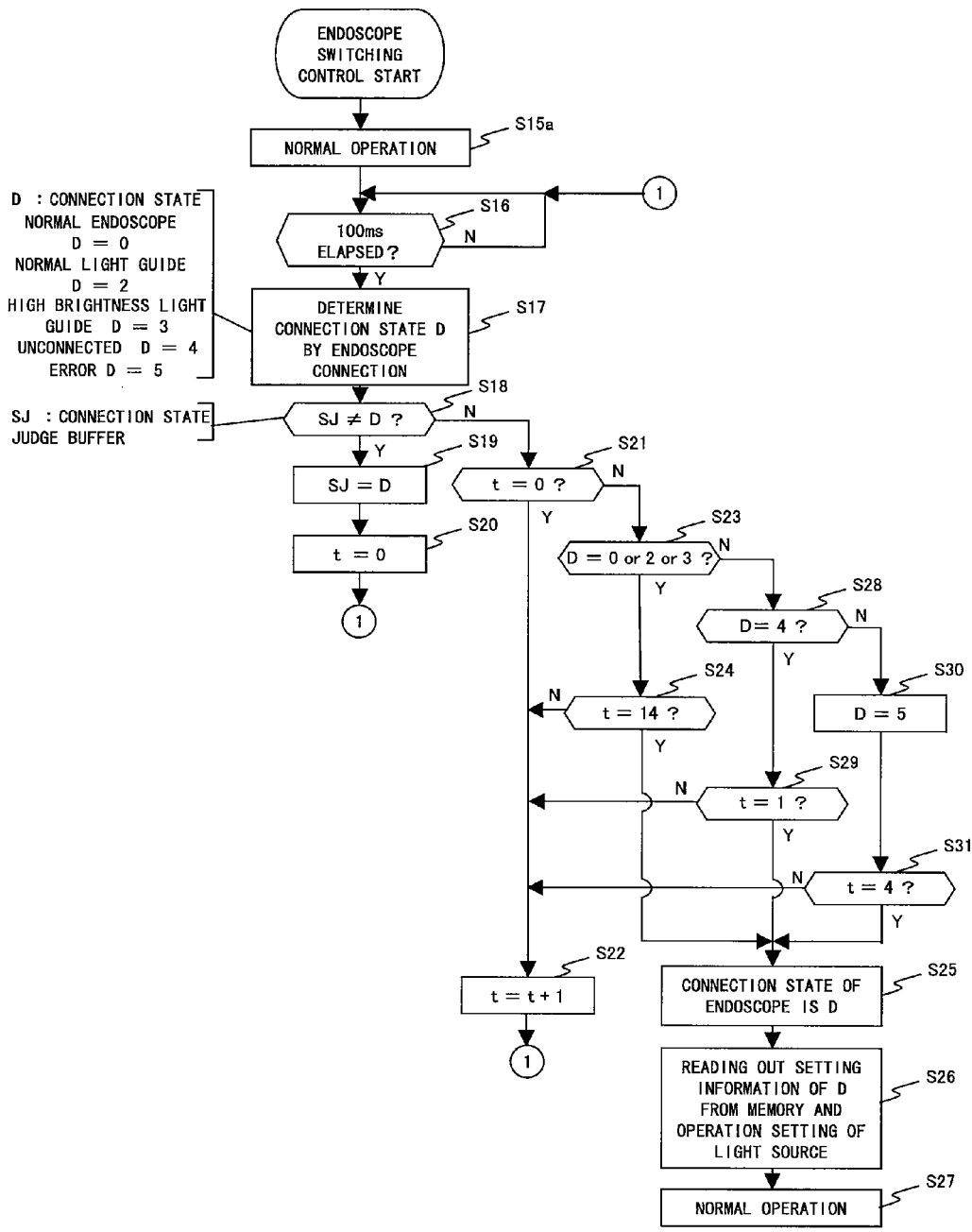
FIG. 42 is a flowchart of an endoscope switching control operated by the MPU in the second mode.

Here, the MPU 161 of the light source device 103 controls each unit in the device by controlling each unit of the control board 145 in accordance with the endoscope switching control flowchart shown in FIG. 42.

FIG. 42 is a flowchart of an endoscope switching control operation performed by the MPU. As shown in FIG. 42, the MPU 161 determines whether, from normal operation (step S15*a*), 100 ms has elapsed or not (step S16).

The MPU 161 repeats S16 until 100 ms has elapsed.

Next, the MPU 161 determines the connection state D detected by the endoscope connection detection unit 166 in the same manner as S5 (step S17).

Next, the MPU 161 determines whether or not the connection state judge buffer SJ is in the connection state D (step S18).

In step S18, if the connection state judge buffer SJ is not in the connection state D, the MPU 161 assigns D to the connection state judge buffer SJ (step S19). The connection determination time counter t is assigned the value 0 (step S20), and the operation returns to S16.

In S18, if the connection state judge buffer SJ is in the connection state D, the MPU 161 determines whether or not the connection determination time counter t is 0 (step S21).

In S21, if the connection determination time counter t is 0, the MPU 161 assigns t+1 to the connection determination time counter t (step S22), and the operation returns to S16.

In S21, if the connection determination time counter t is not 0, the MPU 161 determines the connection state to be 0, 2, or 3 (step S23).

In S23, if the connection state D is either 0, 2, or 3, the MPU 161 determines whether or not the connection determination time counter t is 14 (step S24).

In step S24, if the connection determination time counter t is not 14, the MPU 161 assigns t+1 to the connection determination time counter t (step S22), and the operation returns to S16.

In S24, if the connection determination time counter t is 14, the MPU 161 determines that the connection state of the endoscope 102 is D (step S25), reads out the setting information of the connection state D from the FRAM 162, and sets the operation of the light source (step S26). Then, the MPU 161 returns to the normal operation of the light source device 103 (step S27).

In step S23, if the connection state D is not 0, 2, or 3, the MPU 161 determines whether or not the connection state D is 4 (step S28).

In S2, if the connection state D is 4, the MPU 116 determines whether or not the value of the connection determination time counter t is 1 (step S29).

In S29, if the value of the connection determination time counter t is not 1, the MPU 161 assigns the value t+1 to the connection determination time counter t (step S22), and the operation returns to S16.

In S29, if the value of the connection determination time counter t is 1, the MPU 161 determines that the connection state of the endoscope 102 is D (step S25), reads out the setting information of the connection state D from the FRAM 162, and performs operation setting of the light source (step S26). Then, the MPU 161 returns to normal operation of the light source device 103 (step S27).

In S28, if the connection state D is not 4, the MPU 161 determines that the connection state D is 5 (step S30). Next, it is determined whether the value of the connection determination time counter t is 4 (step S31).

In S31, if the value of the connection determination time counter t is not 4, the MPU 161 assigns t+1 to the connection determination time counter t (step S22), and the operation returns to S16.

In step S31, if the value of the connection determination time counter t is 4, the MPU 161 determines that the connection state of the endoscope 102 is D (step S25). The MPU 161 reads out the setting information of the connection state D from the FRAM 162 and performs operation setting of the light source (step S26). Then, the MPU 161 returns to the normal operation of the light source device 103 (step S27).

It is thus possible during endoscopic examination to set the settings in accordance with the connected endoscope 102 in the light source device 103 even if, for example, the endoscope 102 is changed and connected. Note that the setting values (t=0, 1, 4, 14 etc.) for determination of the counter value of the counter t explained in the above flowchart are not limited to those numbers; however, the value may be changed according to the setting environment.

In a case in which the connection state D is 5, the MPU 161 is configured to set, while issuing an error notice, the connection setting of the normal rigid endoscope 113 so that the barebones examination can be continued.

There is a case in which a user may change the settings of the light source device 103 via the operation panel 182 of the front panel 147 during the endoscopic examination. In such a case, the light source device 103, in which the setting is changed via the MPU 161, controls each unit in the device on the basis of the settings by controlling each unit of the control board 145.

Figure 43:
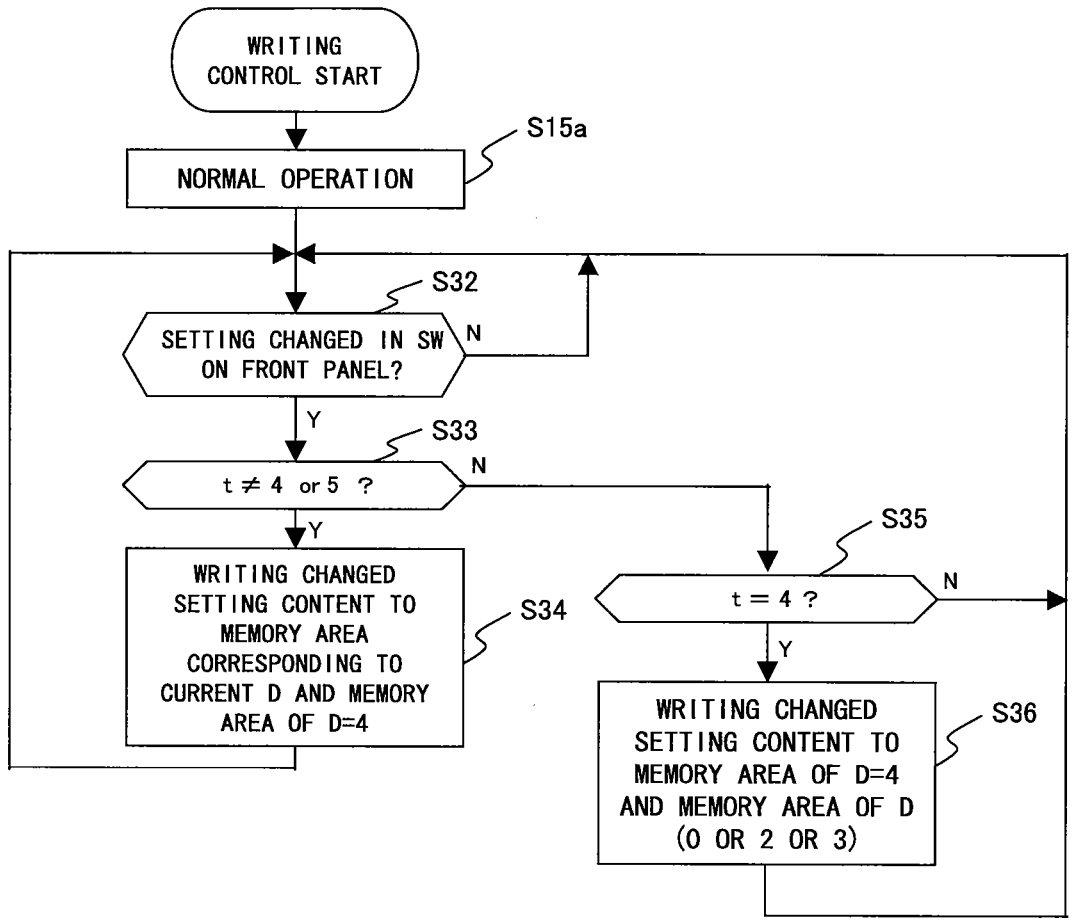
FIG. 43 is a flowchart of a memory write-in control operated by the MPU in the second mode.

Here, the MPU 161 of the light source device 103 writes the changed settings in the FRAM 162 in accordance with the memory write-in control flowchart shown in FIG. 43.

FIG. 43 is a flowchart of a memory write-in control operated by the MPU. The MPU 161, during normal operation (step S15a), determines whether or not the setting is changed by a switch (SW) provided in the operation panel 182 of the front panel 147 (step S32).

The MPU 161 repeats S32 until the setting is changed via the switch on the operation panel 182.

If the setting is changed via the switch on the operation panel 182, the MPU 161 determines whether the connection state D is not 4 or 5 (step S33).

In S33, if the connection state D is not 4 or 5, the MPU 161 writes the changed settings in each memory area of the FRAM 162 corresponding to the current connection state D and in the memory area of the FRAM 162 corresponding to the connection state D=4 (step S34), and the operation returns to S32.

In S33, if the connection state D is 4 or 5, the MPU 161 determines whether or not the connection state D is 4 (step S35).

In S35, if the connection state D is 4, the MPU 161 writes the changed settings in each memory area of the FRAM 162 corresponding to the connection state D=4, and in the memory area of the FRAM 62 corresponding to the connection state D (0, 2, or 3) (step S36), and the operation returns to S32.

In S35, if the connection state D is not 4, the MPU 161 returns the operation to S32.

By doing this, the light source device 103 can set each unit in the device according to the stored settings when starting up after the changed settings are stored in the FRAM 162.

There is a case in which a user, during endoscopic examination for example, may change the observation mode via the operation panel 182 of the front panel 147.

The user holds down the filter mode switch 188a of the illumination mode setting display unit 188 and selects the special light observation mode displayed in the special light observation display unit 188b.

The light source device 103, based on the selected special light observation mode, controls each unit in the device via the control of each unit of the control board 145 by the MPU.

Figure 44:
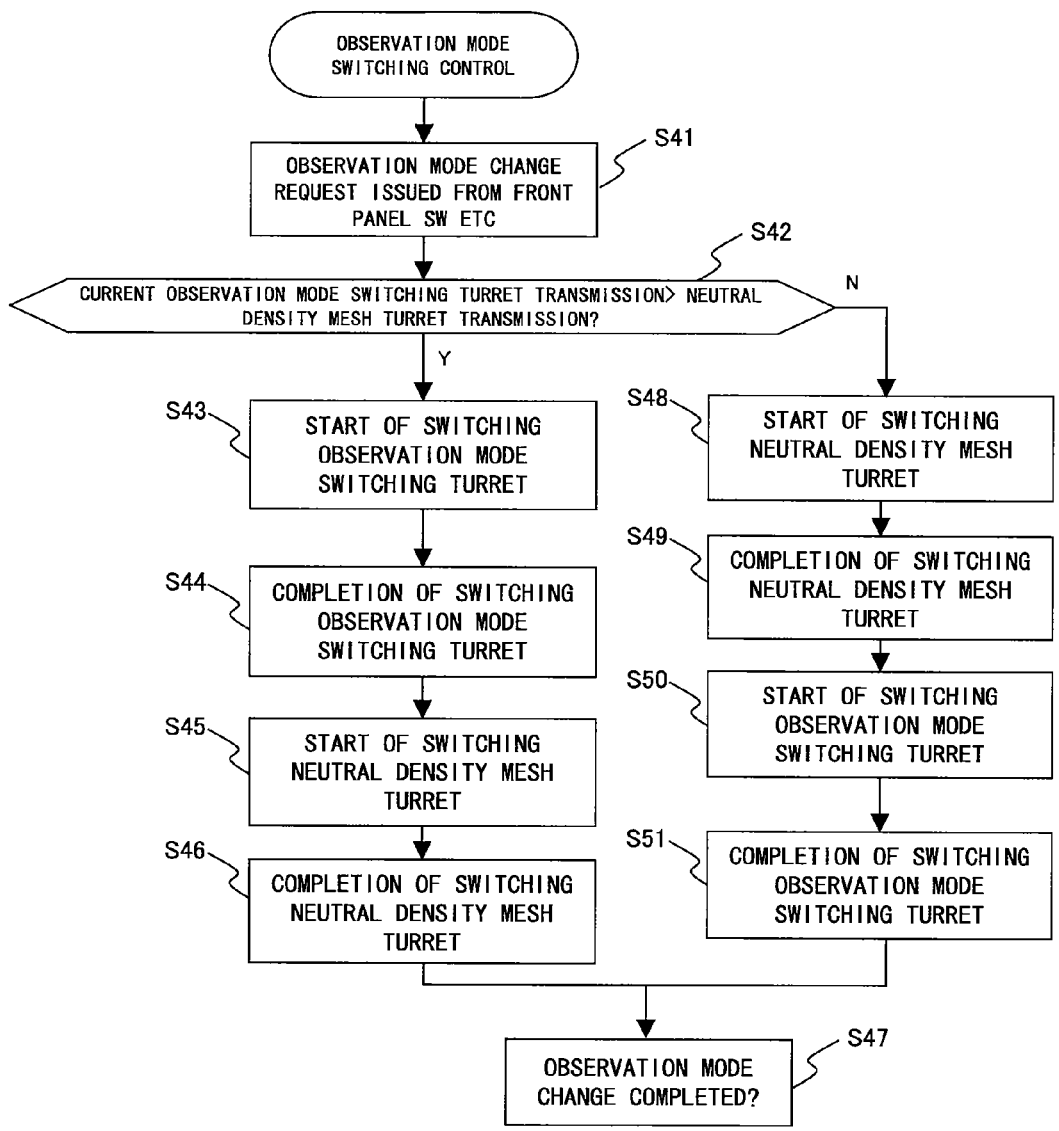
FIG. 44 is a flowchart of the observation mode switching control operated by the MPU in the second mode.

The MPU 161 of the light source device 103 switches the observation mode in accordance with the observation mode switching control flowchart shown in FIG. 44.

FIG. 44 is a flowchart of the observation mode switching control operated by the MPU. In the light source device 103, an observation mode change request is generated by a switch (the filter mode switch 188a of the illumination mode setting display unit 188) provided on the operation panel 182 of the front panel 147 (step S41).

Then, the MPU 161 determines whether or not the transmission of the current observation switching turret 151 is greater than that of the neutral density mesh turret 152 (step S42).

In S42, if the transmission of the current observation switching turret 151 is greater than that of the neutral density mesh turret 52, the MPU 161 starts switching of the observation mode switching turret 151 (step S43).

The MPU 161 controls the observation mode switching turret control unit 163 so that the observation filter from among the observation filters 191a-191e that corresponds to the selected observation mode is set on the optical path. The MPU 161 also controls and drives the motor 159a.

Then, the MPU 161 completes the switching of the observation mode switching turret 151 (step S44).

Next, the MPU 161 starts switching the neutral density mesh turret 152 (step S45). The MPU 161 controls the neutral density mesh turret control unit 164 so that the neutral density mesh filter from among the neutral density mesh filters 192a-

192d that corresponds to the selected observation mode is set on the optical path. The MPU 161 also controls and drives the motor 159b.

Then, the MPU 161 completes the switching of the neutral density mesh turret 152 (step S46) and the observation mode change is completed (step S47).

In S42, if the transmission of the current observation mode switching turret 151 is smaller than that of the neutral density mesh turret 152, the MPU 161 starts the switching of the neutral density mesh turret 152 (step S48).

The MPU 161 controls the neutral density mesh turret control unit 164 so that the neutral density mesh filter from among the neutral density mesh filters 192a-192d that corresponds to the selected observation mode is set on the optical path. The MPU 161 also controls and drives the motor 159b.

Then, the MPU 161 completes the switching of the neutral density mesh turret (step S49).

Next, the MPU 161 starts the switching of the observation mode switching turret 151 (step S50).

The MPU 161 controls the observation mode switching turret control unit 63 so that the observation filter from among the observation filters 191a-191e that corresponds to the selected observation mode is set on the optical path. The MPU 161 also controls and drives the motor 159a.

Then, the MPU 161 completes the switching of the observation mode switching turret 151 (step S51) and the observation mode change is completed (step S47).

By doing this, the light source device 103 can automatically change the setting in accordance with the changed observation mode even if the observation mode is changed during the operation.

It should be noted that the present invention is not limited to the embodiments described above; many modifications and variations can be made thereto without departing from the scope and gist of the inventions.

The light source device for an endoscope in the present embodiment comprises an endoscope connection unit that can be selectively connected to a plurality of types of endoscopes, a light source for generating illuminating light supplied to an endoscope connected to the endoscope connection unit, an optical system guiding illuminating light generated from the light source to the endoscope, an observation filter turret comprising a plurality of types of observation filters for limiting the wavelength range of light from the light source in accordance with an observation mode of the endoscope and that is able to set an observation filter corresponding to the observation mode of the endoscope on an optical path of the optical system, and a neutral density filter turret comprising a plurality of types of neutral density filters for darkening light from the light source in accordance with an observation mode of the endoscope and that is able to set a neutral density filter corresponding to the endoscope on an optical path of the optical system.

In the above light source for an endoscope, the neutral density filter on the neutral density filter turret is a neutral density mesh filter.

In the above light source for an endoscope, the neutral density filter turret can rotate or can move in parallel so that the neutral density filter corresponding to the endoscope is set on an optical path of the optical system.

The light source device for an endoscope in the present embodiment comprises an endoscope connection unit that can be selectively connected to a plurality of types of endoscopes, a detection sensor inside the endoscope connection unit for detecting the type of endoscope, a detection unit for detecting the type of the endoscope on the basis of a signal from the detection sensor, memory for storing settings in accordance with the type of endoscope, and a control unit for making an automatic setting in accordance with the settings stored in the memory on the basis of a detection result of the detection unit.

In the above light source device for an endoscope, the detection unit changes the detection time when the endoscope is connected to the endoscope connection unit from the detection time when the endoscope is removed from the endoscope connection unit.

In the light source device for an endoscope, also, the detection unit shortens the detection time when the endoscope is removed from the endoscope connection unit and changes the settings to the settings that exist when the endoscope is not connected.

AS described above, the light source device of the present invention has an effect in which various optical filters, special light filters and neutral density mesh filters are provided, the device can be downsized. In addition, in the light source device for an endoscope of the present invention, it is possible to automatically change the setting in accordance with the type of endoscope connected.

What is claimed is:

1. A light source device for an endoscope comprising:
a light source for supplying illuminating light to an object;
an endoscope connection unit optically connectable to an endoscope having a different connector shape depending on a type of endoscope; and
an endoscope connection detection unit for detecting whether or not the endoscope has been connected to the endoscope connection unit;
a connection detection time interval changing unit for changing an interval between each detection for detecting connection of the endoscope while the endoscope is not connected to the endoscope connection unit so that the interval is shorter than an interval between each detection for detecting connection of the endoscope while the endoscope is connected to the endoscope connection unit, and wherein
the endoscope connection detection unit further identifies the type of the endoscope based on a detection result when the endoscope is connected to the endoscope connection unit,
the light source further comprises:
an illumination condition changing unit for changing an illumination condition of the illuminating light;
a storage unit for storing a setting content that depends on the type of the endoscope; and
a control unit for controlling the illumination condition changing unit based on the detection result by the endoscope connection detection unit and in accordance with the setting content stored in the storage unit, and wherein
the control unit makes an automatic setting according to the setting content stored in the storage unit based on an identification result by the endoscope connection detection unit, and wherein
the endoscope connection detection unit makes a difference in the identification time required to identify the endoscope between a case in which the endoscope is connected to the endoscope connection unit and a case in which the endoscope is removed from the endoscope connection unit.

2. The light source device for an endoscope according to claim 1, wherein
the illumination condition changing unit changes a mode to any of a plurality of illumination modes, including a narrowband light observation mode, a fluorescent observation mode, and an infrared mode.

3. The light source device for an endoscope according to claim 1, wherein
the illumination condition changing unit changes a mode to any of a plurality of illumination modes including a high-brightness mode.

4. The light source device for an endoscope according to claim 1, wherein
the endoscope connection detection unit identifies which one of the following the
endoscope is: a normal flexible endoscope, a normal rigid endoscope, or a high-brightness endoscope, according to the detection result.

5. The light source device for an endoscope according to claim 4, wherein
the illumination condition changing unit changes the mode to any of a plurality of illumination modes, including a narrowband light observation mode, a fluorescent observation mode, or an infrared mode, based on the type of endoscope identified by the endoscope connection detection unit.

6. The light source device for an endoscope according to claim 1, wherein
the illumination condition changing unit changes the mode to any of a plurality of illumination modes, including a high-brightness mode, based on the type of endoscope identified by the endoscope connection detection unit.

7. The light source device for an endoscope according to claim 1, wherein
the illumination condition changing unit comprises
a light intensity adjusting mesh provided on an optical path between the light source and the endoscope connection unit, and
an insertion/removal unit for inserting or removing the light intensity adjusting mesh to or from the optical path.

8. The light source device for an endoscope according to claim 1, wherein
the changing unit comprises either a light intensity adjusting mesh, an optical filter limiting optical transmission band, or both, that is provided between the light source and the endoscope connection unit.

9. The light source device for an endoscope according to claim 8, further comprising
an insertion/removal unit for inserting or removing the light intensity adjusting mesh and the optical filter to or from an optical path formed by the illuminating light.

10. The light source device for an endoscope according to claim 8, wherein
the light intensity adjusting mesh is provided for a turret, and
the turret can rotate or moves in parallel so as to be able to set the light intensity adjusting mesh corresponding to the endoscope to the optical path of the optical system.

11. The light source device for an endoscope according to claim 1, further comprising
a setting panel for setting the illumination condition, wherein the setting panel comprises
a plurality of setting instruction unit for making the setting, and
a back light for lighting up each of the setting instruction unit from the back,
the control unit controls the backlight so as to light up the setting instruction unit, which can be operated in accordance with the illumination condition based on the endoscope connection detection unit.

12. The light source device for an endoscope according to claim 1, further comprises
a connection determination unit for determining whether or not a light guide connector of the endoscope is connected to the endoscope connection unit.

13. The light source device for an endoscope according to claim 12, further comprises
light shielding unit, provided on the optical path of the illuminating light emitted from the light source, for shielding the illuminating light on the optical path when the light guide connector is not connected.

14. The light source device for an endoscope according to claim 12, wherein
the control unit, based on results obtained by the connection determination unit and the endoscope connection detection unit, switches a setting switch of the light source device for an endoscope or a display unit.

15. The light source device for an endoscope according to claim 1, further comprising
an optical system guiding illuminating light generated from the light source to the endoscope,
wherein
the illumination condition changing unit comprises:
an observation filter turret comprising a plurality of types of observation filters for limiting a wavelength range of light from the light source in accordance with an observation mode of the endoscope and that is able to set an observation filter corresponding to the observation mode of the endoscope on an optical path of the optical system; and
a neutral density filter turret comprising a plurality of types of neutral density filters for darkening light from the light source in accordance with an observation mode of the endoscope and that is able to set a neutral density filter corresponding to the endoscope on an optical path of the optical system.

16. The light source device according to claim 1, wherein
when it is determined that the endoscope has not been connected to the endoscope connection unit, the control unit changes the setting content to the setting content stored in the storage unit.

17. A light source device for an endoscope comprising:
an endoscope connection unit that can be selectively connected to a plurality of types of endoscopes;
a detection sensor, provided in the endoscope connection unit, for detecting whether or not the endoscope has been connected;
a detection unit for detecting whether the endoscope has been connected or not based on a signal from the detection sensor;
a connection detection time interval changing unit for changing an interval between each detection for detecting connection of the endoscope while the endoscope is not connected to the endoscope connection unit so that the interval is shorter than an interval between each detection for detecting connection of the endoscope while the endoscope is connected to the endoscope connection unit;
a memory for storing a setting content that depends on whether the endoscope has been connected or not; and
a control unit for making an automatic setting in accordance with the setting content stored in the memory based on a detection result of the detection unit, and wherein the endoscope connection detection unit further identifies the type of the endoscope based on a detection result when the endoscope is connected to the endoscope connection unit, the light source further comprises:
- an illumination condition changing unit for changing an illumination condition of the illuminating light
- a storage unit for storing a setting content that depends on the type of the endoscope; and
- a control unit for controlling the illumination condition changing unit based on the detection result by the endoscope connection detection unit and in accordance with the setting content stored in the storage unit, and wherein the control unit makes an automatic setting according to the setting content stored in the storage unit based on an identification result by the endoscope connection detection unit, and wherein the endoscope connection detection unit makes a difference in the identification time required to identify the endoscope between a case in which the endoscope is connected to the endoscope connection unit and a case in which the endoscope is removed from the endoscope connection unit.

* * * * *